(12) United States Patent
Horvath et al.

(10) Patent No.: US 11,938,059 B2
(45) Date of Patent: Mar. 26, 2024

(54) INTRAOCULAR SHUNT INSERTION TECHNIQUES

(71) Applicant: AqueSys, Inc., Parsippany, NJ (US)

(72) Inventors: Christopher Horvath, Mission Viejo, CA (US); Laszlo O. Romoda, San Clemente, CA (US); Iqbal K. Ahmed, Mississauga (CA); Brian Scott Hamstrom, Oceanside, CA (US); Wesley Anne Jung, Trabuco Canyon, CA (US); Vanessa I. Vera, Mission Viejo, CA (US); Ronald D. Bache, Mission Viejo, CA (US)

(73) Assignee: AqueSys, Inc., Parsippany, NJ (US)

( * ) Notice: Subject to any disclaimer, the term of this patent is extended or adjusted under 35 U.S.C. 154(b) by 1009 days.

(21) Appl. No.: 16/854,908

(22) Filed: Apr. 22, 2020

(65) Prior Publication Data

US 2020/0246188 A1 Aug. 6, 2020

Related U.S. Application Data

(63) Continuation of application No. 15/451,274, filed on Mar. 6, 2017, now Pat. No. 10,653,555, which is a
(Continued)

(51) Int. Cl.
*A61F 9/007* (2006.01)
*A61B 90/00* (2016.01)
(Continued)

(52) U.S. Cl.
CPC .......... *A61F 9/00781* (2013.01); *A61B 90/02* (2016.02); *A61F 9/0008* (2013.01);
(Continued)

(58) Field of Classification Search
CPC .. A61F 9/00781; A61F 9/0008; A61F 9/0017; A61F 9/007; A61M 5/3286; A61M 27/002; A61M 2210/0612
See application file for complete search history.

(56) References Cited

U.S. PATENT DOCUMENTS

| 2,902,995 A | 9/1959 | Loper |
| 3,491,757 A | 1/1970 | Olvera |
(Continued)

FOREIGN PATENT DOCUMENTS

| CN | 1402625 | 3/2003 |
| CN | 1794957 A | 6/2006 |
(Continued)

OTHER PUBLICATIONS

Office Action and Examination Report from Indian Application No. 202118059143 dated Apr. 1, 2022; 6 pages.
(Continued)

*Primary Examiner* — Julian W Woo
(74) *Attorney, Agent, or Firm* — Stanek Lemon Crouse & Meeks, PA

(57) ABSTRACT

An inserter for treating glaucoma can comprise a housing, a needle, a plunger, a slider component, and a drive component. The drive component is disposed within a cavity of the housing and rotatable within the cavity to result in movement along a longitudinal axis of the inserter to the needle and the plunger upon rotation of the drive component. The slider component is coupled to the housing and slidable along an elongate groove of the drive component such that movement of the slider component along the axis rotates the drive component within the housing.

20 Claims, 30 Drawing Sheets

Related U.S. Application Data continuation of application No. 14/541,070, filed on Nov. 13, 2014, now Pat. No. 9,585,790.

(60) Provisional application No. 61/904,429, filed on Nov. 14, 2013.

(51) Int. Cl.
  *A61F 9/00* (2006.01)
  *A61M 5/32* (2006.01)
  *A61M 27/00* (2006.01)

(52) U.S. Cl.
  CPC ......... *A61F 9/0017* (2013.01); *A61M 5/3286* (2013.01); *A61M 27/002* (2013.01); *A61M 2210/0612* (2013.01)

(56) References Cited

U.S. PATENT DOCUMENTS

| | | |
|---|---|---|
| 3,654,932 A | 4/1972 | Newkirk |
| 3,788,327 A | 1/1974 | Donowitz et al. |
| 3,960,150 A | 6/1976 | Hussain et al. |
| 4,090,530 A | 5/1978 | Lange |
| 4,402,308 A | 9/1983 | Scott |
| 4,431,688 A | 2/1984 | Kornmann |
| 4,562,463 A | 12/1985 | Lipton |
| 4,583,117 A | 4/1986 | Lipton et al. |
| 4,613,329 A | 9/1986 | Bodicky |
| 4,700,692 A | 10/1987 | Baumgartner |
| 4,722,724 A | 2/1988 | Schocket |
| 4,730,613 A | 3/1988 | Gordy |
| 4,740,205 A | 4/1988 | Seltzer |
| 4,744,362 A | 5/1988 | Grundler |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |
| 4,836,201 A | 6/1989 | Patton et al. |
| 4,848,340 A | 7/1989 | Bille et al. |
| 4,863,457 A | 9/1989 | Lee |
| 4,902,292 A | 2/1990 | Joseph |
| 4,908,024 A | 3/1990 | Py |
| 4,911,161 A | 3/1990 | Schechter |
| 4,915,684 A | 4/1990 | MacKeen et al. |
| 4,934,363 A | 6/1990 | Smith et al. |
| 4,936,825 A | 6/1990 | Ungerleider |
| 4,946,436 A | 8/1990 | Smith |
| 4,968,296 A | 11/1990 | Ritch et al. |
| 4,976,688 A | 12/1990 | Rosenblum |
| 4,978,352 A | 12/1990 | Fedorov et al. |
| 5,035,695 A | 7/1991 | Weber et al. |
| 5,041,081 A | 8/1991 | Odrich |
| 5,057,098 A | 10/1991 | Zelman |
| 5,071,408 A | 12/1991 | Ahmed |
| 5,092,837 A | 3/1992 | Ritch et al. |
| 5,098,426 A | 3/1992 | Sklar et al. |
| 5,098,443 A | 3/1992 | Parel et al. |
| 5,162,641 A | 11/1992 | Fountain |
| 5,167,645 A | 12/1992 | Castillo |
| 5,178,604 A | 1/1993 | Baerveldt et al. |
| 5,180,362 A | 1/1993 | Worst |
| 5,201,750 A | 4/1993 | Hocherl et al. |
| 5,207,660 A | 5/1993 | Lincoff |
| 5,273,530 A | 12/1993 | Del Cerro |
| 5,275,622 A | 1/1994 | Lazarus et al. |
| 5,290,295 A | 3/1994 | Querals et al. |
| 5,300,020 A | 4/1994 | L'Esperance, Jr. |
| 5,333,619 A | 8/1994 | Burgio |
| 5,338,291 A | 8/1994 | Speckman et al. |
| 5,342,370 A | 8/1994 | Simon et al. |
| 5,351,678 A | 10/1994 | Clayton |
| 5,360,339 A | 11/1994 | Rosenberg |
| 5,368,015 A | 11/1994 | Wilk |
| 5,370,607 A | 12/1994 | Memmen |
| 5,372,583 A | 12/1994 | Roberts et al. |
| 5,399,951 A | 3/1995 | Lavallee et al. |
| 5,410,638 A | 4/1995 | Colgate et al. |
| 5,441,483 A | 8/1995 | Avitall |
| 5,443,505 A | 8/1995 | Wong et al. |
| 5,472,439 A | 12/1995 | Hurd |
| 5,476,445 A | 12/1995 | Baerveldt et al. |
| 5,516,522 A | 5/1996 | Peyman et al. |
| 5,520,631 A | 5/1996 | Nordquist et al. |
| 5,545,206 A | 8/1996 | Carson |
| 5,558,629 A | 9/1996 | Baerveldt et al. |
| 5,558,630 A | 9/1996 | Fisher |
| 5,601,094 A | 2/1997 | Reiss |
| 5,656,026 A | 8/1997 | Joseph |
| 5,665,093 A | 9/1997 | Atkins et al. |
| 5,665,114 A | 9/1997 | Weadock et al. |
| 5,670,161 A | 9/1997 | Healy et al. |
| 5,688,562 A | 11/1997 | Hsuing |
| 5,695,474 A | 12/1997 | Daugherty |
| 5,704,907 A | 1/1998 | Nordquist et al. |
| 5,707,376 A | 1/1998 | Kavteladze et al. |
| 5,722,948 A | 3/1998 | Gross |
| 5,743,868 A | 4/1998 | Brown et al. |
| 5,763,491 A | 6/1998 | Brandt et al. |
| 5,868,697 A | 2/1999 | Richter et al. |
| 5,868,771 A | 2/1999 | Herbert et al. |
| 5,888,200 A | 3/1999 | Walen |
| 5,908,449 A | 6/1999 | Bruchman et al. |
| 5,928,424 A | 7/1999 | Krebs et al. |
| 5,932,299 A | 8/1999 | Katoot |
| 5,938,583 A | 8/1999 | Grimm |
| 5,964,747 A | 10/1999 | Eaton et al. |
| 6,007,511 A | 12/1999 | Prywes |
| 6,007,578 A | 12/1999 | Schachar |
| 6,050,970 A | 4/2000 | Baerveldt et al. |
| 6,086,543 A | 7/2000 | Anderson et al. |
| 6,102,045 A | 8/2000 | Nordquist et al. |
| 6,146,366 A | 11/2000 | Schachar |
| 6,159,218 A | 12/2000 | Aramant et al. |
| 6,165,210 A | 12/2000 | Lau et al. |
| 6,203,513 B1 | 3/2001 | Yaron et al. |
| 6,228,023 B1 | 5/2001 | Zaslavsky et al. |
| 6,228,873 B1 | 5/2001 | Brandt et al. |
| 6,231,546 B1 | 5/2001 | Milo |
| 6,261,256 B1 | 7/2001 | Ahmed |
| 6,264,665 B1 | 7/2001 | Yu et al. |
| 6,280,468 B1 | 8/2001 | Schachar |
| 6,413,540 B1 | 7/2002 | Yaacobi |
| 6,450,937 B1 | 9/2002 | Mercereau et al. |
| 6,450,984 B1 | 9/2002 | Lynch et al. |
| 6,464,698 B1 | 10/2002 | Falwell |
| 6,464,724 B1 | 10/2002 | Lynch et al. |
| 6,471,666 B1 | 10/2002 | Odrich |
| 6,483,930 B1 | 11/2002 | Musgrave et al. |
| 6,514,238 B1 | 2/2003 | Hughes |
| 6,524,275 B1 | 2/2003 | Lynch et al. |
| 6,533,768 B1 | 3/2003 | Hill |
| 6,544,249 B1 | 4/2003 | Yu et al. |
| 6,558,342 B1 | 5/2003 | Yaron et al. |
| 6,595,945 B2 | 7/2003 | Brown |
| 6,638,239 B1 | 10/2003 | Bergheim et al. |
| 6,645,183 B2 | 10/2003 | Christensen |
| 6,666,841 B2 | 11/2003 | Gharib et al. |
| 6,676,998 B2 | 1/2004 | Huang et al. |
| 6,699,210 B2 | 3/2004 | Williams et al. |
| 6,726,664 B2 | 4/2004 | Yaron et al. |
| D490,152 S | 5/2004 | Myall et al. |
| 6,736,791 B1 | 5/2004 | Tu et al. |
| 6,752,753 B1 | 6/2004 | Hoskins et al. |
| 6,881,198 B2 | 4/2005 | Brown |
| 6,936,053 B1 | 8/2005 | Weiss |
| 6,939,298 B2 | 9/2005 | Brown et al. |
| 7,008,396 B1 | 3/2006 | Straub |
| 7,037,335 B2 | 5/2006 | Freeman et al. |
| 7,041,077 B2 | 5/2006 | Shields |
| 7,094,225 B2 | 8/2006 | Tu et al. |
| 7,118,547 B2 | 10/2006 | Dahan |
| 7,135,009 B2 | 11/2006 | Tu et al. |
| 7,163,543 B2 | 1/2007 | Smedley et al. |

(56) References Cited

U.S. PATENT DOCUMENTS

| | | |
|---|---|---|
| 7,186,232 B1 | 3/2007 | Smedley et al. |
| 7,192,412 B1 | 3/2007 | Zhou et al. |
| 7,207,980 B2 | 4/2007 | Christian et al. |
| 7,291,125 B2 | 11/2007 | Coroneo |
| 7,297,154 B2 | 11/2007 | Tu et al. |
| 7,331,984 B2 | 2/2008 | Tu et al. |
| 7,344,528 B1 | 3/2008 | Tu et al. |
| 7,431,709 B2 | 10/2008 | Pinchuk et al. |
| 7,431,710 B2 | 10/2008 | Tu et al. |
| 7,458,953 B2 | 12/2008 | Peyman et al. |
| 7,468,065 B2 | 12/2008 | Weber et al. |
| 7,488,303 B1 | 2/2009 | Haffner et al. |
| 7,524,298 B2 | 4/2009 | Gharib et al. |
| 7,594,899 B2 | 9/2009 | Pinchuk |
| 7,625,384 B2 | 12/2009 | Eriksson et al. |
| 7,837,644 B2 | 1/2010 | Pinchuk et al. |
| 7,658,729 B2 | 2/2010 | Hull |
| 7,678,065 B2 | 3/2010 | Haffner et al. |
| 7,708,711 B2 | 5/2010 | Tu et al. |
| 7,722,549 B2 | 5/2010 | Nakao |
| 7,717,872 B2 | 6/2010 | Wood et al. |
| 7,740,604 B2 | 6/2010 | Schieber et al. |
| 7,794,437 B2 | 9/2010 | Humayun et al. |
| 7,862,531 B2 | 1/2011 | Yaron et al. |
| 7,867,186 B2 | 1/2011 | Haffner et al. |
| 7,892,282 B2 | 2/2011 | Shepherd |
| 7,998,497 B2 | 8/2011 | de Juan, Jr. et al. |
| 8,003,124 B2 | 8/2011 | Varner et al. |
| 8,109,896 B2 | 2/2012 | Nissan et al. |
| 8,267,882 B2 | 9/2012 | Euteneuer et al. |
| 8,277,437 B2 | 10/2012 | Saal et al. |
| 8,287,494 B2 | 10/2012 | Ma |
| 8,308,701 B2 | 11/2012 | Horvath et al. |
| 8,313,454 B2 | 11/2012 | Yaron et al. |
| 8,337,393 B2 | 12/2012 | Silverstrini et al. |
| 8,337,509 B2 | 12/2012 | Schieber et al. |
| 8,377,122 B2 | 2/2013 | Silvestrini et al. |
| 8,425,449 B2 | 4/2013 | Wardle et al. |
| 8,444,589 B2 | 5/2013 | Silvestrini et al. |
| 8,486,000 B2 | 7/2013 | Coroneo |
| 8,506,515 B2 | 8/2013 | Burns et al. |
| 8,512,404 B2 | 8/2013 | Frion et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini et al. |
| 8,585,629 B2 | 11/2013 | Grabner et al. |
| 8,597,301 B2 | 12/2013 | Mitchell |
| 8,608,632 B1 | 12/2013 | Brigatti et al. |
| 8,663,303 B2 | 3/2014 | Horvath et al. |
| 8,721,702 B2 | 5/2014 | Romoda et al. |
| 8,758,290 B2 | 6/2014 | Horvath et al. |
| 8,765,210 B2 | 7/2014 | Romoda et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,974,511 B2 | 3/2015 | Horvath et al. |
| 9,017,276 B2 | 4/2015 | Horvath et al. |
| 9,044,301 B1 | 6/2015 | Pinchuk et al. |
| 9,095,411 B2 | 8/2015 | Horvath et al. |
| 9,095,413 B2 | 8/2015 | Romoda et al. |
| 9,113,994 B2 | 8/2015 | Romoda et al. |
| 9,125,723 B2 | 9/2015 | Horvath et al. |
| 9,168,172 B1 | 10/2015 | Berdahl |
| 9,192,516 B2 | 11/2015 | Horvath et al. |
| 9,271,869 B2 | 3/2016 | Horvath et al. |
| 9,283,116 B2 | 3/2016 | Romoda et al. |
| 9,326,891 B2 | 5/2016 | Horvath et al. |
| 9,393,153 B2 | 7/2016 | Horvath et al. |
| 9,730,056 B2 | 8/2017 | Rönneke et al. |
| 9,808,373 B2 | 11/2017 | Horvath et al. |
| 10,085,884 B2 | 10/2018 | Reitsamer et al. |
| 10,369,048 B2 | 8/2019 | Horvath et al. |
| 10,653,555 B2 * | 5/2020 | Horvath ............... A61F 9/0017 |
| 2001/0025150 A1 | 9/2001 | de Juan, Jr. et al. |
| 2001/0056254 A1 | 12/2001 | Cragg et al. |
| 2002/0087149 A1 | 7/2002 | McCary |
| 2002/0099434 A1 | 7/2002 | Buscemi et al. |
| 2002/0133168 A1 | 9/2002 | Smedley et al. |
| 2002/0143284 A1 | 10/2002 | Tu et al. |
| 2003/0015203 A1 | 1/2003 | Makower et al. |
| 2003/0050574 A1 | 3/2003 | Krueger |
| 2003/0055372 A1 | 3/2003 | Lynch et al. |
| 2003/0060752 A1 | 3/2003 | Bergheim et al. |
| 2003/0093084 A1 | 5/2003 | Nissan et al. |
| 2003/0097053 A1 | 5/2003 | Itoh |
| 2003/0097151 A1 | 5/2003 | Smedley et al. |
| 2003/0187383 A1 | 10/2003 | Weber et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0077987 A1 | 4/2004 | Rapacki et al. |
| 2004/0111050 A1 | 6/2004 | Smedley et al. |
| 2004/0147870 A1 | 7/2004 | Burns et al. |
| 2004/0154946 A1 | 8/2004 | Solovay et al. |
| 2004/0158269 A1 | 8/2004 | Holman |
| 2004/0193262 A1 | 9/2004 | Shadduck |
| 2004/0199130 A1 | 10/2004 | Chornenky et al. |
| 2004/0210209 A1 | 10/2004 | Yeung |
| 2004/0215133 A1 | 10/2004 | Weber et al. |
| 2004/0216749 A1 | 11/2004 | Tu |
| 2004/0225250 A1 | 11/2004 | Yablonski |
| 2004/0236343 A1 | 11/2004 | Taylor et al. |
| 2004/0254521 A1 | 12/2004 | Simon et al. |
| 2004/0260227 A1 | 12/2004 | Lisk, Jr. et al. |
| 2005/0049578 A1 | 3/2005 | Tu et al. |
| 2005/0101967 A1 | 5/2005 | Weber et al. |
| 2005/0119601 A9 | 6/2005 | Lynch et al. |
| 2005/0143363 A1 | 6/2005 | de Juan, Jr. et al. |
| 2005/0177183 A1 | 8/2005 | Thorne et al. |
| 2005/0246023 A1 | 11/2005 | Yeung |
| 2005/0250788 A1 | 11/2005 | Tu et al. |
| 2005/0261624 A1 | 11/2005 | Wilcox |
| 2005/0267398 A1 | 12/2005 | Protopsaltis et al. |
| 2005/0271704 A1 | 12/2005 | Tu et al. |
| 2005/0277864 A1 | 12/2005 | Haffner et al. |
| 2006/0032507 A1 | 2/2006 | Tu |
| 2006/0052721 A1 | 3/2006 | Dunker et al. |
| 2006/0064112 A1 | 3/2006 | Perez |
| 2006/0106370 A1 | 5/2006 | Baerveldt et al. |
| 2006/0110428 A1 | 5/2006 | de Juan, Jr. et al. |
| 2006/0116625 A1 | 6/2006 | Renati et al. |
| 2006/0147643 A1 | 6/2006 | Volkov et al. |
| 2006/0149194 A1 | 7/2006 | Conston et al. |
| 2006/0155238 A1 | 7/2006 | Shields |
| 2006/0173397 A1 | 8/2006 | Tu et al. |
| 2006/0173446 A1 | 8/2006 | Dacquay et al. |
| 2006/0189932 A1 | 8/2006 | Yang et al. |
| 2006/0200113 A1 | 9/2006 | Haffner et al. |
| 2006/0217740 A1 | 9/2006 | Ghannoum |
| 2006/0241411 A1 | 10/2006 | Field et al. |
| 2006/0241650 A1 | 10/2006 | Weber et al. |
| 2007/0010843 A1 | 1/2007 | Green |
| 2007/0027537 A1 | 2/2007 | Castillejos |
| 2007/0093783 A1 | 4/2007 | Kugler et al. |
| 2007/0118065 A1 | 5/2007 | Pinchuk et al. |
| 2007/0141116 A1 | 6/2007 | Pinchuk et al. |
| 2007/0172903 A1 | 7/2007 | Toner et al. |
| 2007/0191863 A1 | 8/2007 | de Juan, Jr. et al. |
| 2007/0202186 A1 | 8/2007 | Yamamoto |
| 2007/0233037 A1 | 10/2007 | Gifford et al. |
| 2007/0263172 A1 | 11/2007 | Mura |
| 2007/0269487 A1 | 11/2007 | de Juan, Jr. et al. |
| 2007/0270775 A1 | 11/2007 | Miller et al. |
| 2007/0293807 A1 | 12/2007 | Lynch et al. |
| 2007/0293872 A1 | 12/2007 | Peyman |
| 2007/0299459 A1 | 12/2007 | Way et al. |
| 2008/0015633 A1 | 1/2008 | Abbott et al. |
| 2008/0027304 A1 | 3/2008 | Erickson et al. |
| 2008/0057106 A1 | 3/2008 | Erickson et al. |
| 2008/0058717 A1 | 3/2008 | Spector |
| 2008/0108933 A1 | 5/2008 | Yu et al. |

(56) References Cited

U.S. PATENT DOCUMENTS

| | | |
|---|---|---|
| 2008/0147001 A1 | 6/2008 | Al-Marashi et al. |
| 2008/0181929 A1 | 7/2008 | Robinson et al. |
| 2008/0249467 A1 | 10/2008 | Burnett et al. |
| 2008/0281277 A1 | 11/2008 | Thyzel |
| 2008/0312661 A1 | 12/2008 | Downer et al. |
| 2009/0036818 A1 | 2/2009 | Grahn et al. |
| 2009/0043321 A1 | 2/2009 | Conston et al. |
| 2009/0082860 A1 | 3/2009 | Schieber et al. |
| 2009/0082862 A1 | 3/2009 | Schieber et al. |
| 2009/0099552 A1 | 4/2009 | Levy et al. |
| 2009/0099626 A1 | 4/2009 | de Juan, Jr. et al. |
| 2009/0104243 A1 | 4/2009 | Utkhede et al. |
| 2009/0124973 A1 | 5/2009 | D'Agostino et al. |
| 2009/0177138 A1 | 7/2009 | Brown et al. |
| 2009/0182421 A1 | 7/2009 | Silvestrini et al. |
| 2009/0209910 A1 | 8/2009 | Kugler et al. |
| 2009/0216106 A1 | 8/2009 | Takii |
| 2009/0264813 A1 | 10/2009 | Chang |
| 2009/0270890 A1 | 10/2009 | Robinson et al. |
| 2009/0281520 A1 | 11/2009 | Highley et al. |
| 2009/0287136 A1 | 11/2009 | Castillejos |
| 2010/0004581 A1 | 1/2010 | Brigatti et al. |
| 2010/0030146 A1 | 2/2010 | Kakish |
| 2010/0063478 A1 | 3/2010 | Selkee |
| 2010/0063512 A1 | 4/2010 | Robinson et al. |
| 2010/0098772 A1 | 4/2010 | Robinson et al. |
| 2010/0100104 A1 | 4/2010 | Yu et al. |
| 2010/0114006 A1 | 5/2010 | Baerveldt et al. |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0134759 A1 | 6/2010 | Silvestrini et al. |
| 2010/0137981 A1 | 6/2010 | Silvestrini et al. |
| 2010/0173866 A1 | 7/2010 | Hee et al. |
| 2010/0191103 A1 | 7/2010 | Stamper et al. |
| 2010/0191224 A1 | 7/2010 | Butcher |
| 2010/0217206 A1 | 8/2010 | Lum |
| 2010/0241046 A1 | 9/2010 | Pinchuk et al. |
| 2010/0249497 A1 | 9/2010 | Peine |
| 2010/0249691 A1 | 9/2010 | Van Der Mooren et al. |
| 2010/0312254 A1 | 12/2010 | Downer et al. |
| 2010/0328606 A1 | 12/2010 | Peyman |
| 2011/0009872 A1 | 1/2011 | Mistry et al. |
| 2011/0009874 A1 | 1/2011 | Wardle et al. |
| 2011/0046536 A1 | 2/2011 | Stegmann et al. |
| 2011/0098627 A1 | 4/2011 | Wilcox |
| 2011/0098809 A1 | 4/2011 | Wardle et al. |
| 2011/0105986 A1 | 5/2011 | Bronstein et al. |
| 2011/0105990 A1 | 5/2011 | Silvestrini |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0234976 A1 | 9/2011 | Kocaoglu et al. |
| 2011/0245753 A1 | 10/2011 | Sunalp |
| 2011/0319806 A1 | 12/2011 | Wardle |
| 2012/0078362 A1 | 3/2012 | Haffner et al. |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123433 A1 | 5/2012 | Horvath et al. |
| 2012/0123434 A1 | 5/2012 | Grabner et al. |
| 2012/0150129 A1 | 6/2012 | Jin |
| 2012/0165720 A1 | 6/2012 | Horvath et al. |
| 2012/0165933 A1 | 6/2012 | Haffner et al. |
| 2012/0197175 A1 | 8/2012 | Horvath et al. |
| 2012/0215241 A1 | 8/2012 | Trees et al. |
| 2012/0226150 A1 | 9/2012 | Balicki et al. |
| 2012/0310137 A1 | 12/2012 | Silvestrini |
| 2012/0323159 A1 | 12/2012 | Wardle et al. |
| 2013/0096483 A1 | 4/2013 | Dacquay |
| 2013/0150773 A1 | 6/2013 | Hertz et al. |
| 2013/0158462 A1 | 6/2013 | Wardle et al. |
| 2013/0158574 A1 | 6/2013 | Yi et al. |
| 2013/0184631 A1 | 7/2013 | Pinchuk |
| 2013/0211312 A1 | 8/2013 | Gelvin |
| 2013/0211314 A1 | 8/2013 | Boey et al. |
| 2013/0237958 A1 | 9/2013 | Arrigo |
| 2013/0245573 A1 | 9/2013 | de Juan, Jr. et al. |
| 2013/0253528 A1 | 9/2013 | Haffner et al. |
| 2013/0281817 A1 | 10/2013 | Schaller et al. |
| 2013/0281907 A1 | 10/2013 | Wardle et al. |
| 2013/0281908 A1 | 10/2013 | Schaller et al. |
| 2013/0289467 A1 | 10/2013 | Haffner et al. |
| 2013/0325024 A1 | 12/2013 | Nissan et al. |
| 2013/0345515 A1 | 12/2013 | Fitzmaurice et al. |
| 2014/0066833 A1 | 3/2014 | Yaron et al. |
| 2014/0081195 A1 | 3/2014 | Clauson et al. |
| 2014/0277429 A1 | 4/2014 | Kuzma et al. |
| 2014/0135916 A1 | 5/2014 | Clauson et al. |
| 2014/0163448 A1 | 6/2014 | Lind et al. |
| 2014/0213958 A1 | 7/2014 | Clauson et al. |
| 2014/0236066 A1 | 8/2014 | Horvath et al. |
| 2014/0243730 A1 | 8/2014 | Horvath et al. |
| 2014/0275923 A1 | 9/2014 | Haffner et al. |
| 2014/0276332 A1 | 9/2014 | Crimaldi et al. |
| 2014/0277349 A1 | 9/2014 | Vad |
| 2014/0303544 A1 | 10/2014 | Haffner et al. |
| 2014/0323995 A1 | 10/2014 | Clauson et al. |
| 2014/0343476 A1 | 11/2014 | Penhasi |
| 2014/0364789 A1 | 12/2014 | Schaller |
| 2014/0371651 A1 | 12/2014 | Pinchuk |
| 2015/0005689 A1 | 1/2015 | Horvath et al. |
| 2015/0011926 A1 | 1/2015 | Reitsamer et al. |
| 2015/0027866 A1 | 1/2015 | Morimoto et al. |
| 2015/0038893 A1 | 2/2015 | Haffner et al. |
| 2015/0133946 A1 | 5/2015 | Horvath et al. |
| 2015/0238687 A1 | 8/2015 | Novakovic |
| 2015/0265469 A1 | 9/2015 | Bhandari et al. |
| 2015/0290035 A1 | 10/2015 | Horvath et al. |
| 2015/0374545 A1 | 12/2015 | Horvath et al. |
| 2016/0038338 A1 | 2/2016 | Rangel-Friedman et al. |
| 2016/0089513 A1 | 3/2016 | Ishida |
| 2016/0101269 A1 | 4/2016 | Benz |
| 2016/0135993 A1 | 5/2016 | Horvath et al. |
| 2016/0135994 A1 | 5/2016 | Romoda et al. |
| 2016/0158063 A1 | 6/2016 | Romoda et al. |
| 2016/0249947 A1 | 9/2016 | Castanon et al. |
| 2016/0250071 A1 | 9/2016 | Horvath et al. |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0256321 A1 | 9/2016 | Horvath et al. |
| 2016/0256322 A1 | 9/2016 | Horvath et al. |
| 2016/0256323 A1 | 9/2016 | Horvath et al. |
| 2016/0278982 A1 | 9/2016 | Horvath et al. |
| 2016/0331902 A1 | 11/2016 | Carlyon |
| 2016/0354244 A1 | 12/2016 | Horvath et al. |
| 2016/0354245 A1 | 12/2016 | Horvath et al. |
| 2017/0086821 A1 | 3/2017 | Meade et al. |
| 2017/0172797 A1 | 6/2017 | Horvath et al. |
| 2017/0172798 A1 | 6/2017 | Horvath et al. |
| 2017/0172799 A1 | 6/2017 | Horvath et al. |
| 2017/0172800 A1 | 6/2017 | Romoda et al. |
| 2017/0348150 A1 | 12/2017 | Horvath et al. |
| 2018/0008464 A1 | 1/2018 | Horvath et al. |
| 2018/0199797 A1 | 7/2018 | London |
| 2019/0030285 A1 | 1/2019 | Prabhu |
| 2019/0054272 A1 | 2/2019 | Tal |
| 2019/0069770 A1 | 3/2019 | Bourget |
| 2019/0133826 A1 | 5/2019 | Horvath et al. |
| 2019/0240069 A1 | 8/2019 | Horvath et al. |
| 2019/0290314 A1 | 9/2019 | Gemer |
| 2020/0046213 A1 | 2/2020 | Bendory |
| 2020/0054353 A1 | 2/2020 | Yun |

FOREIGN PATENT DOCUMENTS

| | | |
|---|---|---|
| CN | 1909859 | 2/2007 |
| CN | 101677823 | 3/2010 |
| CN | 102170840 | 8/2011 |
| CN | 102481171 | 5/2012 |
| CN | 102510746 | 6/2012 |
| CN | 103313751 A | 9/2013 |

(56) References Cited

FOREIGN PATENT DOCUMENTS

| | | | |
|---|---|---|---|
| CN | 105899170 A | 8/2016 |
| CN | 106999294 A | 8/2017 |
| GB | 2296663 | 7/1996 |
| JP | 2012-527318 | 6/1998 |
| JP | 2014-500758 | 9/2000 |
| JP | 2007181604 A | 7/2007 |
| JP | 2009-523540 | 12/2007 |
| JP | 2012030128 A | 2/2012 |
| JP | 2012529350 A | 11/2012 |
| JP | 2012-532692 | 12/2012 |
| JP | WO2013137208 A1 | 9/2013 |
| JP | 2015110017 A | 6/2015 |
| JP | 2015157051 A | 9/2015 |
| JP | 2017104737 A | 6/2017 |
| JP | 2017140494 A | 8/2017 |
| RU | 2313315 C2 | 12/2007 |
| RU | 2482822 | 5/2013 |
| WO | WO 98/23237 | 6/1998 |
| WO | WO1998023237 A1 | 6/1998 |
| WO | WO 00/056255 | 9/2000 |
| WO | WO2000056255 A1 | 9/2000 |
| WO | WO 01/50943 | 7/2001 |
| WO | WO2001050943 A2 | 7/2001 |
| WO | WO 02/74052 | 9/2002 |
| WO | WO2002074052 A2 | 9/2002 |
| WO | WO 2007/087061 | 8/2007 |
| WO | WO2007087061 A3 | 8/2007 |
| WO | WO 2008/005873 | 1/2008 |
| WO | WO2008005873 A2 | 1/2008 |
| WO | WO 2010/003011 | 12/2011 |
| WO | WO 2011/155922 | 12/2011 |
| WO | WO 2013/151904 | 10/2013 |
| WO | WO2013151904 A1 | 10/2013 |
| WO | WO 2014/150292 | 9/2014 |
| WO | WO2015000943 A2 | 1/2015 |
| WO | WO 2016/023942 | 2/2016 |
| WO | WO 2016/159999 | 10/2016 |
| WO | WO 2016/196841 | 12/2016 |
| WO | WO 2017/040855 | 3/2017 |
| WO | WO 2017/184881 | 10/2017 |
| WO | WO2017184881 A1 | 10/2017 |

OTHER PUBLICATIONS

Pediatric Surgery, vol. E, 7th edition, published on Feb. 14, 2012 to Coran et al.

QUERE, "Fluid Coating on a Fiber," Annu. Rev. Fluid Mech. 1999, 31:347-84.

* cited by examiner

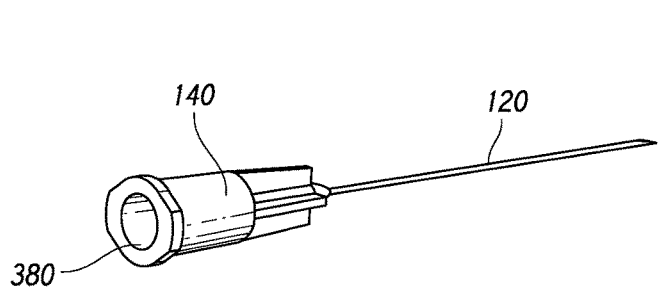
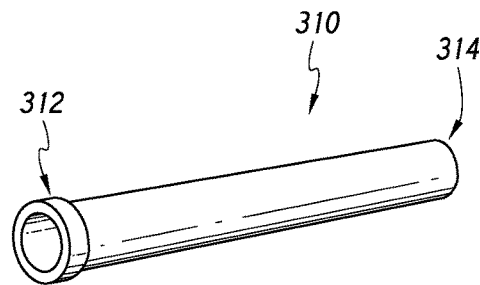
FIG. 7   FIG. 10
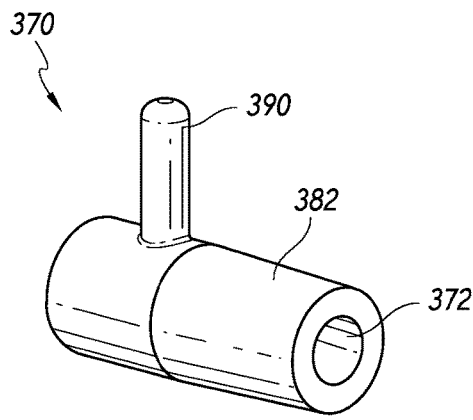
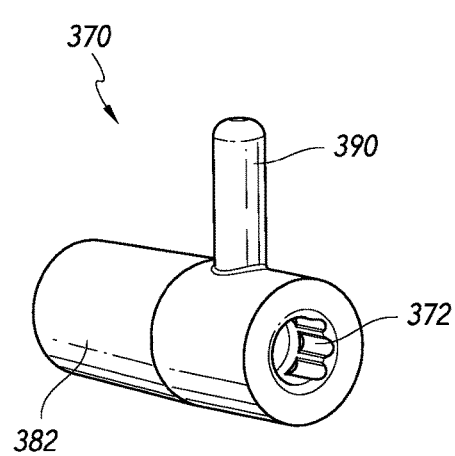
FIG. 8A   FIG. 8B
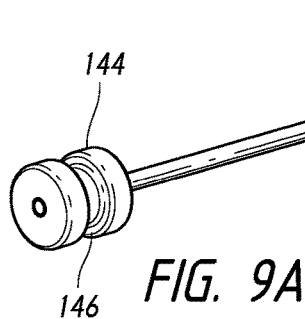
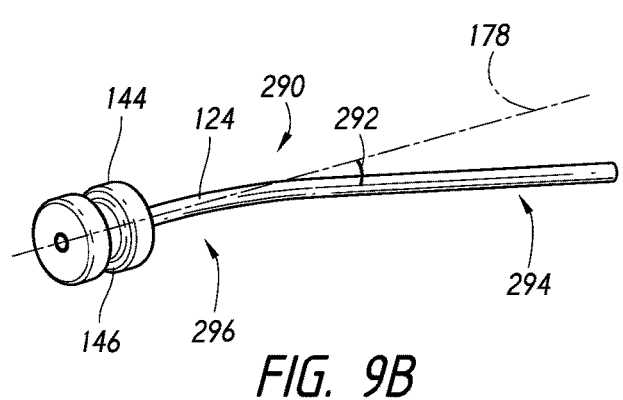
FIG. 9A   FIG. 9B

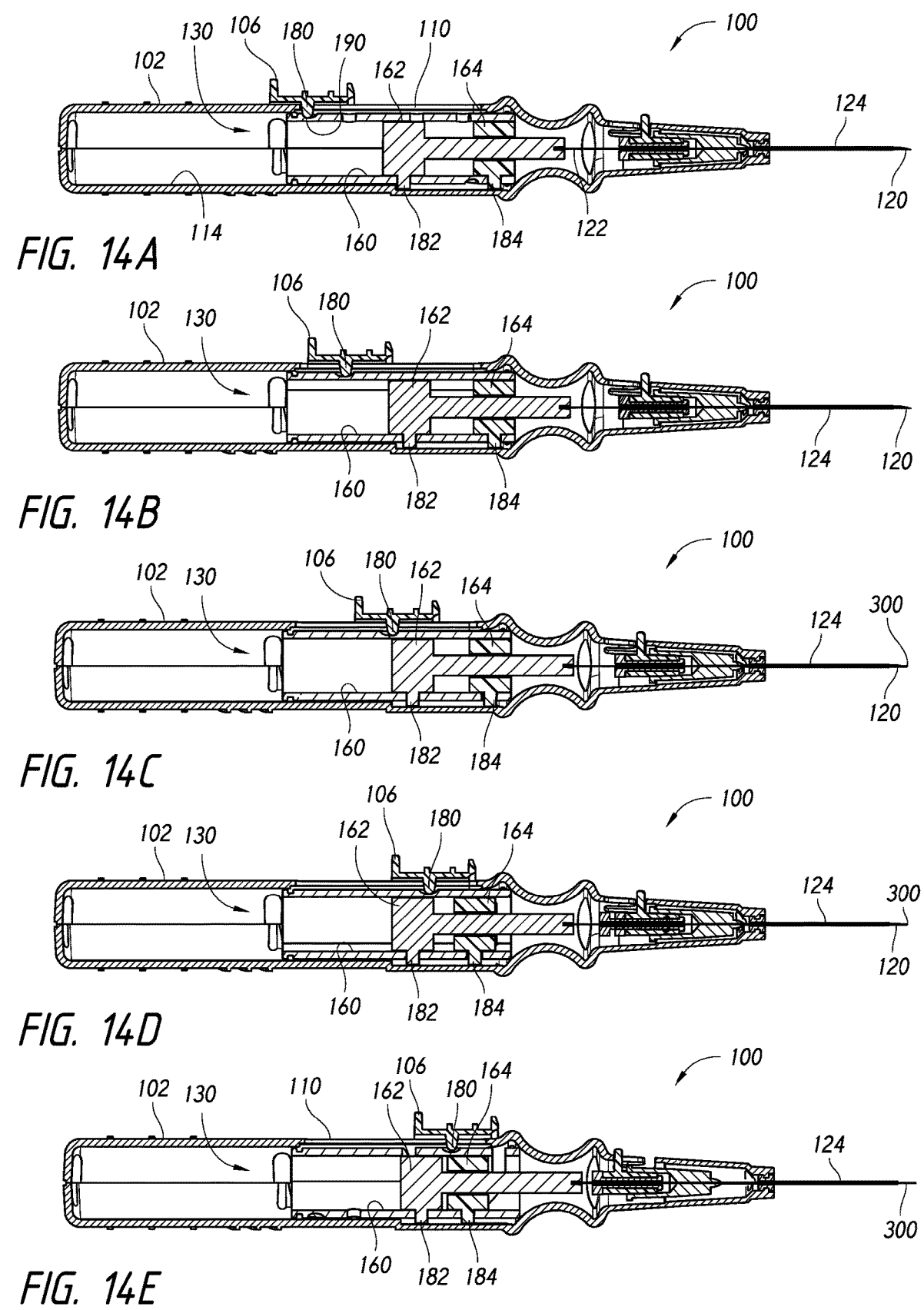

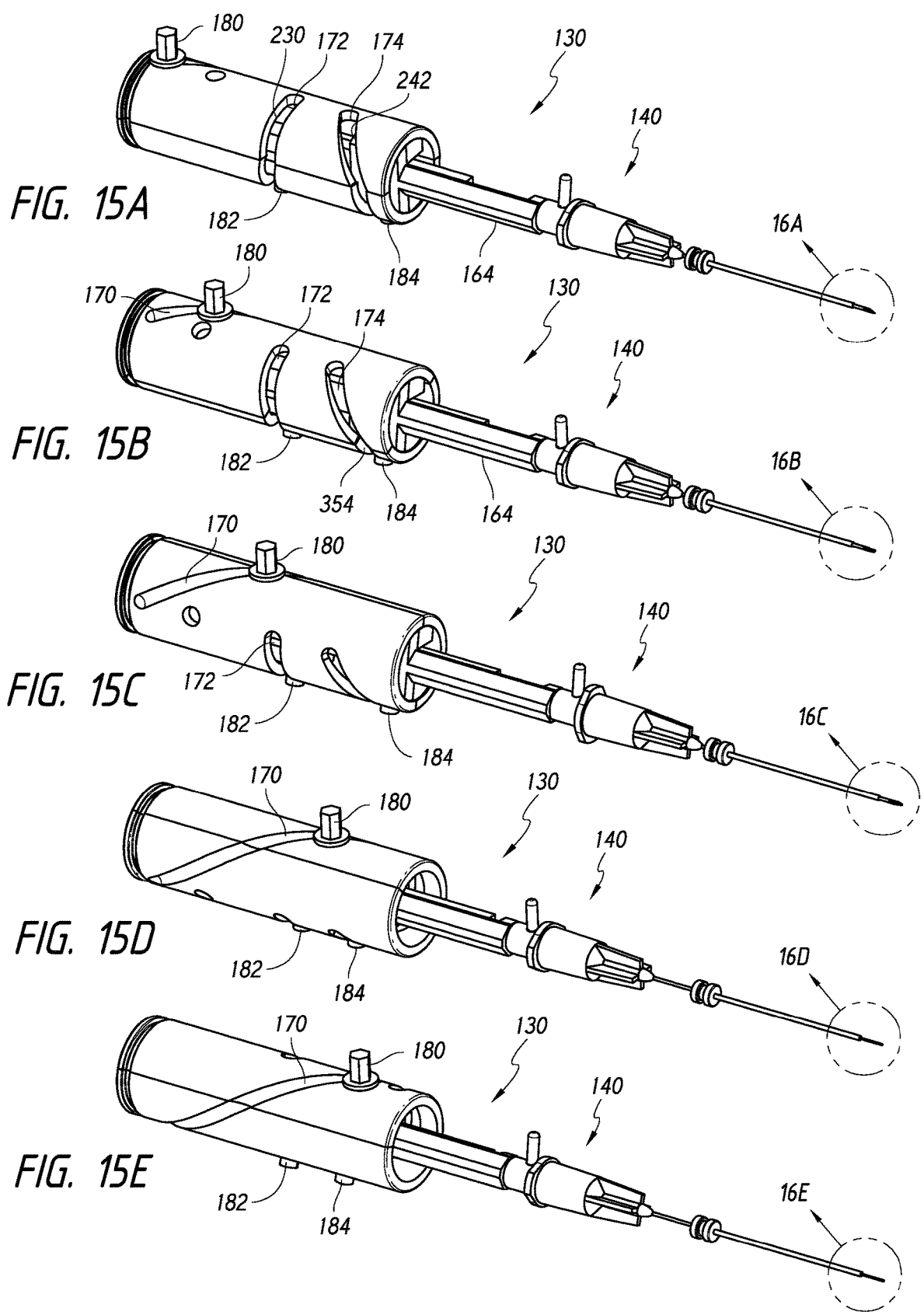

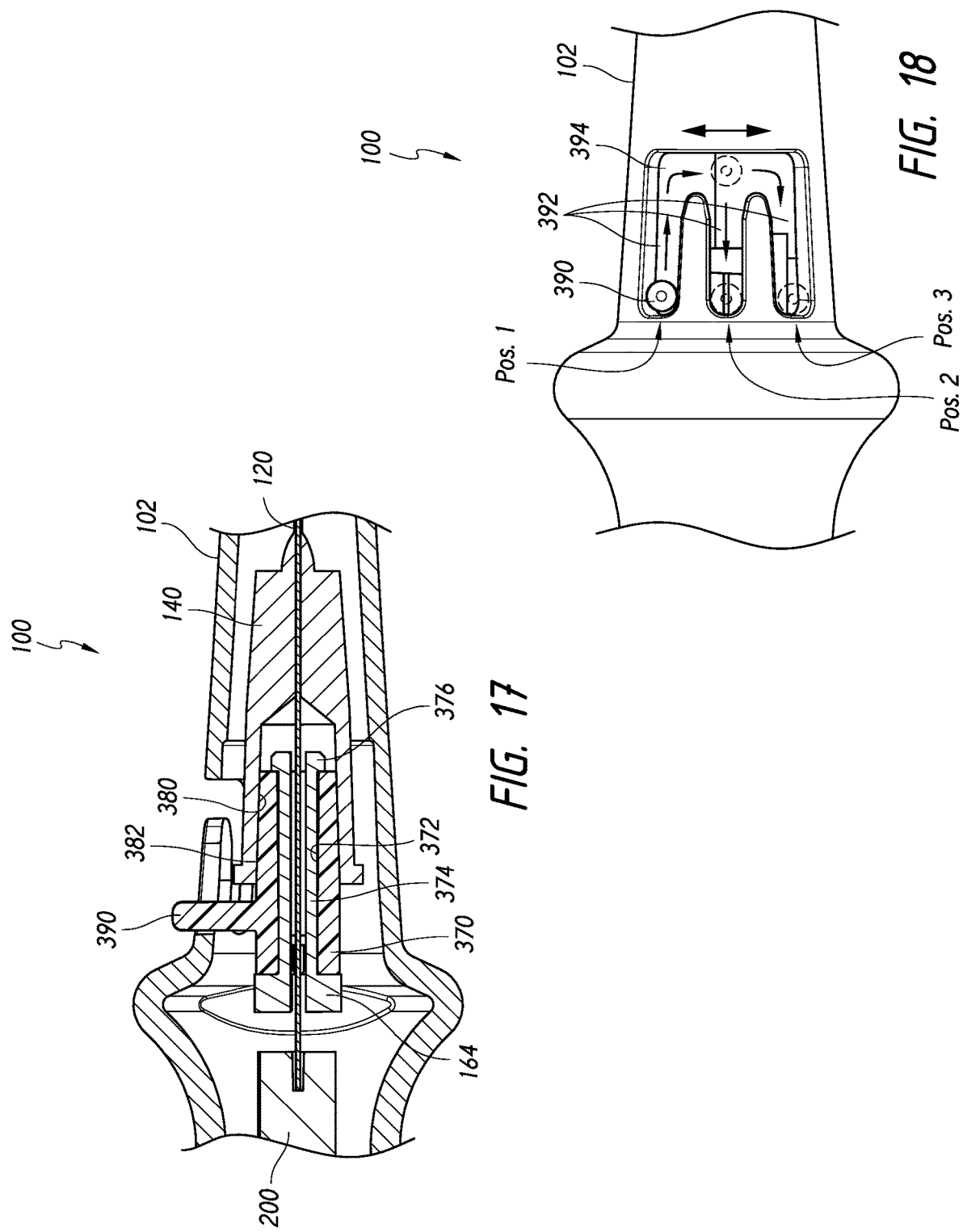

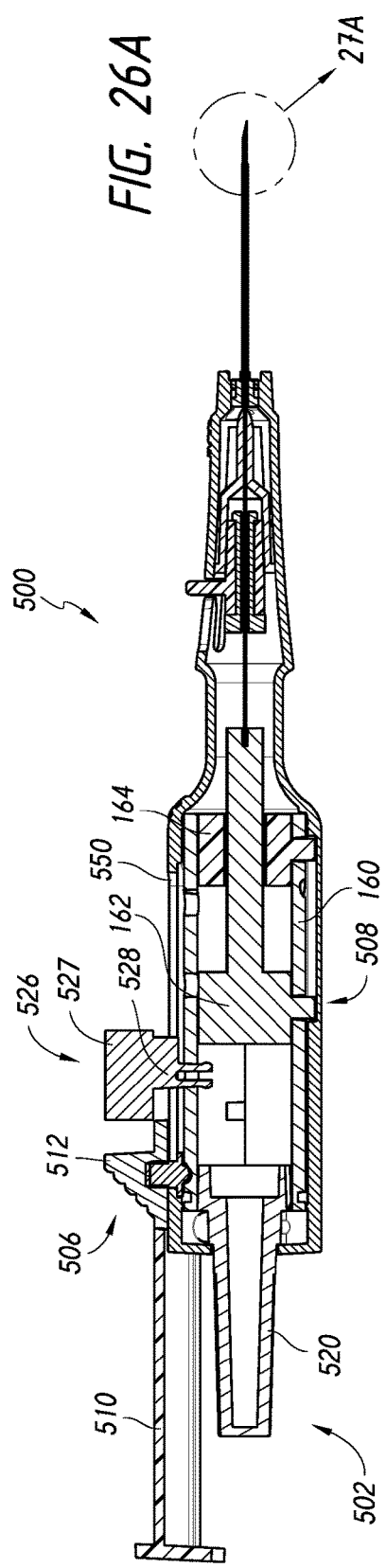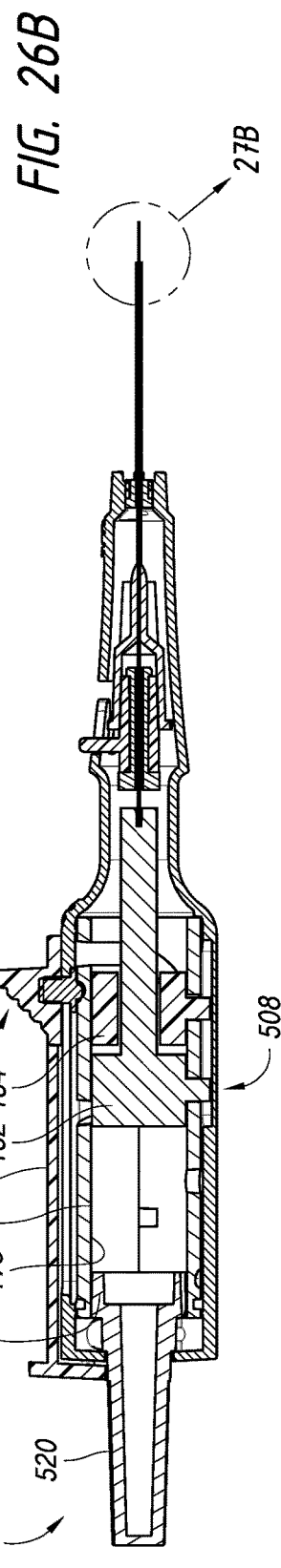

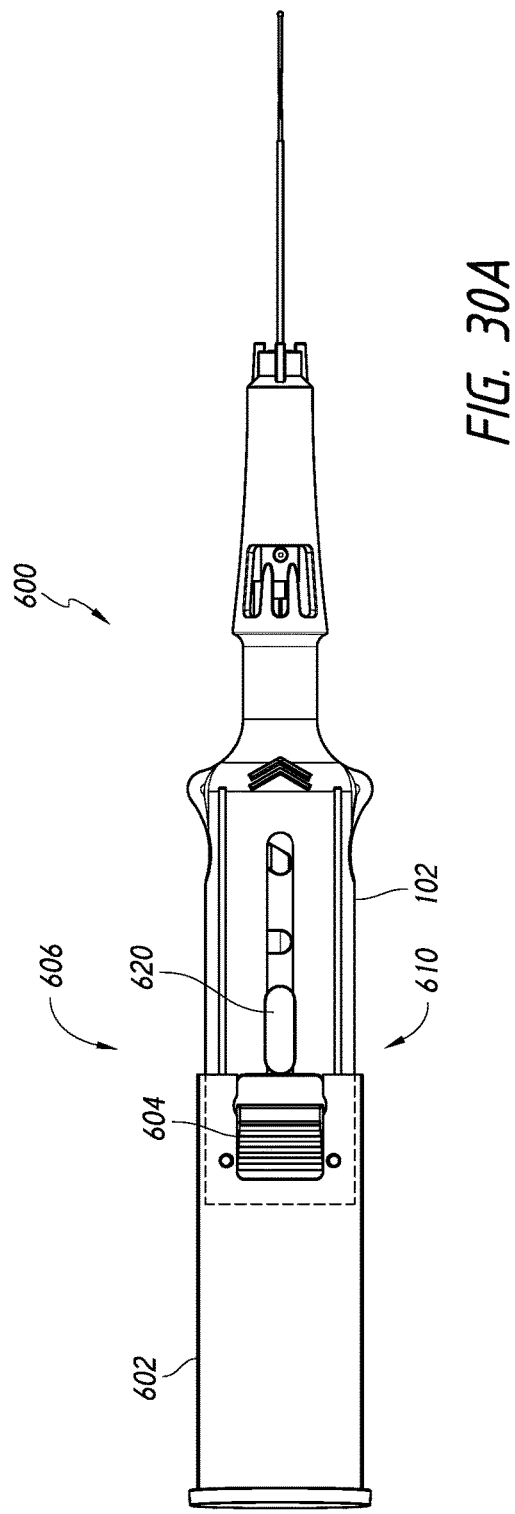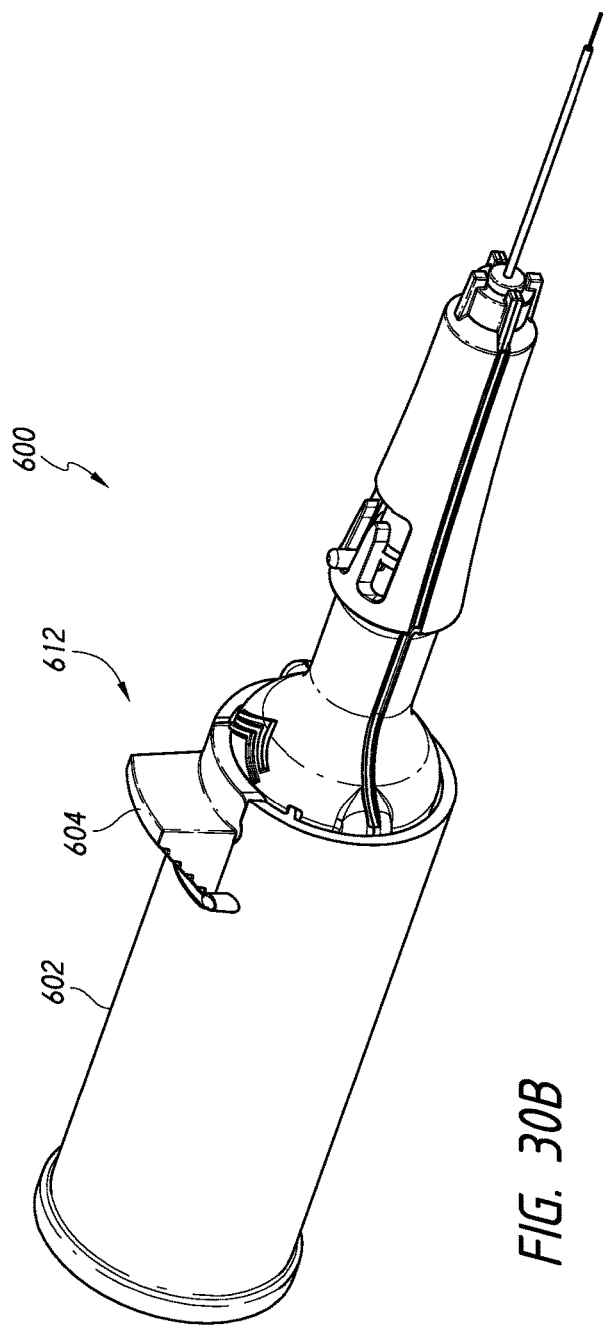

INTRAOCULAR SHUNT INSERTION TECHNIQUES

CROSS-REFERENCE TO RELATED APPLICATIONS

This application is a continuation of U.S. patent application Ser. No. 15/451,274, filed on Mar. 6, 2017, now U.S. Pat. No. 10,653,555, which is a continuation of U.S. patent application Ser. No. 14/541,070, filed on Nov. 13, 2014, now U.S. Pat. No. 9,585,790, which claims the benefit of U.S. Provisional Application No. 61/904,429, filed Nov. 14, 2013, the entirety of each of which is incorporated herein by reference.

BACKGROUND

Field of the Inventions

The present disclosure generally relates to devices and methods of implanting an intraocular shunt into an eye.

Description of the Related Art

Glaucoma is a disease in which the optic nerve is damaged, leading to progressive, irreversible loss of vision. It is typically associated with increased pressure of the fluid (i.e., aqueous humor) in the eye. Untreated glaucoma leads to permanent damage of the optic nerve and resultant visual field loss, which can progress to blindness. Once lost, this damaged visual field cannot be recovered. Glaucoma is the second leading cause of blindness in the world, affecting 1 in 200 people under the age of fifty, and 1 in 10 over the age of eighty for a total of approximately 70 million people worldwide.

The importance of lowering intraocular pressure (IOP) in delaying glaucomatous progression has been well documented. When drug therapy fails, or is not tolerated, surgical intervention is warranted. Surgical filtration methods for lowering intraocular pressure by creating a fluid flow path between the anterior chamber and an area of lower pressure have been described. Intraocular shunts can be positioned in the eye to drain fluid from the anterior chamber to locations such as the sub-Tenon's space, the subconjunctival space, the episcleral vein, the suprachoroidal space, Schlemm's canal, and the intrascleral space.

Positioning of an intraocular shunt to drain fluid into the intrascleral space is promising because it avoids contact with the conjunctiva and the suprachoroidal space. Avoiding contact with the conjunctiva and choroid is important because it reduces irritation, inflammation and tissue reaction that can lead to fibrosis and reduce the outflow potential of the subconjunctival and suprachoroidal space. The conjunctiva itself plays a critical role in glaucoma filtration surgery. A less irritated and healthy conjunctiva allows drainage channels to form and less opportunity for inflammation and scar tissue formation. intrascleral shunt placement safeguards the integrity of the conjunctiva and choroid, but may provide only limited outflow pathways that may affect the long term TOP lowering efficacy.

SUMMARY

According to some embodiments, methods and devices are provided for positioning an intraocular shunt within the eye to treat glaucoma. Various methods are disclosed herein which allow an operator to access a variety of locations within the eye, including the subconjunctival space, the intrascleral space, the supraciliary space, the suprachoroidal space, and the intra-Tenon's adhesion space.

For example, a method of treating glaucoma is disclosed that can comprise inserting an intraocular shunt into eye tissue such that an inflow end of the shunt is positioned in the anterior chamber of the eye and an outflow end of the shunt is positioned between layers of Tenon's capsule.

In accordance with some embodiments, the shunt can be introduced into the eye through the cornea. After introducing the shunt through the cornea, the shunt can be advanced into the sclera. For example, the shunt can be advanced into the sclera through the anterior chamber angle tissue.

In some embodiments, an inserter for treating glaucoma can comprise: a housing having a distal portion, a proximal portion, a longitudinal axis extending between the distal and proximal portions, an interior cavity, and an elongate slot extending along an outer surface of the housing into the cavity; a needle, having a lumen, movably coupled to the distal portion along the axis; a plunger, disposed within the lumen, movable along the axis to result in an axial force on a shunt to urge the shunt distally relative to the needle; and a slider component coupled to the housing and slidable along the elongate slot, the slider component being engaged with the drive component such that distal movement of the slider component along the axis results in both (1) distal movement of the plunger along the axis and (2) after distal movement of the plunger, proximal movement of the needle along the axis.

In some embodiments, an inserter for treating glaucoma can comprise: a housing having a longitudinal axis and an elongate slot extending substantially parallel relative to the axis over a length of less than 5 inches; a needle, having a lumen, movably coupled to the housing; a plunger, disposed within the lumen, movably coupled to the housing; and a slider component coupled to the needle and the plunger and slidable along the slot to result in both (1) distal movement of the plunger along the axis relative to the housing and (2) proximal movement of the needle along the axis relative to the housing.

Further, in some embodiments, an inserter for treating glaucoma can comprise: a needle having a lumen; a plunger, movable within the lumen; a drive component coupled to the needle and the plunger to result in movement to the needle and the plunger along a longitudinal axis of the inserter upon rotation of the drive component; and a slider component coupled to the housing and slidable along an elongate groove such that movement of the slider component along the axis rotates the drive component within the housing and results in movement of the needle and the plunger along the axis.

Additionally, in some embodiments, an inserter for treating glaucoma can comprise: a housing having a distal portion and a longitudinal axis; a needle assembly, coupled to the housing distal portion, comprising a rotational adjustment component and a needle coupled to the adjustment component, wherein the adjustment component is rotatable to adjust a rotational alignment of the needle relative to the housing; and a plunger, movable within the lumen to result in an axial force on a shunt disposed within the lumen, to urge the shunt distally relative to the needle.

Further, in some embodiments, a drive component for actuating an inserter for treating glaucoma can comprise a cylindrical body having first, second, and third elongate tracks extending along the body, wherein the first elongate track extends helically from a proximal portion toward a distal portion of the body, the second elongate track having (1) a first portion, extending helically about the body, and (2) a second portion, extending circumferentially about the body, the third elongate track having (i) a first portion, extending circumferentially about the body, and (ii) a second portion, extending helically about the body.

Furthermore, in some embodiments, a method of manufacturing the drive component can comprise forming a first of the two pieces with a first portion of the first track and forming a second of the two pieces with a second portion of the first track, the first and second portions of the first track being alignable to assemble the first track when the first and second pieces are coupled together.

Some embodiments also provide a shunt retention device that comprises: an elongate, tubular body having first and second portions, the first portion having a taper such that the first portion can be inserted into a lumen of a needle to provide a precision press fit into the needle lumen, the second portion being graspable by an operator to facilitate insertion or withdrawal of the first portion relative to the needle lumen.

In some embodiments, an inserter for treating glaucoma can comprise: a housing having a distal portion, an outer surface, and an elongate slot extending along the outer surface; a needle, having a lumen, coupled to the housing distal portion; a plunger, disposed within the lumen, movable to result in an axial force on a shunt to urge the shunt distally relative to the needle; a slider component coupled to the housing and slidable along the elongate slot, the slider component being configured to result in an axial force on at least one of the plunger or the needle; and a grip section disposed proximally relative to the slider component, the grip section having first and second portions, wherein the first portion extends radially outward for providing resistance against distal movement of an operator's hand relative to the housing, and the second portion extends radially outward for providing resistance against proximal movement of an operator's hand relative to the housing.

Further, some embodiments can comprise a method of treating an eye. The method can comprise: introducing a needle into the eye through a cornea of the eye; advancing a bevel of the needle to a location intermediate a superficial layer and a deep layer; and rotating the bevel to create a space between the superficial layer and the deep layer.

In some embodiments, a method of treating an eye can also comprise: introducing a needle into the eye through a cornea of the eye; advancing a bevel of the needle to a location intermediate a superficial layer and a deep layer; and injecting a fluid from bevel to create a space between the superficial layer and the deep layer.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIG. 7 is a perspective view of a needle mount of the drive assembly shown in FIG. 3, according to some embodiments.

FIGS. 8A and 8B are perspective views of a rotation adjustment component of the drive assembly shown in FIG. 3, according to some embodiments.

FIG. 9A is a perspective view of a sleeve mount of the drive assembly shown in FIG. 3, having a straight needle component coupled thereto, according to some embodiments.

FIG. 9B is a perspective view of a sleeve mount of the drive assembly shown in FIG. 3, having a curved needle component coupled thereto, according to some embodiments.

FIG. 10 is a perspective view of a cap component for use with an inserter, according to some embodiments.

FIGS. 14A-14E are side, cross-sectional views of the inserter shown in FIG. 1B, illustrating stages of motion of the drive assembly, according to some embodiments.

FIGS. 15A-15E are perspective views of the drive assembly shown in FIG. 3, illustrating stages of motion of the drive assembly, according to some embodiments.

FIG. 17 is a side, cross-sectional view of a rotational adjustment mechanism of the inserter shown in FIG. 1B, according to some embodiments.

FIG. 18 is a top view of the rotational adjustment mechanism shown in FIG. 17, according to some embodiments.

FIGS. 26A and 26B are side, cross-sectional views of the inserter of FIG. 24, illustrating stages of motion of a drive assembly thereof, according to some embodiments.

FIGS. 27A and 27B are side, cross-sectional views of a needle, sleeve, and plunger of the inserter of FIG. 24, illustrating stages of motion corresponding to the ocean illustrated in FIGS. 26A and 26B, according to some embodiments.

FIGS. 30A and 30B are top and perspective views of yet another inserter, illustrating stages of motion of the handle component thereof, according to some embodiments.

DETAILED DESCRIPTION

Figure 1A:
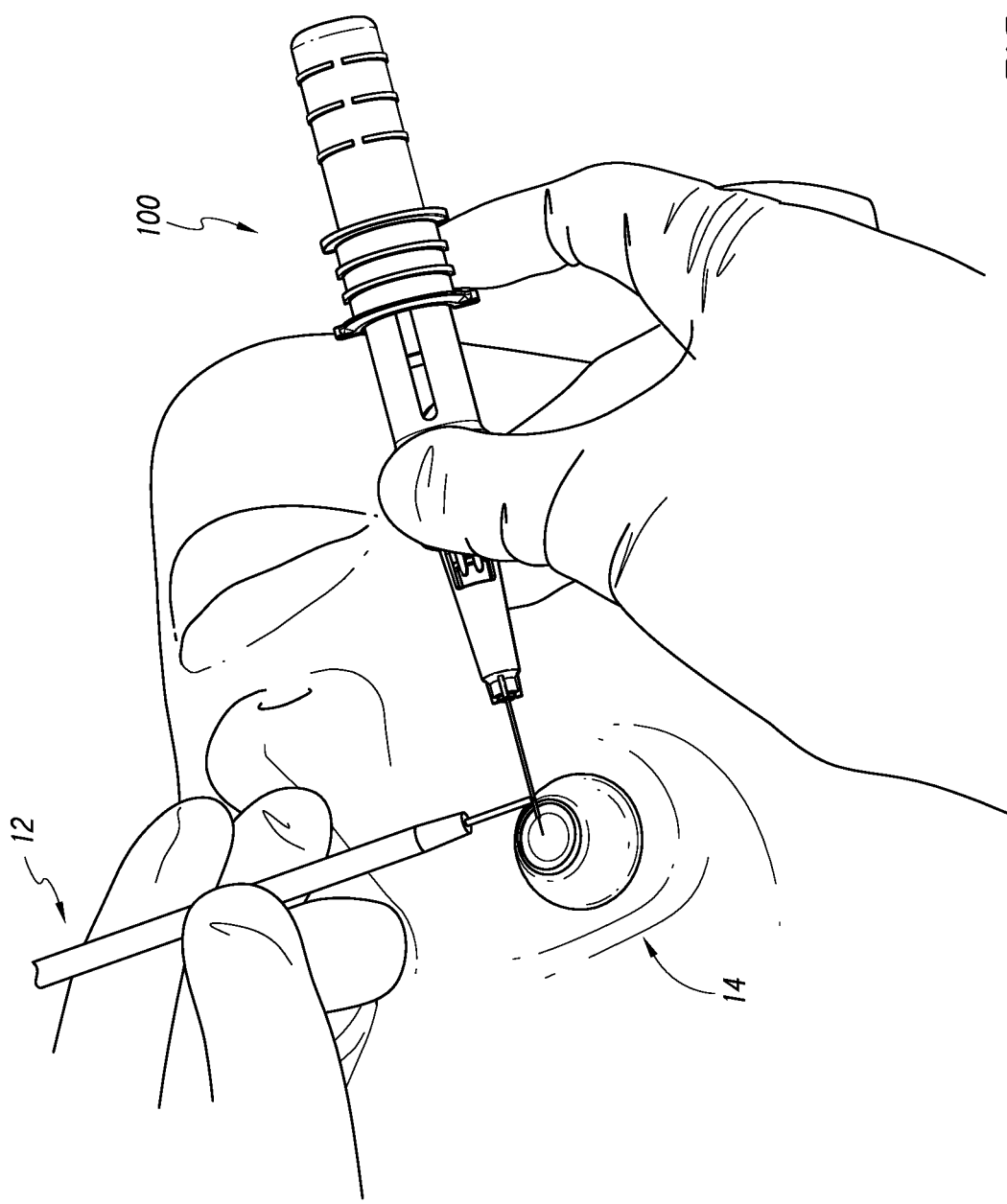
FIG. 1A is a schematic view of a procedure for implanting an intraocular shunt into an eye using an inserter, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments may be disclosed or shown in the context of ab interno procedures, such embodiments can be used in ab externo procedures. Furthermore, various applications of such embodiments and modifications thereto, which may occur to those who are skilled in the art, are also encompassed by the general concepts described herein.

Glaucoma is a disease in which the optic nerve is damaged, leading to progressive, irreversible loss of vision. It is typically associated with increased pressure of the fluid (i.e., aqueous humor) in the eye. Untreated glaucoma leads to permanent damage of the optic nerve and resultant visual field loss, which can progress to blindness. Once lost, this damaged visual field cannot be recovered.

In conditions of glaucoma, the pressure of the aqueous humor in the eye (anterior chamber) increases and this resultant increase of pressure can cause damage to the vascular system at the back of the eye and especially to the optic nerve. The treatment of glaucoma and other diseases that lead to elevated pressure in the anterior chamber involves relieving pressure within the anterior chamber to a normal level.

Glaucoma filtration surgery is a surgical procedure typically used to treat glaucoma. The procedure involves placing a shunt in the eye to relieve intraocular pressure by creating a pathway for draining aqueous humor from the anterior chamber of the eye. The shunt is typically positioned in the eye such that it creates a drainage pathway between the anterior chamber of the eye and a region of lower pressure. Various structures and/or regions of the eye having lower pressure that have been targeted for aqueous humor drainage include Schlemm's canal, the subconjunctival space, the episcleral vein, the suprachoroidal space, or the subarachnoid space. Methods of implanting intraocular shunts are known in the art. Shunts may be implanted using an ab externo approach (entering through the conjunctiva and inwards through the sclera) or an ab interno approach (entering through the cornea, across the anterior chamber, through the trabecular meshwork and sclera).

Embodiments of the present inventions are discussed below with reference to various illustrations which are intended to illustrate, but not to limit, the embodiments of the present inventions. In addition to the various features and embodiments discussed herein, various methods of operating these embodiments can also be provided. These methods are shown and illustrated in many of the images and figures included herewith.

The present disclosure relates to several inventions and embodiments of device concepts for an intraocular shunt inserter used in eye surgery. Some embodiments of the inserter can be designed to be used with the AqueSys XEN™ implant. The inserter can be made out of injection molded plastic to be a low cost disposable device. The shunt can be preloaded into the inserter.

One-Handed Inserter Designs

In accordance with some embodiments disclosed herein, the inserter can function as a one-handed device in order to allow an operator to keep her other hand on a fixation device that holds the eye, such as a hook. This can improve surgical control and placement accuracy and makes the surgery easier as well. An illustration of a procedure for treating an eye 12 is shown in FIG. 1A. FIG. 1A illustrates the use of a hook 14 for holding the eye 12 and an inserter 100 for introducing an intraocular shunt into the eye.

Figure 1B:
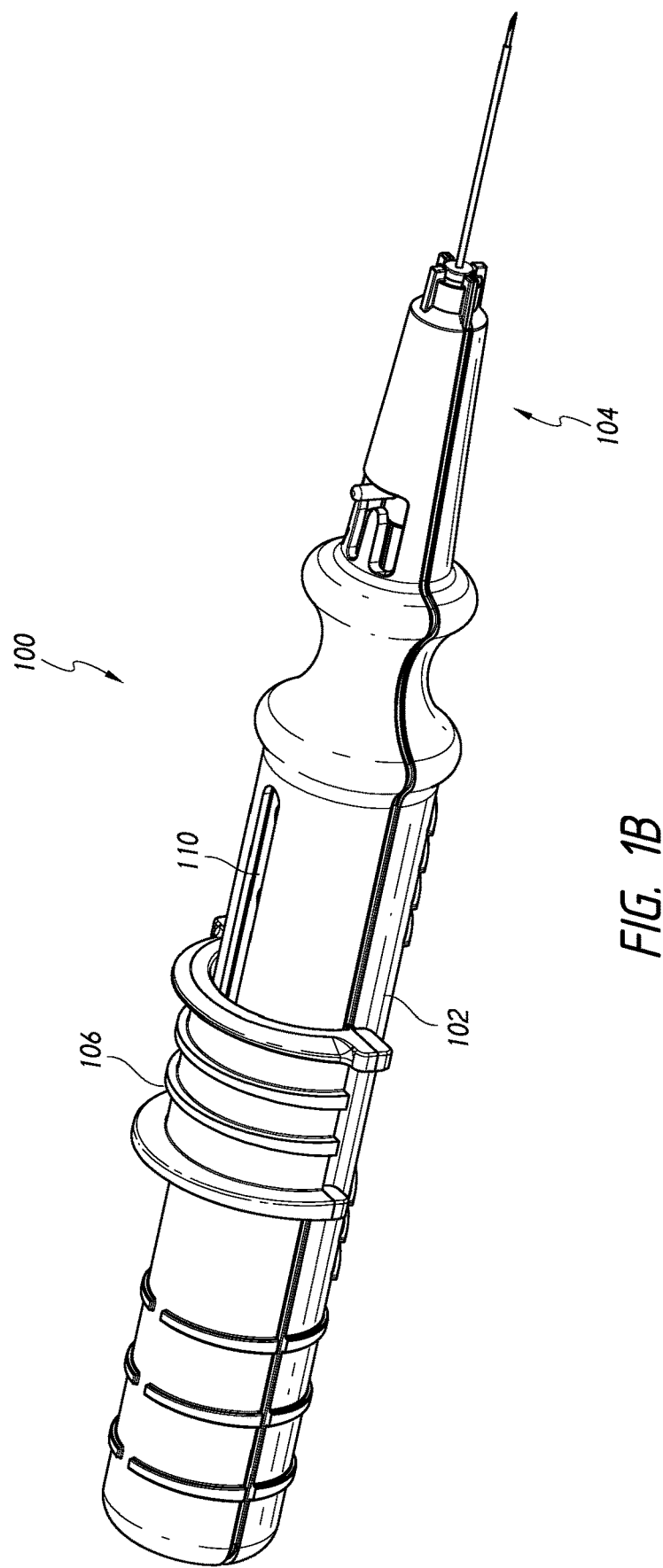
FIG. 1B is a perspective view of an inserter for implanting an intraocular shunt into an eye, according to some embodiments.

FIGS. 1B-19C illustrate further details of the inserter 100 shown in FIG. 1A. The inserter 100 can be actuated using a single hand, thus facilitating use of the inserter by an operator. The inserter 100 can comprise a housing 102, a needle assembly 104, and a slider component 106. As shown in FIG. 1B, the inserter 100 can be configured such that the slider component 106 is coupled to the housing 102 and slidable along an elongate slot 110 of the housing 102. The slider component 106 can be selectively movable by an operator in order to actuate movement of components of the needle assembly 104.

For example, when the slider component 106 moves distally along the slot 110 (i.e., in a direction toward the needle assembly 104), the slider component 106 can result in or cause a shunt (not shown) to be advanced within the needle assembly 104, and in some embodiments, released from the needle assembly 104. In accordance with some embodiments discussed further herein, movement of the slider component 106 can result in movement of components of the needle assembly 104. The sliding movement of the slider component 106 can be converted into rotational movement, which can thereafter be converted to movement along a longitudinal axis of the inserter 100. One of the pretzel benefits of this innovative and complex movement conversion mechanism is that it enables embodiments of the inserter to provide precise, measured movements of its components within a compact assembly.

Figure 2:
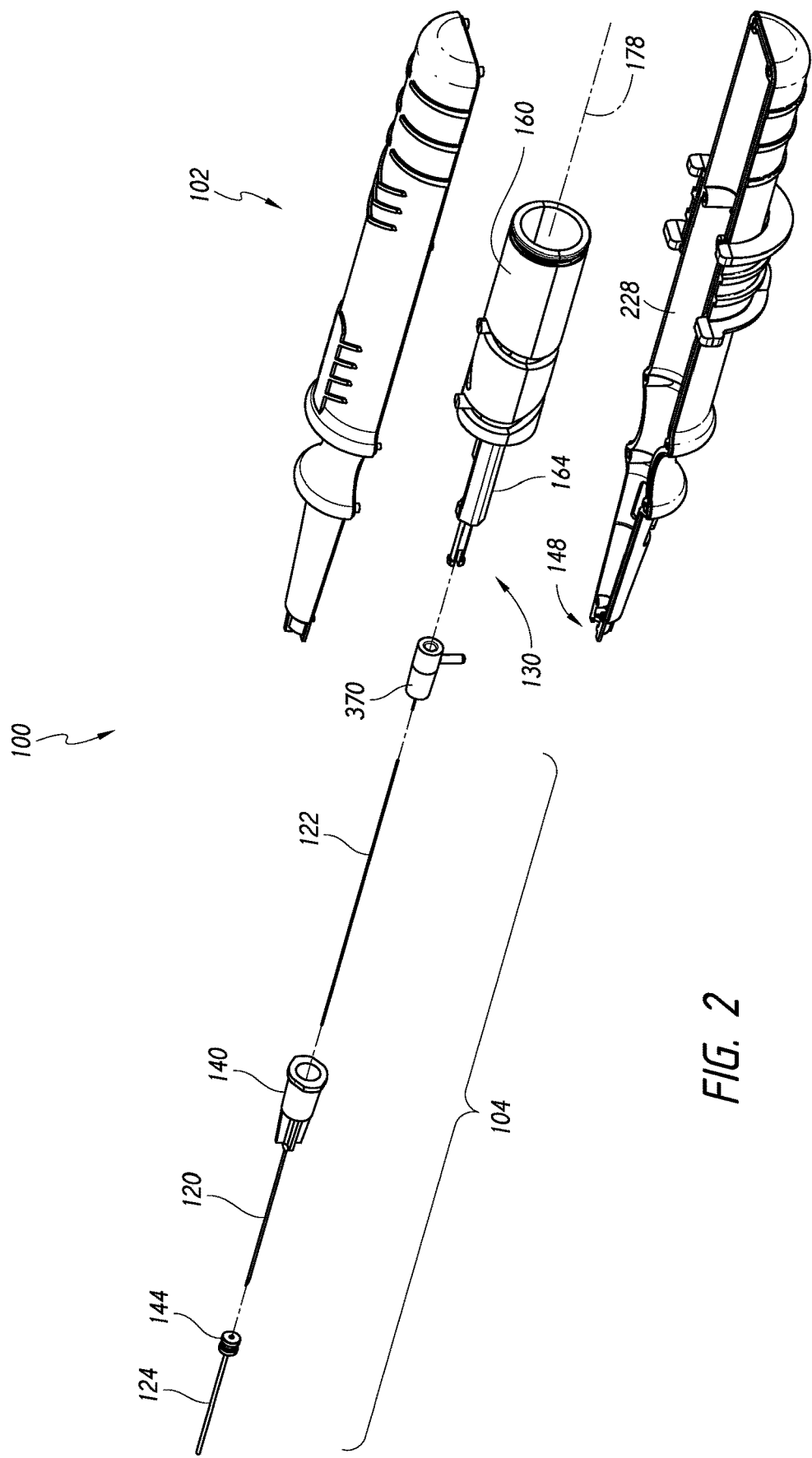
FIG. 2 is a perspective, exploded view of the inserter shown in FIG. 1B, according to some embodiments.

As illustrated in FIG. 2, the needle assembly 104 can comprise a needle component 120, a plunger 122, and a sleeve component 124. The needle component 120 can comprise a 25 or 27GA needle. The plunger 122 can be slidably movable within a lumen of the needle component 120 along a longitudinal axis 178 of the inserter 100. Further, the needle component 120 can be slidably movable within a lumen of the sleeve component 124 along the longitudinal axis 178. Each of the needle component 120 and the plunger 122 can be coupled to respective drive components of a drive assembly 130 disposed within the housing 102. When in the assembled state, the inserter 100 can be configured such that the needle component 120, the plunger 122, and the sleeve component 124 are aligned along or coaxial with the longitudinal axis 178. Some drive assemblies for actuating a plunger and for withdrawing a needle of an inserter are disclosed in copending U.S. patent application Ser. Nos. 13/336,803, 12/946,645, 12/620,564, 12/946,653, 12/946,565, and 11/771,805, the entireties of which are incorporated herein by reference.

Figure 3:
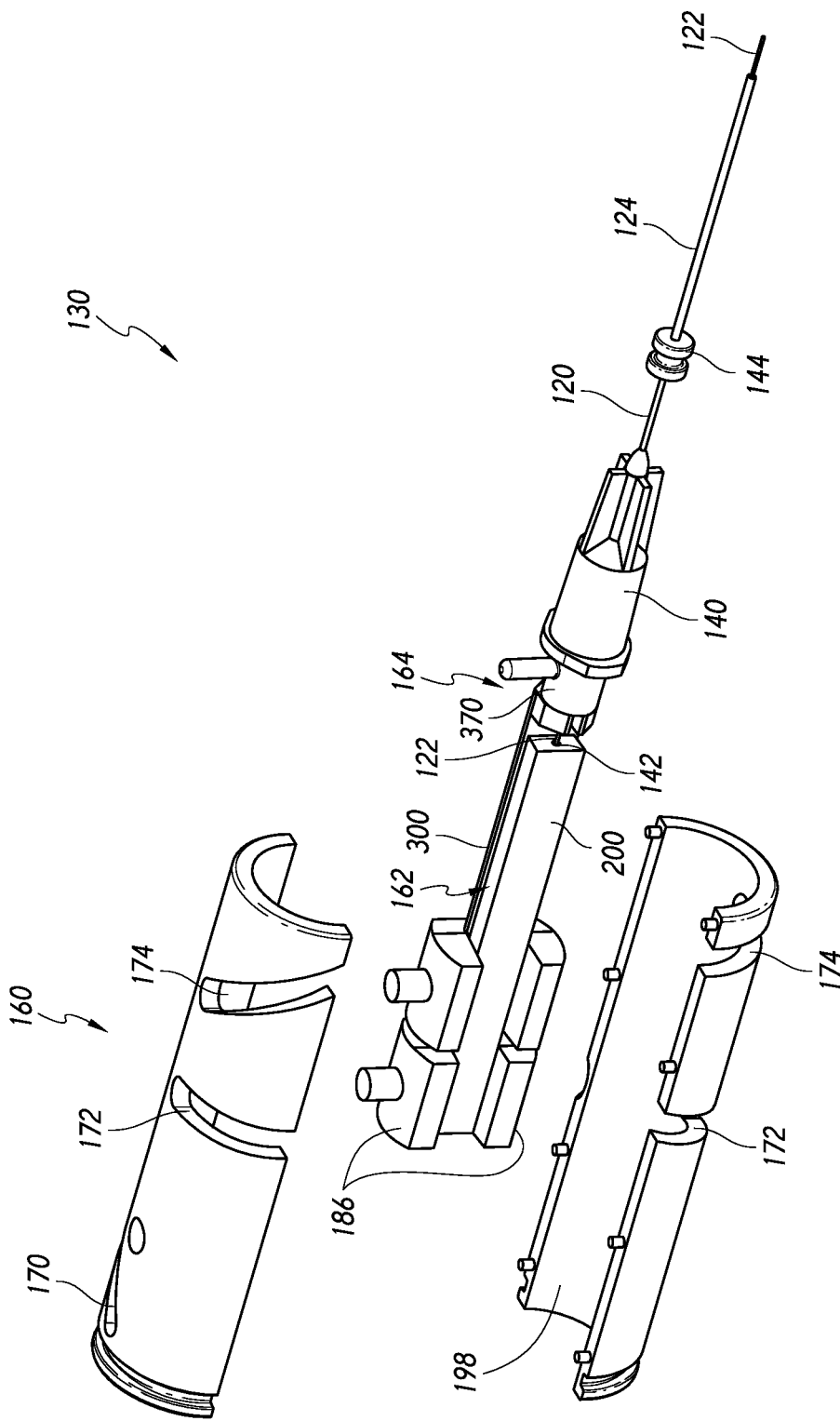
FIG. 3 is a perspective, exploded view of a drive assembly of the inserter shown in FIG. 1B, according to some embodiments.

Referring to FIGS. 2-3, the needle component 120, the plunger 122, and the sleeve component 124 can be operably coupled to the drive assembly 130 and/or the housing 102. For example, the needle component 120 can be coupled to a needle mount 140. The needle mount 140, shown in FIGS. 2-3 and 7, can be fixedly coupled to a proximal end portion of the needle component 120 such that rotational and longitudinal movement between the needle component 120 and the needle mount 140 is restricted or prevented. The needle mount 140 can be enclosed within a distal end portion of the housing 102 when the inserter 100 is assembled. Further, as illustrated in FIG. 3 and discussed further below, the needle mount 140 can be coupled to a needle driver 164 (and in the illustrated embodiment, via a rotational adjustment component 370) of the drive assembly 130.

Further, as shown in FIG. 3, the plunger 122 can be coupled to a plunger mount 142. The plunger mount 142, shown in FIGS. 3, 5A, and 5B, can be fixedly coupled to a proximal end portion or midsection of the plunger 122 to restrict or prevent rotational and longitudinal movement of the plunger 122 relative to the plunger mount 142. Further, as illustrated in FIG. 3 and discussed further below, the plunger mount 142 can be coupled to a plunger driver 162 of the drive assembly 130.

Furthermore, the sleeve component 124 can be coupled to a sleeve mount 144. The sleeve mount 144, shown in FIGS. 2-3 and 9, can be coupled to a proximal end portion of the sleeve component 124 so as to prevent rotational and longitudinal movement between the sleeve component 124 and the sleeve mount 144. The sleeve mount 144 can be coupled to a portion 148 of the housing 102, as discussed below.

As noted above, the needle component 120, the plunger 122, and the sleeve component 124 can be operably coupled to the drive assembly 130 and/or the housing 102. Such coupling can occur via the needle mount 140, the plunger mount 142, and the sleeve mount 144. In turn, the needle mount 140, the plunger mount 142, and the sleeve mount 144 can be coupled to one or more drive components that engage with the drive assembly 134 to the housing 102.

In accordance with some embodiments, the drive assembly 130 can be coupled to the needle component 120 and the plunger 122 to actuate movement along the longitudinal axis 178 of the needle component 120 and the plunger 122 relative to the housing 102. For example, the drive assembly 130 can be configured to rotate or slide within the housing 102. The drive assembly 130 can transfer a longitudinal or axial force along the longitudinal axis 178 to the needle component 120 and/or the plunger 122, independently or at the same time, to result in movement of the needle component 120 and the plunger 122 relative to the housing 102 along the longitudinal axis 178.

As discussed herein, motion of the slider component 106 can result in motion of the drive assembly 130 and thereby result in motion of components of the drive assembly 130 relative to the housing 102. Some embodiments can be configured such that the slider component 106 can be longitudinally movable or slidable along the longitudinal axis 178 relative to the housing 102 in order to drive or result in linear motion of the needle component 120 and the plunger 122.

As shown in the FIGS. 2-6B, the drive assembly 130 can comprise a drive component 160, a plunger driver 162, and a needle driver 164. In some embodiments, longitudinal or linear motion of the slider component 106 along the longitudinal axis 178 can be converted to result in rotation of the drive component 160 of the drive assembly 130, which can then be converted to result in longitudinal or linear motion of the needle component 120 and the plunger 122 along the longitudinal axis 178 relative to the housing 102. In accordance with some embodiments, motion of the components along the longitudinal axis 178 can be parallel relative to the longitudinal axis 178. FIGS. 14A-16E, discussed further below, illustrate interactions between the components of the needle assembly 104 and the drive assembly 130, according to some embodiments.

FIGS. 2, 9A, and 9B illustrate configurations by which the sleeve mount 144 can be coupled to the housing 102. For example, the sleeve mount 144 can comprise a protrusion or groove 146 that can meet with a corresponding protrusion or groove 148 of one or more portions of the housing 102. When the housing 102 is assembled, the protrusion 148 can be received within the groove 146, thereby securing the sleeve mount 144 relative to the housing 102. Further, in some embodiments, when the inserter 100 is assembled, the needle component 120 and the plunger 122 are movable relative to each other, the housing 102, and the sleeve component 124.

As illustrated, FIG. 9A is a perspective view of a sleeve mount 144 coupled to a straight sleeve component 124. FIG. 9B illustrates a sleeve component 124 that has a slight curve or bend 290. The bend 290 can be adjacent to the sleeve mount 144 and provide an angular deviation 292 from the longitudinal axis 178 within a range of between about 5° and about 30°, between about 8° and about 15°, between about 9° and about 13°, or at about 10° relative to the longitudinal axis of the inserter.

The bend in the sleeve 124 can improve the accessibility to areas of the eye, such as when the inserter approaches the eye from a position in which the inserter is positioned above the cheekbone.

Additionally, as illustrated, a distal end portion 294 of the sleeve component 124 can be substantially straight while a proximal end portion 296 of the sleeve component 124 can comprise a curve or bend. The proximal end portion 296 can be about one quarter to about one half of the overall length of the sleeve component 124. In some embodiments, the length of the proximal end portion 296 can be about one third of the length of the sleeve component 124. Accordingly, in some embodiments, the distal end portion 294 can be about one half to about three quarters of the length of the sleeve portion 124, and in some embodiments, about two thirds of the length of the sleeve portion 124. Advantageously then, the distal end portion 294 of the sleeve component 124 can be of a sufficient length such that the entirety of the sleeve component 124 that enters the eye is substantially straight.

While the sleeve component 124 can comprise a rigid structure that can withstand typical bending stresses in performing embodiments of the procedures disclosed herein, the needle component 120 can be made from a flexible shaft that can deflect during proximal withdrawal of the needle component 120 into the sleeve component 124.

Thus, a proximal portion of the needle component 120 that extends along the bend 290 of the sleeve component 124 can be proximally withdrawn into the sleeve component 124 proximal or adjacent to the sleeve mount 144. After such motion, although the proximal portion of the needle component 120 was bent, that same portion of the needle component 120 can flex and straighten out as the needle component 120 is pulled proximally into a straight portion of the needle component 124 or other components within the inserter. Additionally, portions of the needle component 120 that reside in the distal end portion of the sleeve component 124 (and are therefore in a straight configuration) can be flexed or deflected into a curved or bent configuration when the needle component 120 is proximally retracted through the bend 290 of the sleeve component 124.

Accordingly, the use of an arcuate or bent sleeve component 124 in combination with a flexible or conforming needle component 120 can allow some embodiments of the inserter to provide improved accessibility to areas of the eye.

Some embodiments can implement aspects of the sleeve structures and methods of use disclosed in applicant's U.S. Patent Application Publ. No. 2012/0123434, the entirety of which is incorporated herein by reference.

The present disclosure may reference a "groove" or "grooves" as a structure that can be implemented in some embodiments. Where the word "groove" or "grooves" appears, such reference shall include (and vice versa) other structures that can guide motion or receive a corresponding protrusion, including a track, space between teeth, recess, cut, depression, hole, indentation, channel, path, slot, or aperture that extends at least partially into or through a component, as well as their equivalents. Furthermore, the present disclosure may reference a "protrusion" or "protrusions" as a structure that can be implemented in some embodiments. Where the word "protrusion" or "protrusions" appears, such reference shall include (and vice versa) other structures, including a ridge, protuberance, tooth, bump, or other protuberance, as well as their equivalents. Furthermore, when used in corresponding structures, grooves and protrusions can be interchanged. Thus, although various permutations of structures are available through the disclosure and teachings herein, the present disclosure provides only a few examples of protrusion/groove configurations, but is not limited to these configurations.

FIG. 3 illustrates a perspective, exploded view of components of the drive assembly 130. The drive component 160 is shown as a two-part structure that, when assembled, at least partially encloses one or more portions of other components of the drive assembly 130 (shown in FIG. 2). The two parts of the drive component 160 can be secured to each other using a series of interconnecting protrusions and recesses, thereby facilitating mechanical and/or adhesive coupling of the parts to form a composite component.

The drive component 160, as discussed below, can comprise one or more grooves and/or one or more protrusions to facilitate engagement and transfer of movement to the other components of the drive assembly 130. The embodiment illustrated in the figures demonstrates that the drive component 160 can comprise a series of grooves that engages with respective protrusions or grooves of the other components of the drive assembly 130 to facilitate the conversion of motion from one form to another. The operation and movement of the components of the drive assembly 130 in the illustrated embodiment represent one of a variety of embodiments that can be implemented in accordance with the disclosure and teachings herein.

In the embodiment illustrated in FIG. 3, the slider component 106, the plunger driver 162, and the needle driver 164 can each comprise a radial protrusion extending into a groove of the drive component 160 in order to facilitate transmission of axial or longitudinal forces between the components and the drivers for actuating the inserter 100. The drive component 160 can comprise one or multiple engagement grooves to engage with the slider component 106, the plunger driver 162, and the needle driver 164.

Figure 4A:
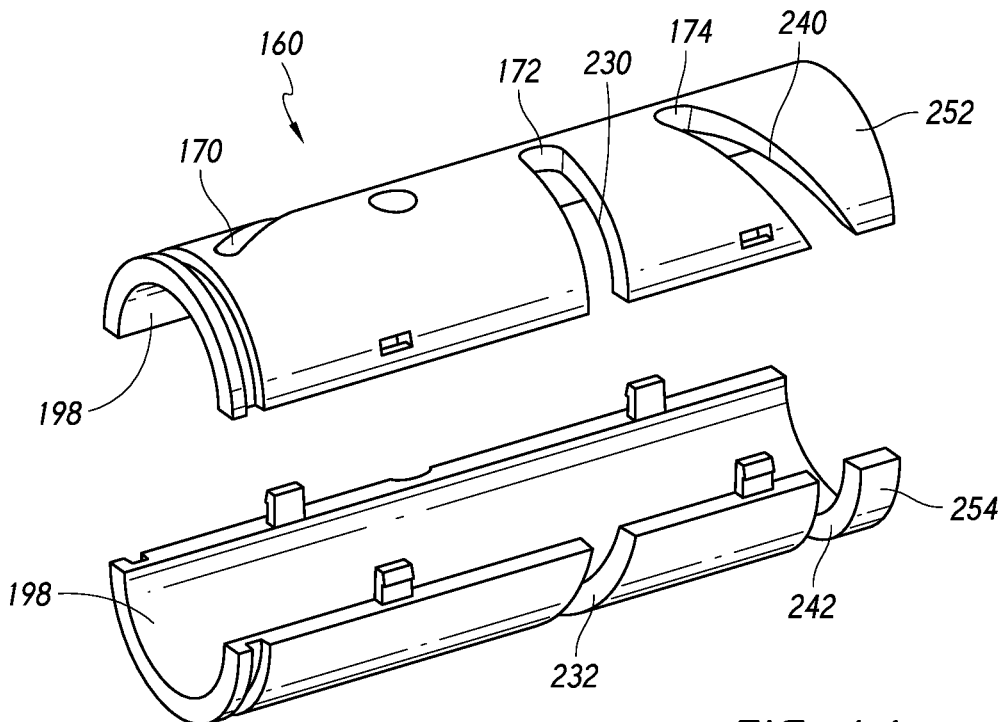
FIGS. 4A and 4B are perspective views of a drive component of the drive assembly shown in FIG. 3, according to some embodiments.
Figure 4B:
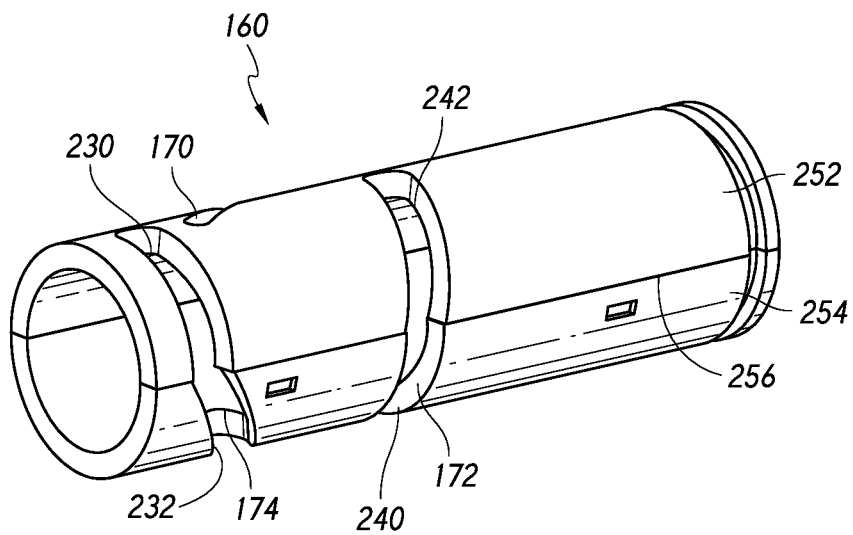

FIGS. 3-4B illustrate an embodiment of the drive component 160. As shown in FIGS. 4A and 4B, the drive component 160 can comprise a groove 170 that can be configured to engage with a corresponding protrusion of the slider component 106. Further, the drive component 160 can also comprise first and second driving grooves 172, 174 that can be configured to slidingly engage corresponding protrusions of the plunger driver 162 and the needle driver 164. Thus, the slider component 106 can comprise a protrusion 180 (shown in FIG. 12B), the plunger driver 162 can comprise a protrusion 182 (shown in FIGS. 5A and 5B), and the needle driver 164 can comprise a protrusion 184 (shown in FIGS. 6A and 6B). This arrangement of slots and protrusions can facilitate the transfer of motion from the slider component 106 to the respective ones of the needle component 120 and the plunger 122.

As mentioned above, some embodiments can be configured such that the protrusions and grooves are reversed such that one or more of the slider component 106, the plunger driver 162, or the needle driver 164 comprises a groove into which a protrusion of the drive component 160 can be received. In such embodiments, the inner protrusion can be slidably coupled or mounted to the drive component 160 so as to slide within grooves of the drive component 160 and result in rotational movement of the drive component 160 to result in longitudinal movement of the plunger driver 162 and the needle driver 164. In yet other embodiments, the drive component 160 can comprise a radially protruding ridge along which the plunger driver 162 or the needle driver 164 can slide (such as by a ridge and slot engagement, thereby enabling a ridge of the drive component 160 to slide through a slot of the plunger driver 162 or the needle driver 164). Such protrusions of the drive component 160 can project radially inwardly (toward the longitudinal axis 178) or radially outwardly (away from the longitudinal axis 178) from a surface of the drive component 160. Various modifications to the interactive structures of the slider component 106, the plunger driver 162, the needle driver 164, and the drive component 160 can be implemented in accordance with some embodiments of the inserter 100.

In some embodiments, although the drive component 160 can rotate relative to the housing 102, the slider component 106, the plunger driver 162, and the needle driver 164 can be restrained from rotational movement (about the longitudinal axis 178) relative to the housing 102. In some embodiments, a portion of the slider component 106, the plunger driver 162, and/or the needle driver 164 can be constrained from rotation relative to the housing 102 through direct or indirect engagement with the housing 102. The slider component 106 can slide along the slot 110 of the housing 102 and be engaged with the slot 110 via the protrusion 180. This engagement can permit longitudinal movement of the slider component 106 while restraining rotation of the slider component 106 relative to the housing 102. Further, the plunger driver 162 and/or the needle driver 164 (which can be disposed radially inwardly relative to the drive component 160) can comprise one or more guide surfaces or structures having a shape that engages with a corresponding internal guide surface or structure of the housing 102, thereby constraining rotational movement of the plunger driver 162 and/or the needle driver 164 relative to the housing 102.

For example, in some embodiments, the plunger driver 162 and the needle driver 164 can comprise elongate bodies having a portion thereof that includes a substantially rectangular cross-sectional profile. As illustrated in FIGS. 5A-6B, the plunger driver 162 and the needle driver 164 can comprise corresponding cross-sectional profiles that enable the plunger driver 162 and the needle driver 164 to be assembled together in in a manner that allows the plunger driver 162 and the needle driver 164 to slide along the longitudinal axis 178 relative to each other while constraining rotation of the plunger driver 162 relative to the needle driver 164 about the longitudinal axis 178.

Figure 5A:
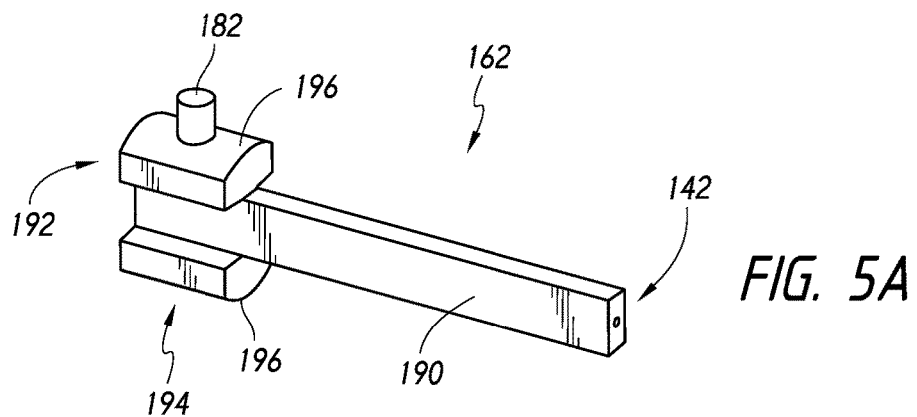
FIGS. 5A and 5B are perspective views of a plunger driver of the drive assembly shown in FIG. 3, according to some embodiments.
Figure 5B:
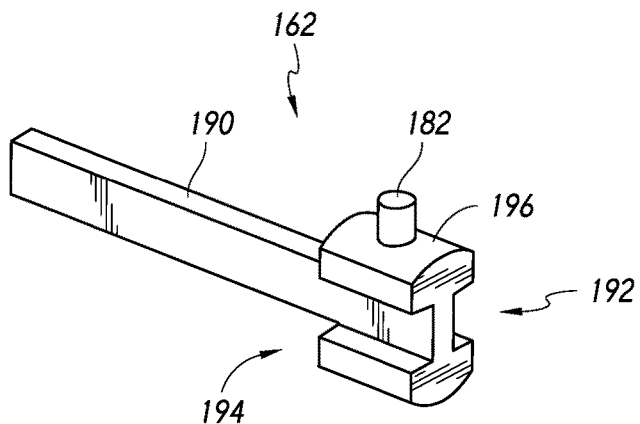

As shown in FIGS. 5A and 5B, the plunger driver can comprise an elongate body portion 190. The elongate body portion 190 can comprise a substantially rectangular cross-sectional profile. The elongate body portion 190 can be coupled to an alignment portion 192. The plunger driver 162 can also comprise an alignment portion 192 that is coupled to a proximal end 194 of the elongate body portion. The alignment portion 192 can comprise the protrusion 182, as discussed above. Further, the alignment portion 192 can comprise an outer or external guide surface 196 that is configured to abut or correspond to an inner or internal guide surface of the drive component 160. For example, as shown in FIG. 3, the external surface 196. The guide surface 196 can be configured to abut with a corresponding guide surface 198 of the drive component 160.

Figure 6A:
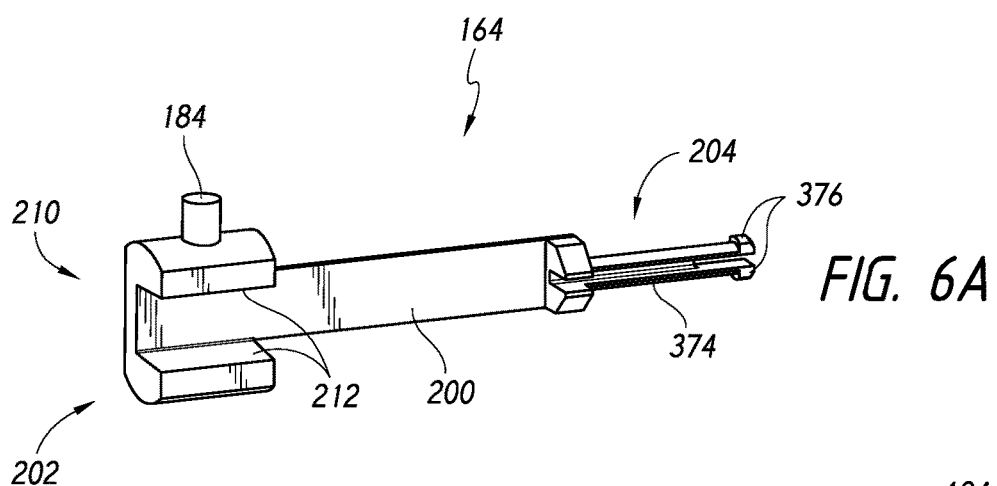
FIGS. 6A and 6B are perspective views of a needle driver of the drive assembly shown in FIG. 3, according to some embodiments.
Figure 6B:
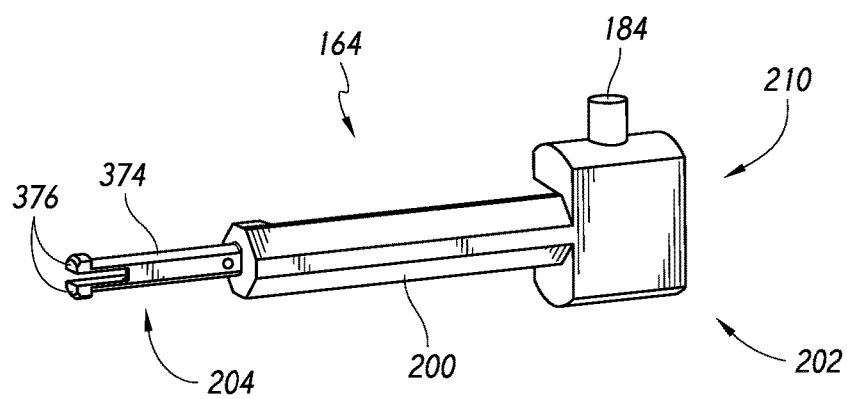

Referring now to FIGS. 6A and 6B, the needle driver can also comprise an elongate body portion 200 having a proximal end 202 and a distal end 204 the needle driver 164 can comprise an alignment portion 210 coupled to the proximal and 202. The alignment portion 210 can comprise the protrusion 184, as discussed above. The alignment portion 210 can also be configured to comprise at least one engagement structure or guide surface 212. As illustrated, the engagement structure 212 can comprise a cavity having a substantially rectangular cross-sectional profile. The cross-sectional profile of the engagement structure 212 can correspond to a cross-sectional outer profile of the elongate body portion 190 of the plunger driver 162.

Accordingly, as illustrated in FIG. 3, when assembled, the elongate body portion 190 of the plunger driver 162 can fit slidably into the cavity of the engagement structure 212 of the needle driver 164. The sliding engagement between the elongate body portion 190 and the engagement structure 212 can permit longitudinal movement of the plunger driver 162 relative to the needle driver 164 while the close fit of the rectangular cross-sectional profiles of the elongate body portion 190 and the engagement structure 212 substantially constrain rotation of the plunger driver 162 relative to the needle driver 164.

Additionally, rotation of the plunger driver 162 and the needle driver 164 relative to the housing 102 can be constrained through engagement of the cross-sectional profiles of one or both of the plunger driver 162 or the needle driver 164 with/between a corresponding engagement structure or guide surface inside a cavity 228 of the housing 102. Accordingly, the plunger driver 162 and the needle driver 164 can be constrained from rotation relative to the housing 102, in accordance with some embodiments.

Figure 13A:
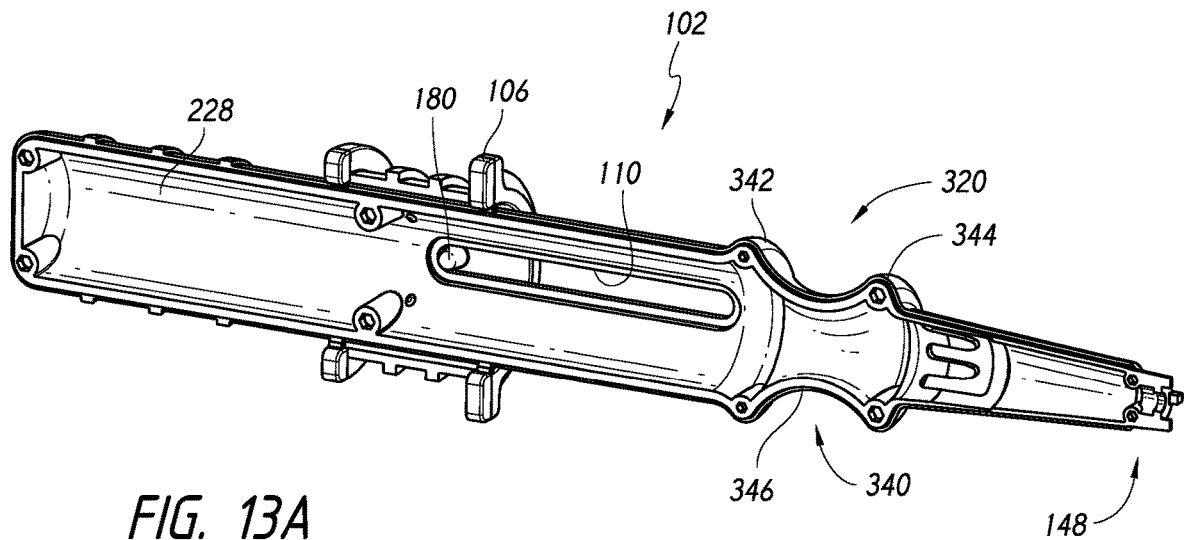
FIGS. 13A and 13B are perspective views of a housing of the inserter shown in FIG. 1B, according to some embodiments.
Figure 13B:
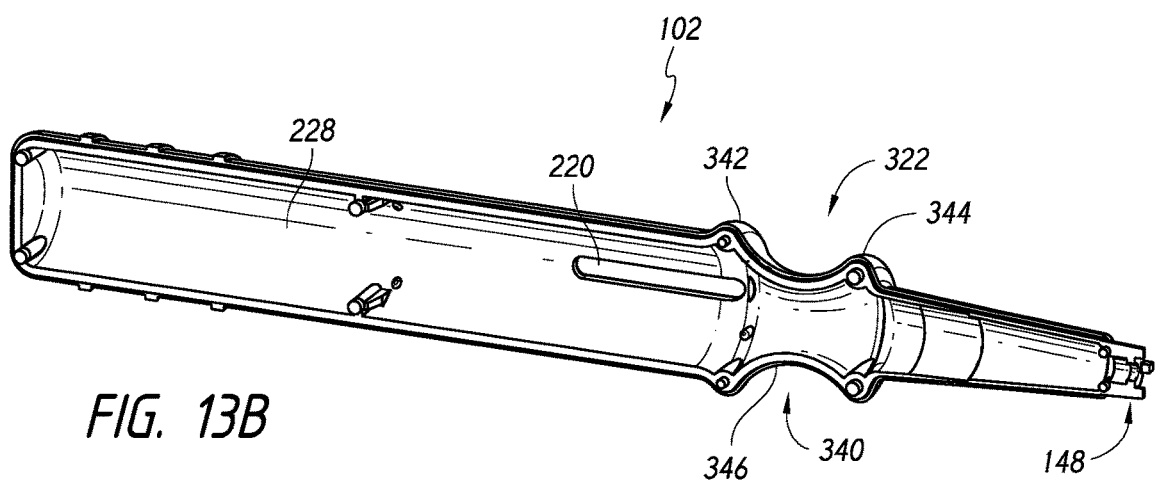

In some embodiments, in order to constrain rotation of the plunger driver 162 and the needle driver 164 relative to the housing 102, the protrusion 182 of the plunger driver 162 and the protrusion 184 of the needle driver 164 can extend through the drive component 160 and engage with a corresponding slot 220 of the housing 102 (shown in FIG. 13B). Because the protrusions 182, 184 extend through the drive component 160 and into the slot 220 of the housing 102, the protrusions 182, 184 can engage with the housing 102 in order to constrain or control rotational movement of the plunger driver 162 and the needle driver 164 relative to the housing 102. The protrusions 182, 184 can track a given path, whether straight or curvilinear, defined by the slot 220 formed in the housing 102. In the illustrated embodiments, the slot 220 of the housing 102 can be used for both the plunger driver 162 and the needle driver 164. Further, the slot 220 can define a path that is substantially parallel relative to the longitudinal axis 178 of the housing 102.

In addition, in accordance with some embodiments, the slider component 106 can be configured such that the protrusion 180 of the slider component 106 extends through the housing 102 and into the groove 170 of the drive component 160.

Figure 11:
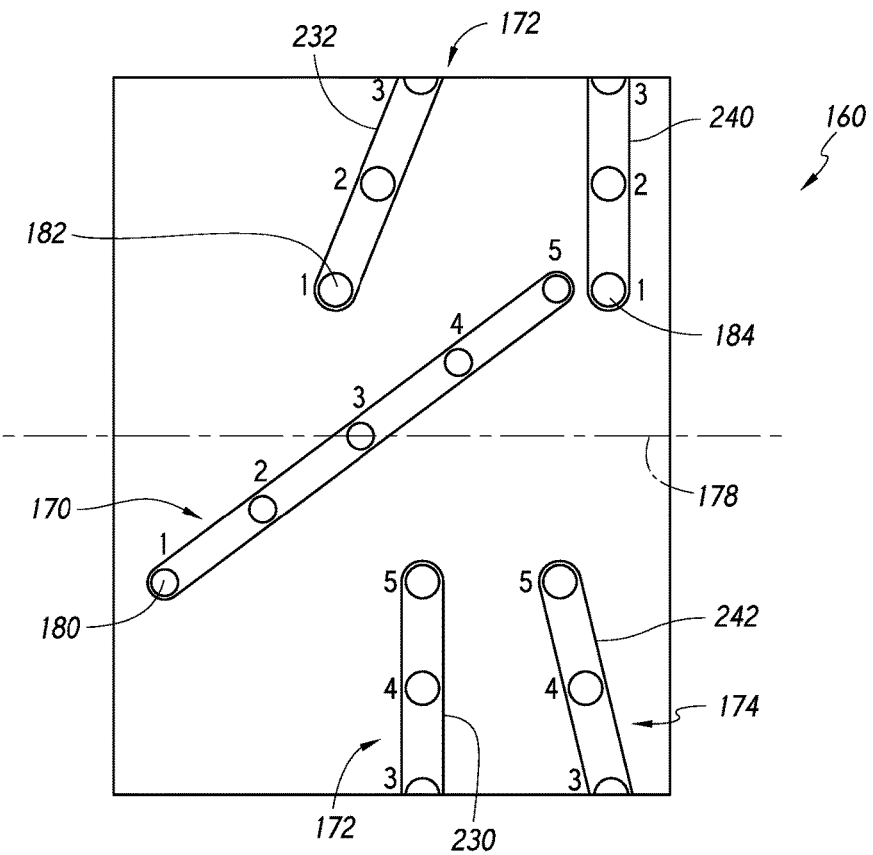
FIG. 11 is a schematic view of an outer surface of the drive component, illustrating groove paths, according to some embodiments.

As illustrated in FIGS. 4A and 4B, the slider groove 170 can extend in a helical path about the drive component 160. The helical path of the slider groove 170 can extend in a substantially straight path when viewed in a planar layout, as shown in FIG. 11 (e.g., the slider groove 170 can have a substantially constant pitch). The protrusion 180 of the slider component 106 can move or pass within the slider groove 170 from a first position to a second, third, fourth, and fifth positions. As the slider component is moved longitudinally along the housing 102, the protrusion 180 moves between the positions illustrated in FIG. 11. This longitudinal movement of the protrusion 180 along the longitudinal axis 178 can result in rotational movement of the drive component 160. And as discussed herein, the rotational movement of the drive component 160 can result in longitudinal movement along the longitudinal axis 178 to the plunger driver 162 and/or the needle driver 164.

Referring again to FIGS. 4A and 4B, the first and second driving grooves 172, 174 of the drive component 160 can be configured to engage with the protrusions 182, 184. In the illustrated embodiment, the first and second driving grooves 172, 174 can each comprise a linear or straight portion through which the protrusion can pass without causing longitudinal movement of the respective drive component and an angled portion through which the protrusion can pass which results in longitudinal movement of the respective driving component. For example, the first driving groove 172 can comprise a straight portion 230 and an angled portion 232. The protrusion 182 of the plunger driver 162 can move or pass along various positions within the first driving groove 172. This motion can be driven as a result of motion of the slider component 106.

FIG. 11 illustrates the paths of the first and second driving grooves 172, 174 and the slider groove 170 of the drive component 160 in a planar representation, in accordance with some embodiments. Referring to the first driving groove 172, the protrusion 182 can move from a first position to a second, third, fourth, and fifth positions within the first driving groove 172, as shown. As illustrated, as the first protrusion 182 moves from the first position to the second position within the angled portion of the first driving groove, such movement results in the plunger driver moving relative to the drive component 160 along the longitudinal axis 178. The movement of the plunger driver 162 from the first position to the second and third positions is illustrated in the cross-sectional side views of FIGS. 14A-14C. As demonstrated, as the protrusion 182 moves through the angled portion 232 of the first groove 172, the plunger driver 162 can be advanced in a distal direction along the longitudinal axis 178 until the protrusion 182 enters the straight portion 230 of the first driving groove 172. Thereafter, in the third, fourth, and fifth positions, the protrusion 182 will maintain a generally constant longitudinal position along the longitudinal axis 178 relative to the drive component 160. Accordingly, the plunger driver 162 will not change its longitudinal position along the longitudinal axis 178 as the drive component continues to rotate, causing the protrusion 182 to move from the third position to the fifth position.

Similar to the arrangement of the protrusion 182 within the first driving groove 172, the protrusion 184 can extend within the second driving groove 174 and pass along the path defined by the second driving groove 174. The second driving groove 174 can comprise a straight portion 240 and an angled portion 242. The protrusion 184 of the needle driver 164 can move from a first position to a second, third, fourth, and fifth positions. In the first, second, and third positions, the protrusion 184 will substantially maintain its longitudinal position along the longitudinal axis 178 relative to the drive component 160. However, as the protrusion 184 leaves the straight portion 240 of the second driving groove 174 and enters the angled portion 242, the longitudinal position of the needle driver 164 along the longitudinal axis 178 will begin to change. Thus, during initial rotation from the first position to the third position, the needle driver 164 will maintain its longitudinal position along the longitudinal axis 178 relative to the drive component 160. However, the needle driver 164 will be proximally retracted along the longitudinal axis 178 relative to the drive component 160 as the protrusion 184 is moved through the angled portion 242 of the second driving groove 174.

Figure 16A:
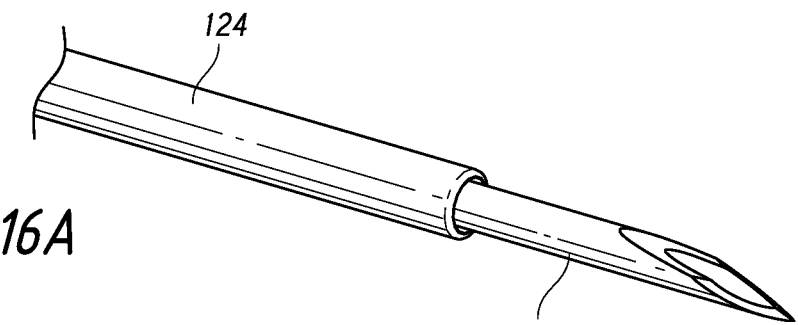
FIGS. 16A-16E are perspective views of the stages of motion of a needle and sleeve of the drive assembly illustrated in FIGS. 15A-15E, according to some embodiments.
Figure 16B:
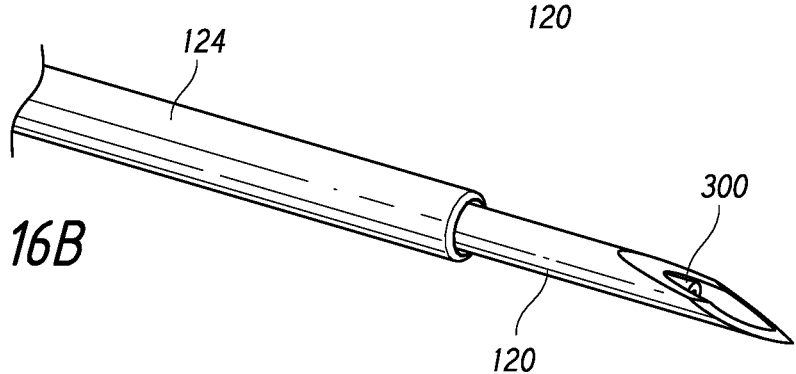

Motion of the slider component 106 and the resultant movement of the components of the drive assembly 130 will be described with reference to FIG. 11 and FIGS. 14A-16E. At position 1 (of FIG. 11), as shown in FIGS. 14A and 15A, the slider component 106 can be moved distally toward position 2. Movement from position 1 to position 2 results in rotation of the drive component 160, which also results in longitudinal movement of the plunger driver 162, as shown in FIGS. 14B and 15B. As shown in FIG. 16B, the resulting movement of the plunger driver 162 in a distal direction along the longitudinal axis results in movement of a shunt 300 such that the shunt 300 is initially exposed from within the needle component 120.

Figure 16C:
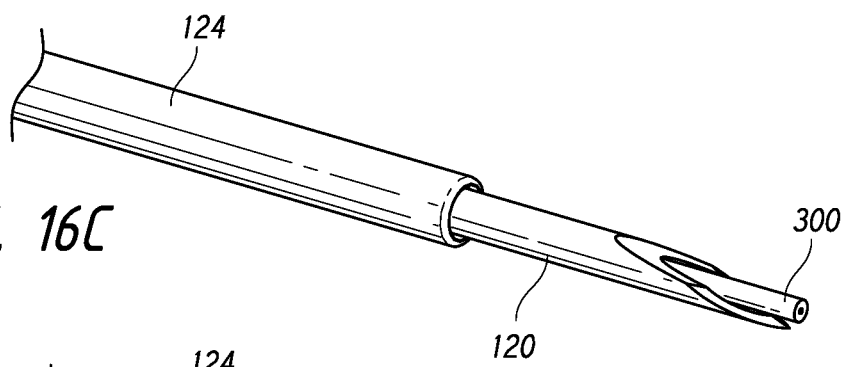

Thereafter, with continued movement of the slider component 106 toward position 3, the plunger driver 162 continues to move distally while the needle driver 164 maintains its same longitudinal position along the longitudinal axis relative to the drive component 160, as illustrated in FIGS. 14C and 15C. As a result, the shunt 300 is pushed out of or further out of the needle component 120, as shown in FIG. 16C.

Further distal movement of the slider component 106 along the longitudinal axis results in the protrusion 180 moving from position 3 to position 4. This continued rotation of the drive component 160 no longer results in distal longitudinal movement of the plunger driver 162 along the longitudinal axis. Instead, the continued rotation of the drive component 160 begins to result in proximal longitudinal retraction of the needle driver 164 relative to the drive component 160 along the longitudinal axis. As a result, the needle begins to retract to within the sleeve 124, as shown in FIG. 14D, 15D, and 16D or 16E.

Figure 16D:
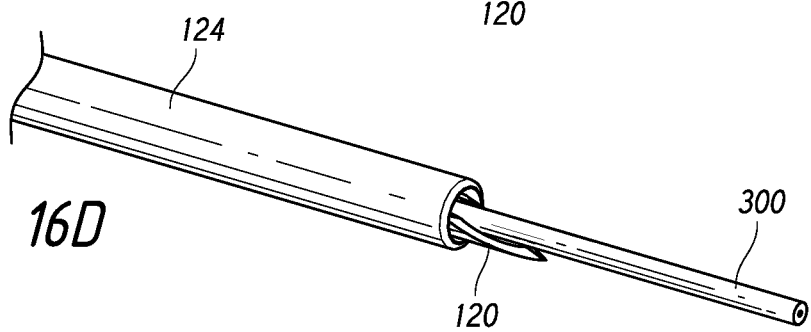
Figure 16E:
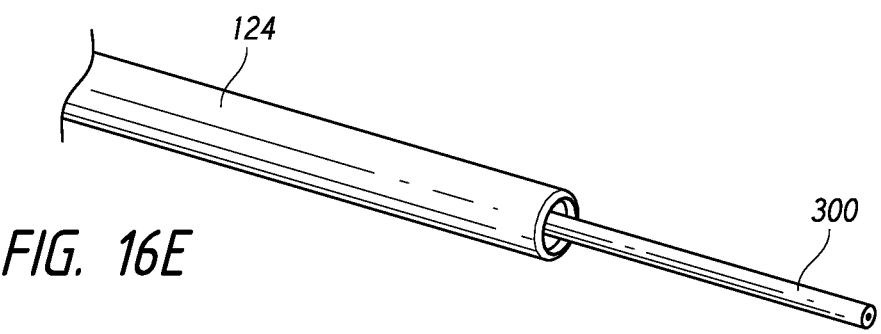

Thereafter, continued movement of the slider component 106 toward position 5 will continue to result in proximal retraction of the needle driver 164 relative to the drive component 160 while the plunger driver 162 maintains its relative longitudinal position with respect to the drive component 160. As a result, the needle component 120 can be withdrawn into the sleeve 124 as shown in FIG. 16D or FIG. 16E. The shunt 300 can be left in the desired or target area as the needle and the sleeve 124 are withdrawn. While the needle component 120 is proximally retracted, as illustrated in FIG. 16D-16E, the plunger 122 (although not shown in FIGS. 16A-16E) can maintain its longitudinal position relative to the sleeve 124 to provide a proximal stop and prevent proximal retraction of the shunt 300 as the needle component 120 is proximally retracted into the sleeve 124.

FIG. 16D illustrates a final position of the needle component 120 relative to the sleeve 124, and FIG. 16E illustrates an embodiment in which the needle component 120 is fully retracted proximally into the sleeve 124. In accordance with some embodiments, the position of the needle component 120, as shown in FIG. 16D, can aid in resisting or preventing damage to the eye tissue or the shunt during implantation of the shunt.

For example, when withdrawing the needle component 120 into the sleeve 124, the operator may inadvertently move the needle relative to the sclera, thereby creating a sideways or vertical tension or force, which can bend or stress the needle component 120. This sideways or vertical force can result when an operator attempts to position the inserter above a facial feature of the patient. Oftentimes, given that one of the preferred implantation locations of the eye requires the operator to position and hold the inserter above the cheekbone, the patient's cheekbone and/or knows may obstruct proper positioning of the inserter relative to the eye.

Due to the operator's potential exertion of force in a sideways or vertical direction, it may be preferable to leave at least a portion of the bevel exposed from a distal end of the sleeve 124 and to withdraw the entire inserter from the eye all at once in the configuration shown in FIG. 16D. Thus, until a proximal withdrawal of the inserter (including the sleeve 124) is performed to release the shunt 300 into the eye, a portion of the bevel of the needle component 120 can remain exposed and/or in contact with the eye tissue (e.g., the sclera). As a result of leaving the needle component 120 exposed or engaged with the eye tissue, the engagement of the needle component 120 with the eye tissue can tend to provide resistance against any sideways or vertical forces. Thus, the inserter will not tend to "jump" or undergo a substantial shift prior to proximal withdrawal of the sleeve 124 away from the eye tissue.

One of the advantageous results of maintaining a portion of the bevel exposed from the distal end of the sleeve 124 includes preventing damage to the eye tissue, which can take place if the sleeve suddenly moves sideways or vertically while maintaining its longitudinal position relative to the eye tissue. In such situations, the distal end of the sleeve 124 may scrape or otherwise damage the eye tissue. In some situations, damage to the eye can include damage to the iris, such as dissecting the iris.

Further, because the shunt 300 can extend at least partially into the sleeve 124 after the needle component 120 is fully withdrawn into the sleeve 124, a substantial sideways or vertical force exerted on the sleeve 124 may result in substantial contact between a lumen of the sleeve 124 and the shunt 300. In some situations, this contact can pull the shunt 300 out of the eye tissue or otherwise damage the proximal end or inflow end of the shunt 300.

In accordance with some embodiments, between about one-quarter and about a full longitudinal length of the bevel (as measured along the longitudinal axis) can be exposed from the distal end of the sleeve component 124, as shown in FIG. 16D. In some embodiments, the needle bevel can extend from the sleeve distal end at a distance of about one-quarter of the bevel longitudinal length to about three-quarters of the bevel longitudinal length. Furthermore, in some embodiments, the bevel can extend from the sleeve 124 at length of about one-half of the bevel longitudinal length. For example, in accordance with some embodiments, a distal tip of the bevel can extend or protrude at a distance of about 1 mm, about 2 mm, or about 3 mm or more from a distal end of the sleeve component 124. Other refinements and embodiments can be performed using these teachings disclosed herein.

As an alternative to FIG. 16D, the needle component 120 can be fully retracted into the sleeve 124 prior to proximal retraction of the sleeve 124 from the eye.

After maintaining the needle component 120 at least partially exposed or engaged with the eye tissue, as illustrated in FIG. 16D, proximal retraction of the sleeve component 124 and the needle component 120 can mitigate or prevent sideways and/or vertical forces from being exerted on the shunt 300. Thus, as the operator's hand moves proximally to withdraw the inserter from the eye, most or all of any sideways or vertical tension is removed from the inserter.

Although the groove pathways illustrated in FIG. 11 demonstrate one embodiment of the relative movement and actuation of the components of the drive assembly 130, other pathways can be utilized to create different types of motion of the respective components of the drive assembly 130.

For example, the angled portion of the grooves can have a curvilinear path that increases or decreases longitudinal displacement of a given component per unit of rotation as the drive component 160 rotates. The slider groove 170 can be straight or have a curvilinear section so as to provide a variable actuation or increase or decrease the rate of rotation per unit of longitudinal movement of the slider component 106.

Similarly, the angled portions of the first and second driving grooves 172, 174 can have curvilinear portions that increase or decrease the amount of longitudinal displacement per unit rotation. The first and second driving grooves 172, 174 can be configured as a substantially curvilinear grooves that transition from a straight portion to an angled portion or from permitting longitudinal displacement of a respective component to maintaining the longitudinal position of that respective component. The first and second grooves 172, 174 can therefore have either a more well-defined transition between portions of the groove, along which movement of the protrusions result in movement along the axis 178 and portions of the groove that maintain a position along the axis 178 of a respective component. Alternatively, the first and second grooves 172, 174 can have a pathway that provides a gradual, smooth, or less perceptible transition between a portion of the groove, along which movement of the protrusion results in movement of a given component along the axis 178, to another portion of the groove, along which movement of the protrusion results in maintaining a position along the axis 178 of the given component.

Furthermore, the first and second grooves 172, 174 and/or the slider groove 170 (any one or any combination thereof) can have multiple sections or portions thereof that provide a different actuation mechanism or rate of rotation or longitudinal displacement along the longitudinal axis. Accordingly, persons of skill in the art can implement various embodiments to achieve desired articulations of components of the inserter disclosed herein.

According to some embodiments, as shown in FIGS. 4A and 4B, the drive component 160 can comprises a two-piece design using first and second portions 252, 254. The two-piece design can allow two or more grooves to be implemented in an injection moldable process using two pieces. Thus, a single composite drive component 160 can be injection molded while enabling the drive component 160 to comprise one or more grooves that extend partially or completely along the body of the component 160. This allows the grooves to change direction at a split line 256 between the first and second portions 252, 254, so that complex groove lines become moldable. For example, given the limitations of injection molding processes, a single molded piece would not allow for groove lines that change direction, since the component would not be removable from the mold. Therefore post-molding machining would be required. However, some embodiments disclosed herein advantageously overcome this problem using the manufacture of a two-piece component by way of injected molding.

As shown in FIG. 10, the inserter 100 can also comprise a cap component 310. The cap component 310 can comprise a first end 312 and a second end 314. The cap component first end 312 can be open and be configured to engage with a portion of the housing 102 in order to secure the cap component 310 onto a distal portion of the housing 102 in order to cover and protect the sleeve component 124 and the needle component 120.

Figure 12A:
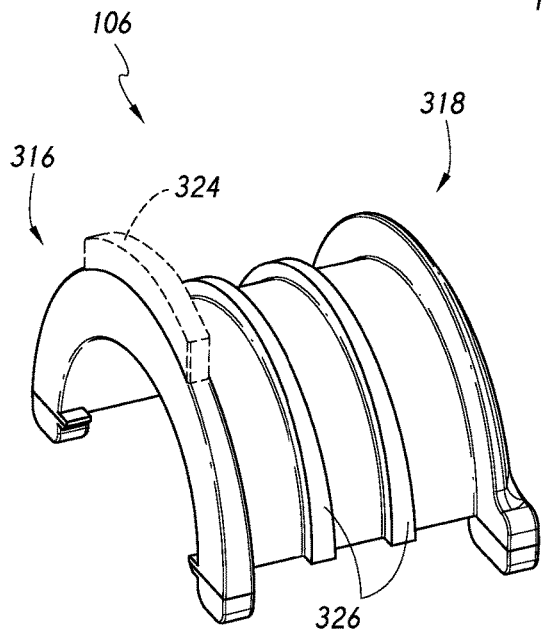
FIGS. 12A and 12B are perspective views of a slider component of the inserter shown in FIG. 1B, according to some embodiments.
Figure 12B:
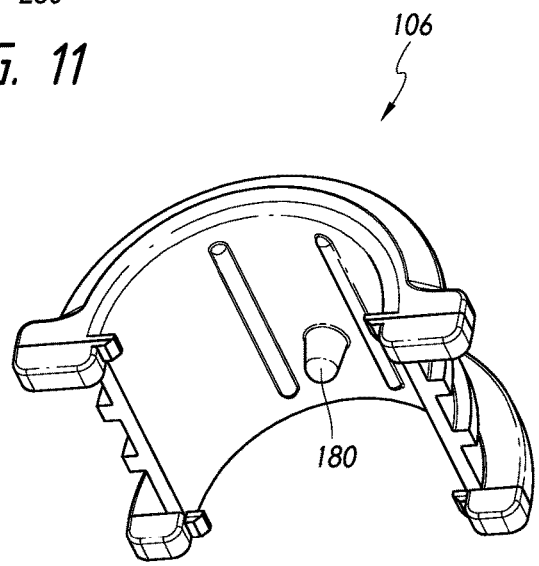

FIGS. 12A and 12B are perspective views of a slider component 106 of the inserter shown in FIG. 1B, according to some embodiments. FIG. 12A illustrates a top perspective view of the slider component 106. The slider component 106 can comprise a proximal end 316 and a distal end portion 318. The proximal end portion 316 and the distal end portion 318 can comprise raised boundaries or edges that protrude radially from the slider component 106 in order to provide a secure, ergonomic grip with a thumb or finger of the operator during use.

In some embodiments, the proximal end portion 316 can comprise one or more radial protrusions 324. The radial protrusions 324 can allow the operator to have a structure that is easy to engage with their finger in order to provide a rotational motion or torsional force to the inserter in order to rotate the inserter about the longitudinal axis 178 of the inserter.

Further, although FIG. 12A illustrates that the slider component 106 can comprise one or more intermediate grooves or protrusions 326, one or both of the protrusions 326 can be omitted from the slider component 106. Indeed, in some embodiments, omission of the protrusions 326 can allow a finger of the operator to sit more deeply and securely between the proximal and distal end portions 316, 318 of the slider component 106. In yet other embodiments, the protrusions 326 can have a decreased profile, variable profile, or be provided as a series of random or symmetrically placed bumps or spiny protrusions or prickles.

Referring briefly to FIG. 12B, the protrusion 180 can be formed integrally with the body of the slider component 106. However, in accordance with some embodiments, the protrusion 180 can also be formed as a separate component that is later attached to the body of the slider component 106.

FIGS. 13A and 13B illustrate an embodiment of the housing 102. As shown, the housing 102 can comprise a first portion 320 and a second portion 322. The first and second portions can define an interior cavity 228 when assembled together. As generally illustrated in FIG. 2, the interior cavity 228 can enclose the drive assembly 130 therein.

The housing 102 can also comprise a groove 334 through which the protrusion 180 of the slider component 106 can pass. Thus, the slider component 106 can be coupled to the first portion 320 of the housing 102 and the protrusion 180 of the slider component 106 can extend through the groove 110. By extending through the groove 110, the protrusion 180 can engage the slider groove 170 of the drive component 160.

The second portion 322 of the housing 102 can also comprise the slot 220, as discussed above. The slot 220 can engage with the protrusions 182, 184 of the plunger driver 162 and the needle driver 164, respectively. When assembled, as illustrated in FIG. 1B, the slider component 106, the plunger driver 162, and the needle driver 164 will have a substantially fixed rotational position relative to the housing 102. Indeed, it is because of the free rotation of the drive component 160 relative to the housing 102 (in response to movement of the slider component 106) that longitudinal displacement of the plunger driver 162 and the needle driver 164 along the longitudinal axis can occur.

As also illustrated in FIGS. 13A and 13B, the housing 102 can comprise a grip section 340 comprising a saddle-shaped indentation in the housing 102. The grip section 340 can comprise first and second portions 342, 344 that extend radially outward from a longitudinal axis of the housing 102. The first and second portions 342, 344 can comprise ridges or proximal and distal annular protrusions that extend from an outer surface of the housing 102. The first portion 342 can provide resistance against proximal movement of an operator's hand relative to the housing 102. Further, the second portion 344 can extend radially outward for providing resistance against proximal movement of an operator's hand relative to the housing 102. In some embodiments, the grip section 340 can comprise a valley portion 346 disposed between the first and second portions 342, 344. The valley portion 346 can comprise an inner diameter, and the first and second portions 342, 344 can comprise a maximum outer diameter. The maximum outer diameter can be between about 1.5 and about 5 times as large as the inner diameter, between about 2.5 and about 4 times as large as the inner diameter, or between about 3 and about 4 times as large as the inner diameter.

The grip section 340 can enable an operator to firmly hold the distal portion of the housing 102 with or between their fingers while longitudinally actuating or moving the slider component 106 toward the grip section 340. In this manner, some embodiments permit one-handed actuation of the inserter 100. This advantageous feature of some embodiments can allow an operator to have free use of the other hand during a surgical procedure while being in full control of the inserter 100 with a single hand.

Additionally, various embodiments can be provided in which a length or pitch of the grooves in the drive component 160 can be modified in order to adjust the total travel of the slider component required to actuate the inserter. While a longer distance of travel may be preferred in order to provide smoother movement and controlled forces exerted on and by components of the inserter, various aspects of the drive assembly 130 can be modified in order to adjust the initial position of the slider component relative to the grip section 340. Such modifications or variations can be performed in order to provide a specific ergonomic design for a given operator. Other features and modifications can be performed in order to further personalize the ergonomics or operation of the inserter.

Rotational Adjustment of the Needle Bevel

Referring now to FIGS. 17-19C, an aspect of some embodiments of the inserter can be implemented to provide rotational control of the needle assembly. As illustrated in FIG. 1B, the inserter can comprise the needle assembly 104. In accordance with some embodiments, the needle assembly 104 can be configured to enable control of the rotational alignment of the needle component 120 relative to the housing 102. Accordingly, depending on an operator's position relative to a patient (e.g., whether the operator is approaching a left or right eye, or whether the operator is on a left or right side of a patient), the rotational alignment of the needle component 120 can be adjusted such that a bevel 360 of the needle can be rotationally positioned to a desired orientation relative to the eye tissue. This feature can allow the operator greater flexibility to hold the inserter while still making sure the bevel is up during the needle penetration through the sclera. It can also accommodate using the same inserter for left or right eye surgeries. In different surgical setups (temporal, superior, right eye, left eye, right handed, left handed) it can be advantageous to hold the inserter somewhat rotated for ease of access. By pre-rotating the needle bevel, such a rotation can be pre-compensated to assure the needle bevel is up during the scleral penetration phase.

The needle assembly 104 can comprise various components that can be interconnected to permit longitudinal displacement of the needle component 120 relative to the housing 102 while also allowing a rotational alignment of the needle bevel 360 to be adjusted. As shown in FIG. 2, the needle assembly 104 can comprise a needle mount 140, the needle component 120 coupled to the needle mount, a rotation adjustment component 370, and the needle driver 164. As shown in the cross-sectional side view of FIG. 17, the rotational adjustment component 370 can comprise a central aperture 372 into which a distal engagement portion 374 of the needle driver 164 can be passed and engaged. As illustrated, the engagement portion 374 can be received within the aperture 372 and a locking ridge or hook portion 376 that can secure the longitudinal position of the needle driver 164 relative to the rotational adjustment component 370. However, the aperture 372 and the engagement portion 374 can be configured to permit free rotational movement of the rotational adjustment component 370 relative to the needle driver 164. For example, the aperture 372 can comprise a generally cylindrical shape and the engagement portion 374 can comprise a generally cylindrical shape of a smaller outer diameter.

Figure 19A:
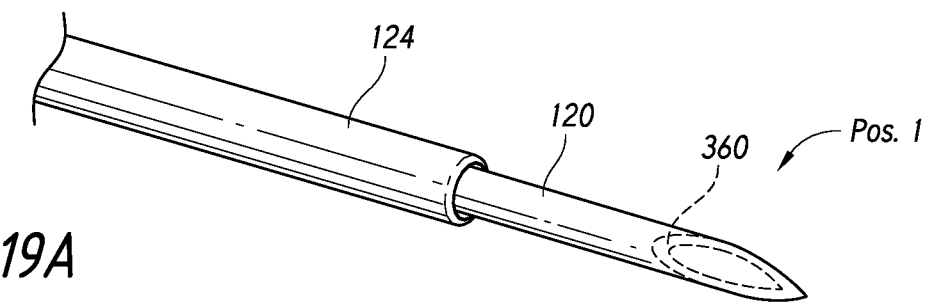
FIGS. 19A-19C illustrate rotational alignment positions of the needle in response to movement of the rotational adjustment mechanism, according to some embodiments.
Figure 19B:
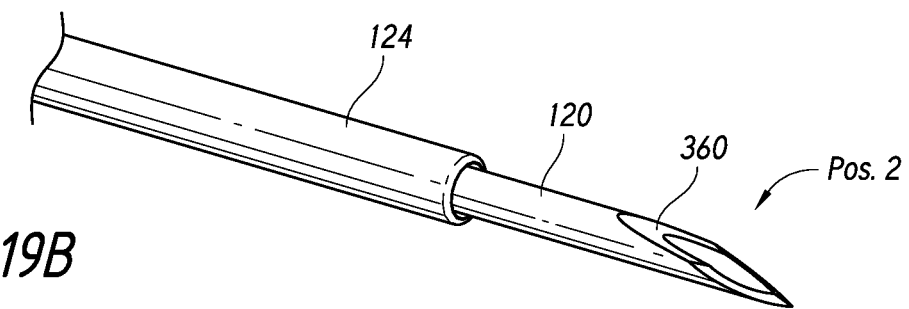
Figure 19C:
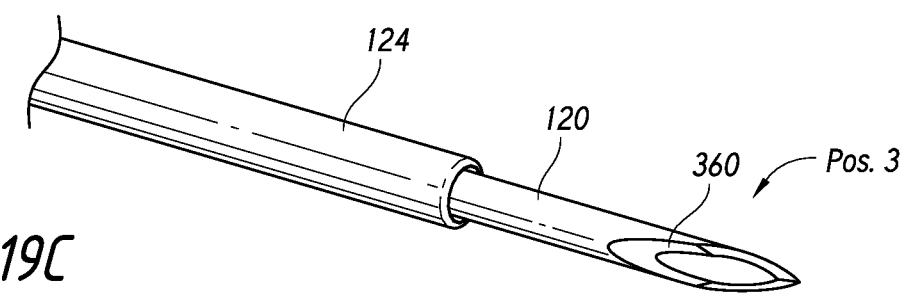
Figure 20:
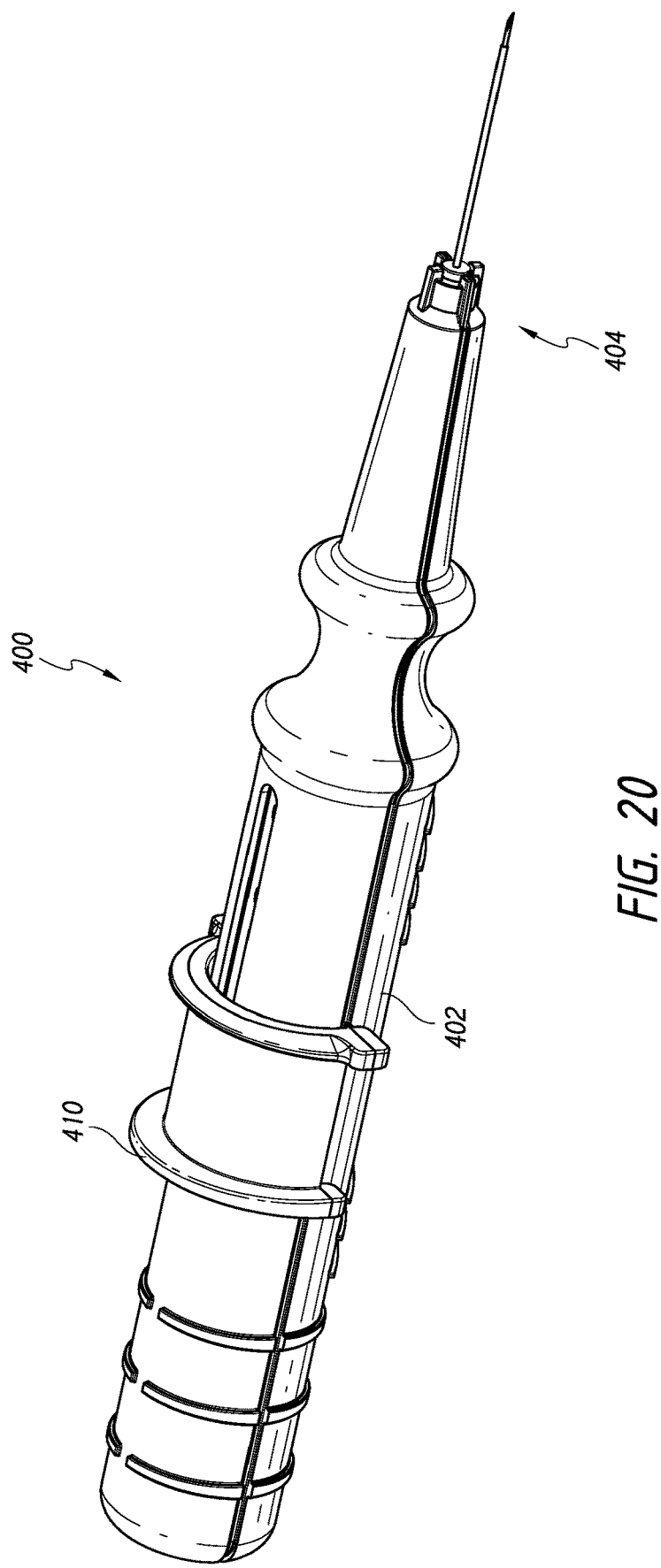
FIG. 20 is a perspective view of another inserter, according to some embodiments.
Figure 21:
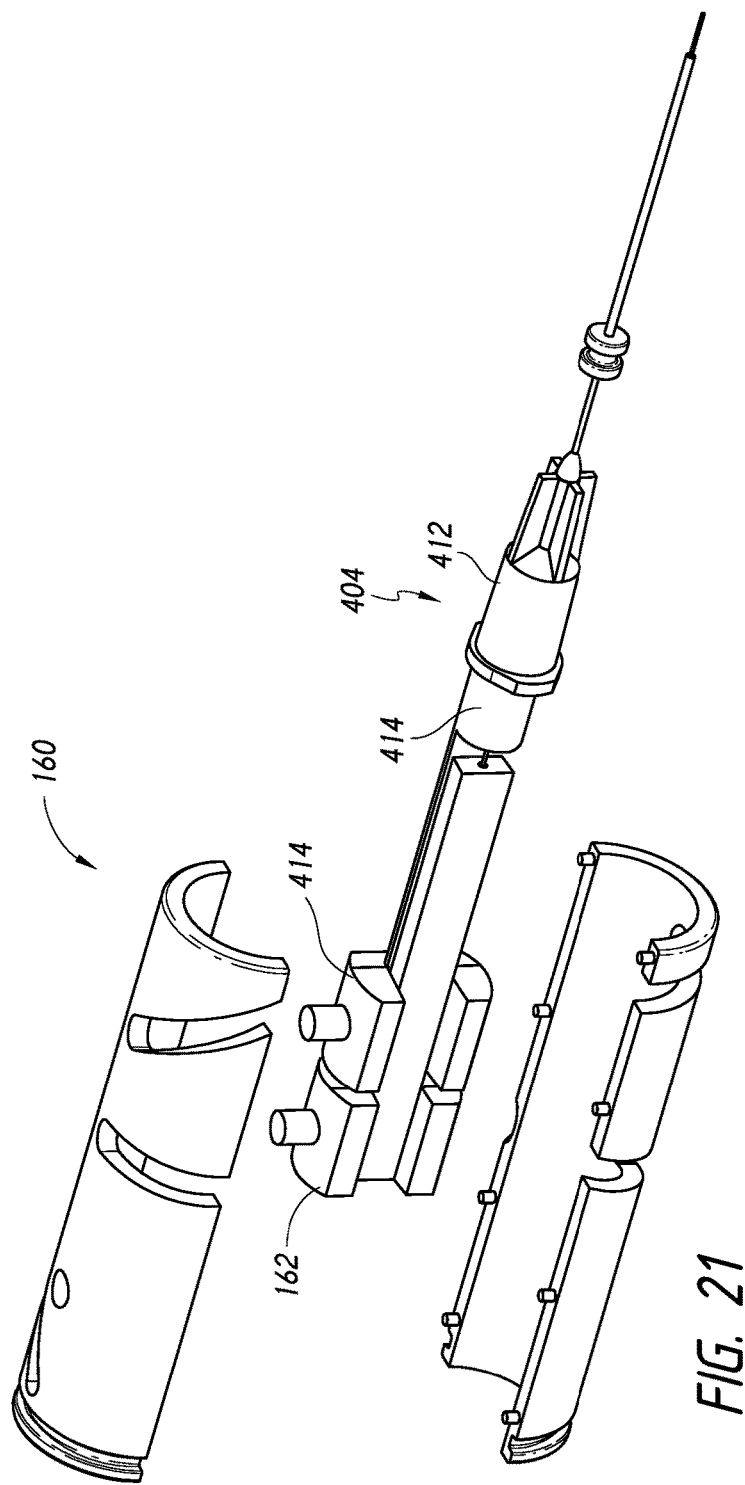
FIG. 21 is a perspective, exploded view of a drive assembly of the inserter shown in FIG. 20, according to some embodiments.
Figure 22:
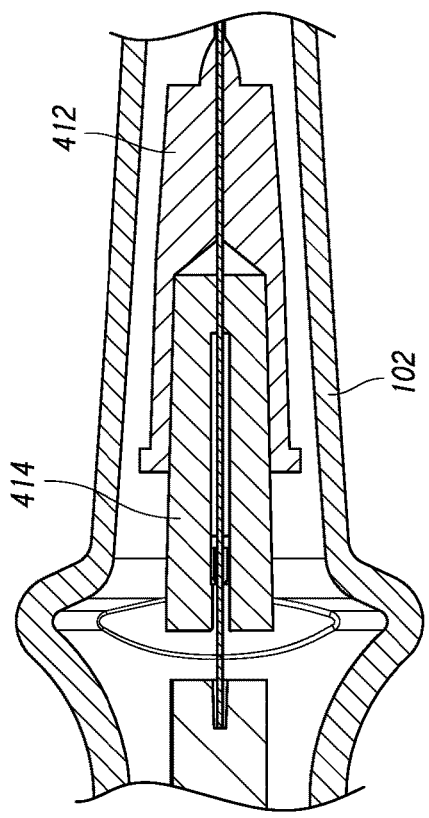
FIG. 22 is a side, cross-sectional view of the inserter shown in FIG. 20, according to some embodiments.

Further, the needle mount 140 can comprise a proximal cavity 380 having an inner surface configured to engage with an outer surface 382 of the rotational engagement component 380. The engagement between the outer surface 382 and the cavity 380 can rotationally and longitudinally secure the rotational adjustment component 370 relative to the needle mount 140. Accordingly, while the rotational adjustment component 370 will transfer longitudinal movement from the needle driver 164 to the needle mount 140, the rotational adjustment component 370 can allow an operator to adjust a rotational alignment of the needle mount 140 relative to the needle driver 164. Therefore, the needle component 120, which is coupled to the needle mount 140, can be rotationally aligned such that the bevel 360 is rotated to a desired alignment relative to the housing 102, as shown in FIGS. 19A-19C.

FIG. 18 illustrates potential pathways and rotational adjustment or alignment positions of an adjustment pin 390 of the rotational adjustment component 370. The adjustment pin 390 can move within one or more tracks 392 of a guide slot pathway 394 formed in the housing 102. As illustrated in FIG. 18, the guide slot pathway 394 can comprise three tracks 392 that permit the adjustment pin 390 to be moved relative to the housing 102, thereby transferring a rotational movement to the needle mount 140 and the needle component 120 so as to adjust a rotational position of the bevel 360 relative to the housing 102. Although the guide slot pathway 392 is shown as having three tracks 392, other embodiments can be provided in which two, four, five, or more tracks are used. Further, the guide slot pathway 394 can also be configured as an open space that allows for free adjustment of the rotational position into any position along an arcuate pathway or along an outer circumferential arc.

Needle Bevel Inserter with Fixed Rotational Orientation

As discussed above, some embodiments can implement the rotational adjustment component 370 to provide an actuation mechanism (illustrated as the adjustment pin 390 and the embodiment shown in FIG. 17) that can enable adjustment of the rotational orientation of the bevel 360 relative to the housing 102. However, other embodiments can be provided that eliminate the rotational adjustment component 370, thereby simplifying the drive assembly and needle assembly and permitting the operator to exercise rotational control of the entire inserter during the procedure by rotating the inserter as a unit.

For example, FIGS. 20-23B illustrate an embodiment of an inserter 400 in which the rotational adjustment of the needle relative to the housing 102 has been removed. Thus, although the drive assembly and other components of the inserter 400 can be configured substantially the same as the other respective components of the inserter 100 discussed in FIGS. 1-16D, the inserter 400 demonstrates a simplified design that does not use a rotational adjustment mechanism for the needle assembly 104. As shown FIG. 20, the inserter can comprise the housing 402 a needle assembly 404, and a slider component 410. The needle assembly 404 can comprise a needle mount 412 that can be coupled to a needle driver 414 such that the needle driver 414 and the needle mount 412 have a substantially fixed rotational and longitudinal engagement. Therefore, longitudinal movement of the needle driver 414 along the longitudinal axis will be transferred directly to the needle mount 412. Further, the needle mount 412 will not tend to rotate relative to the needle driver 414 about the longitudinal axis of the inserter 400. Other features and components of the inserter 400 are identical to those discussed above with respect to the inserter 100 and will not be repeated here for brevity.

Figure 23A:
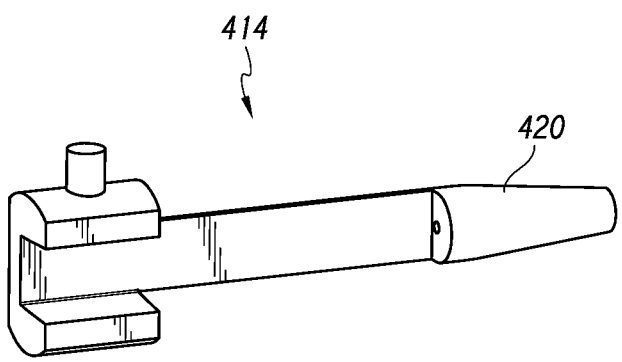
FIGS. 23A and 23B are perspective views of a needle driver of the inserter shown in FIG. 20, according to some embodiments.
Figure 23B:
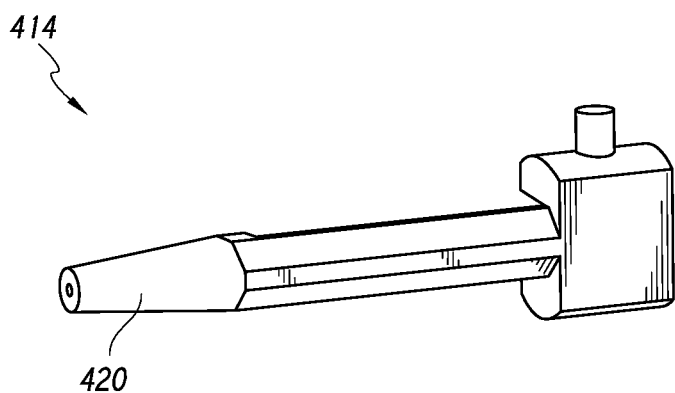

FIGS. 23A and 23B illustrate the needle driver 414 of the inserter 400. Some features of the needle driver 414, such as the proximal portion and the protrusion, are the same as the needle driver 164 discussed above. However, the distal portion of the needle driver 414 features an engagement surface 420 configured to engage with the needle mount 412 in order to fix the longitudinal and rotational orientation of the needle driver 414 relative to the needle mount 412. Thus, a rotational adjustment component is omitted.

Inserter with Dual Actuation Mechanism

Figure 24:
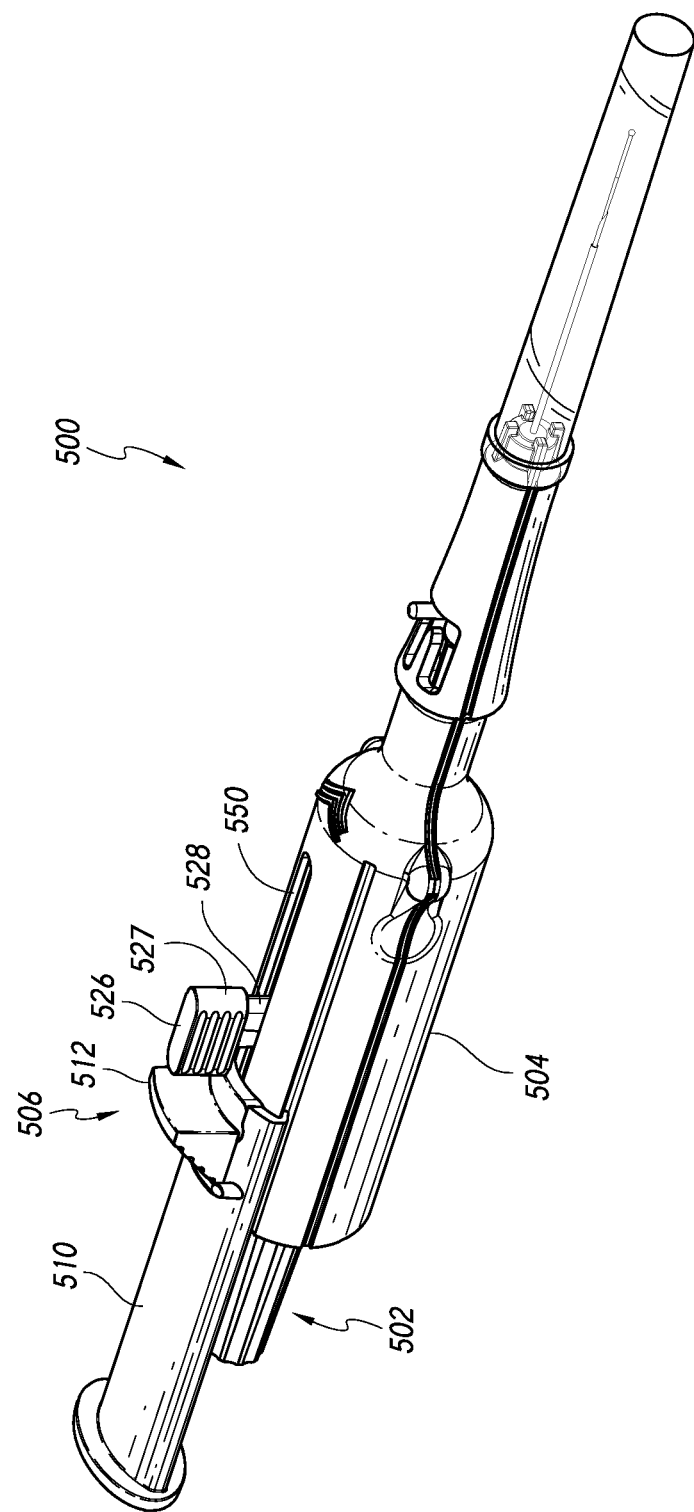
FIG. 24 is a perspective view of yet another inserter, according to some embodiments.
Figure 25:
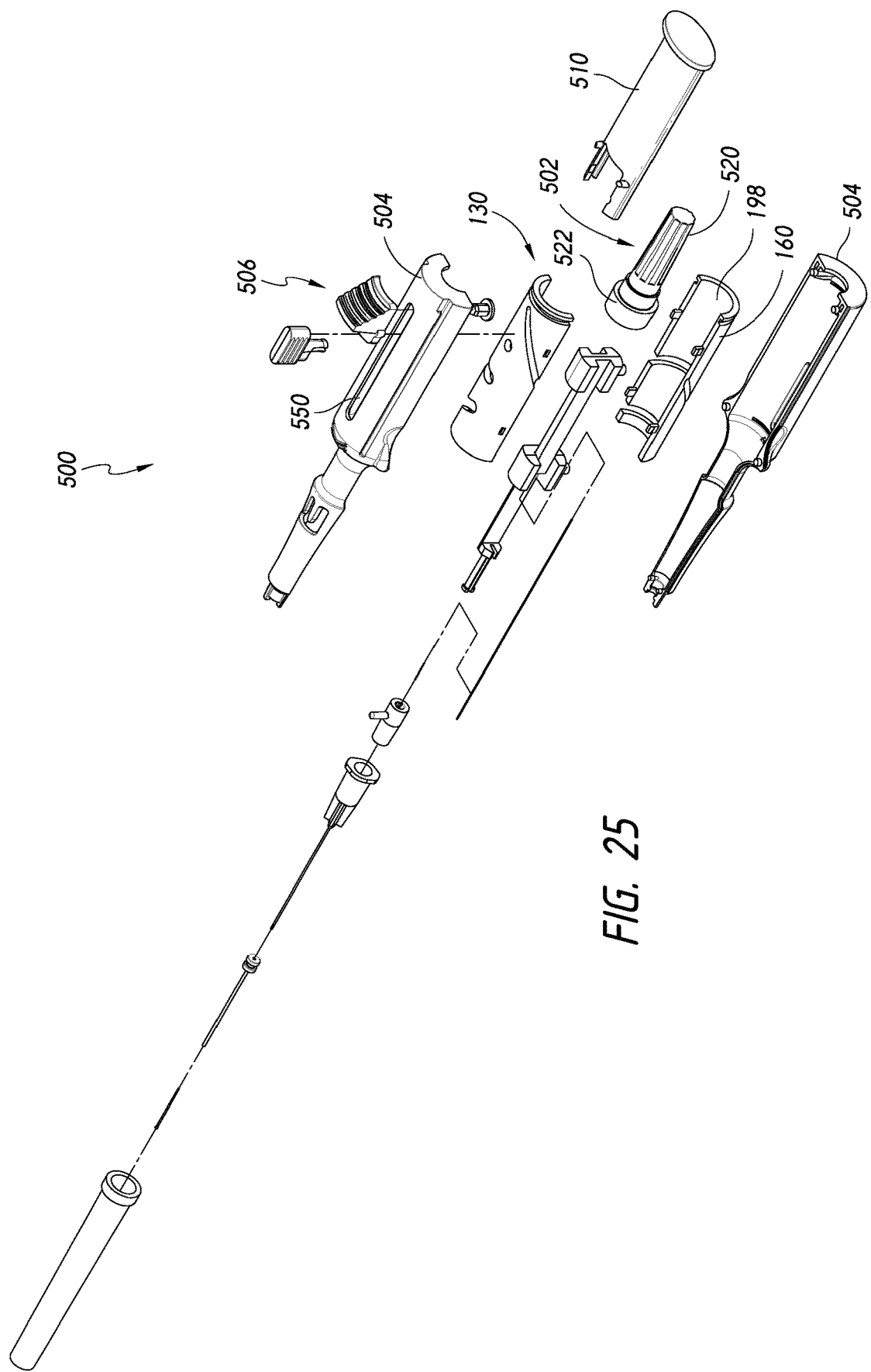
FIG. 25 is a perspective, exploded view of the inserter shown in FIG. 24, according to some embodiments.

Referring now to FIGS. 24-29, another embodiment of an inserter and alternative features of an inserter will now be described. FIGS. 24-25 illustrate an inserter 500 having a rotational mechanism 502 that is coupled to the housing 504 of the inserter 500. The rotational mechanism 502 can be used as an alternative means for rotating the drive component 160 of the drive assembly 130. Nevertheless, the inserter can also comprise a slider component 506, which can function in a manner identical to the slider component 106 of the inserter 100 discussed above and provide a means for rotating the drive component. Other features and functions of the inserter 500 can be similar or identical to those of the inserter 100 and will not be repeated here for brevity.

The rotational mechanism 502 can comprise an actuator portion 520 and an engagement portion 522. The engagement portion 522 can be configured to be positioned within the housing and engage with a portion of the drive assembly 130. For example, the engagement portion 522 can comprise an outer surface that engages with the guide surface 198 of the drive component 160. In some embodiments, the engagement portion 522 can be adhesively attached or secured to the guide surface 198. However, in some embodiments, the engagement portion can be mechanically or frictionally engaged with the guide surface 198.

The engagement between the rotational mechanism 502 and the drive component 160 enables the operator to rotate the drive component 160 by manually rotating the actuator portion 520 of the rotational mechanism 502. In this manner, instead of and/or in addition to actuation of the drive assembly 130 using the slider component 506, the operator can manually rotate the rotational mechanism 502 in order to facilitate rotation of the drive component 160. Such an embodiment can allow an operator to either use the longitudinal motion of the slider component 506 to actuate the inserter 500 and/or use the rotational actuation via the rotational mechanism 5022 actuate the inserter 500.

FIGS. 26A and 26B illustrate initial and final positions of the plunger driver 162 and the needle driver 164 in response to actuation of the rotational mechanism 502. The result of actuating the drive assembly 130 to move from the initial position shown in FIG. 26A to the final position shown in FIG. 26B, and the interaction between the drive component 160 and the plunger driver 162 and the needle driver 164 is identical to that of the inserter 100 and will not be repeated here for brevity.

In some embodiments, the slider component 506 can also comprise a slider handle 510. The slider handle 510 can be coupled to the radially protruding knob 512 of the slider component 506 (similar to the slider component 106 of the inserter 100). The slider handle 510 can provide a greater physical area to facilitate grasping or exertion of force against the slider component 506. Thus, instead of using merely a finger or fingers to actuate the knob 512, the slider component 506 can be actuated via the slider handle 510 using a palm of the hand or otherwise.

FIGS. 27A and 27B illustrate the position of the shunt 300 within the needle component 120 and relative to the sleeve 124 when the inserter 500 is in the initial position of FIG. 26A and the final position of FIG. 26B, respectively. The movement and function of the plunger 122, the needle component 120, and the sleeve 124, as well as the resultant movement of the shunt 300 can be substantially identical to the function and movement of these components in the inserter 100.

Figure 28A:
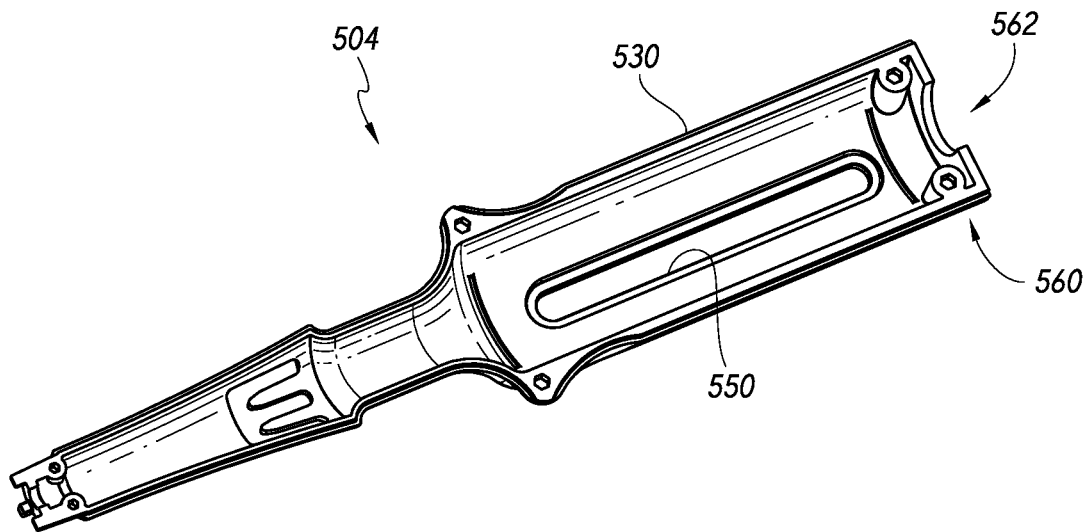
FIGS. 28A and 28B are perspective views of first and second halves of a housing of the inserter shown in FIG. 24, according to some embodiments.
Figure 28B:
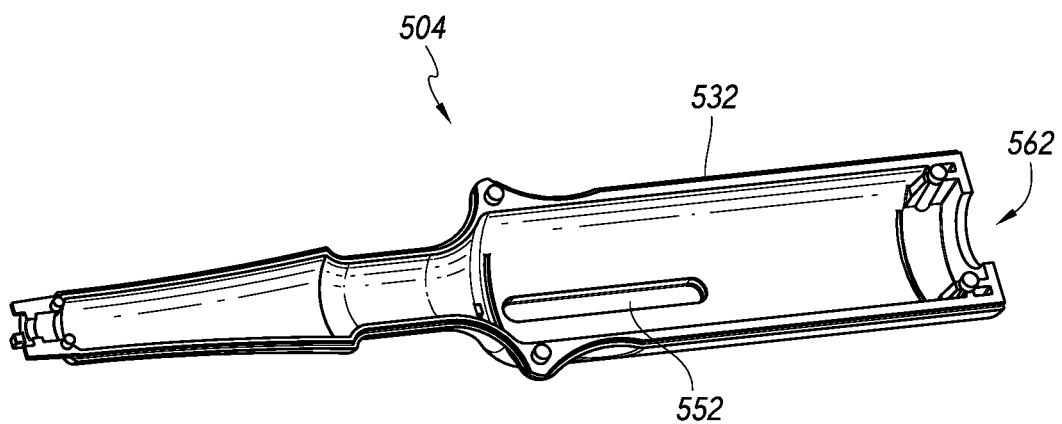

FIGS. 28A and 28B illustrate the housing 504 of the inserter 500. FIG. 28A illustrates a first portion 530 of the housing 504, and FIG. 28B illustrates a second portion 532 of the housing 504. Similar to the housing 102 of the inserter 100, the housing 504 can include grooves that correspond with and facilitate engagement between movable protrusions of the drive assembly and the housing 504.

Figure 29:
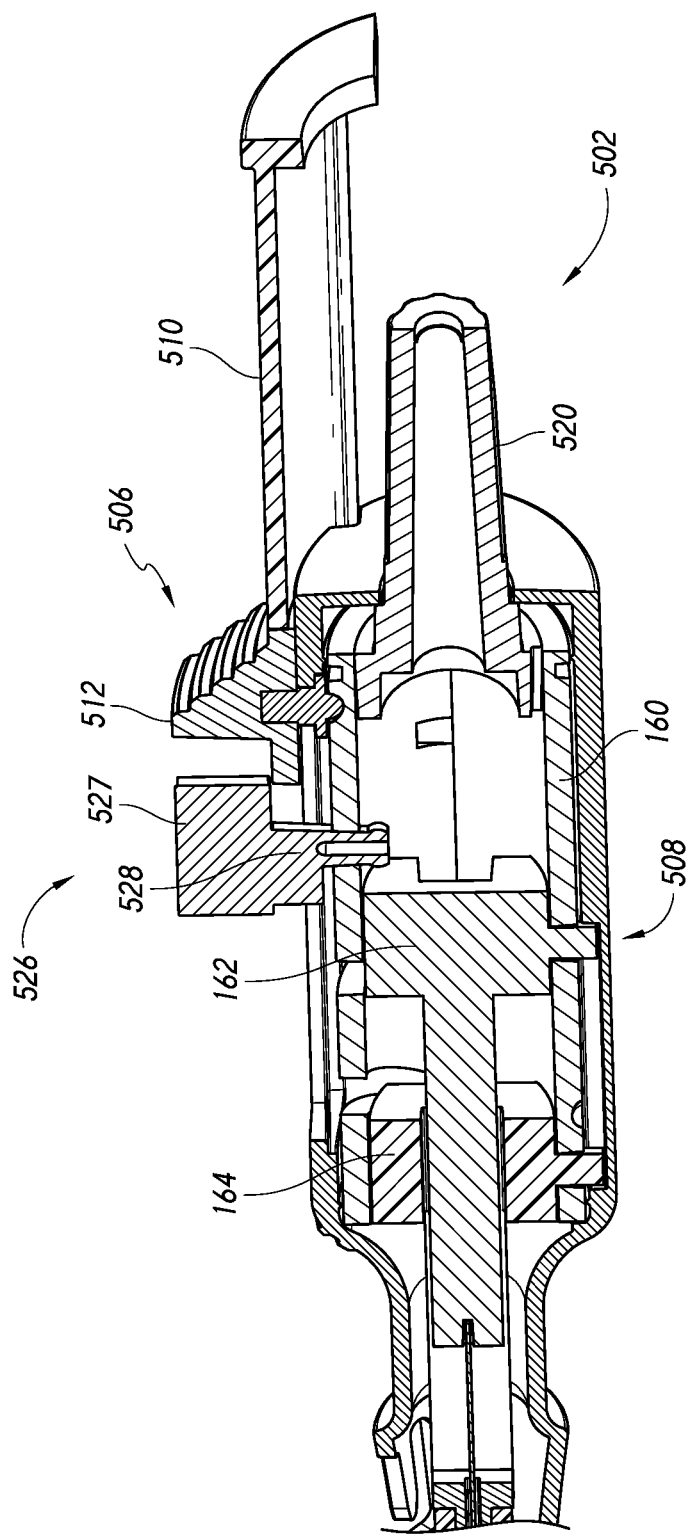
FIG. 29 is a perspective, cross-sectional view of the inserter of FIG. 24, according to some embodiments.

For example, FIG. 28A illustrates a guide slot 550 that can permit a protrusion of the slider component to extend through the housing and engage with the drive assembly 130. Further, the second portion 532 of the housing 504 can comprise a groove 552 that corresponds with the protrusions of the plunger driver 162 and the needle driver 164 and can provide the same advantages as discussed above with respect to the inserter 100. Additionally, the housing 504 can comprise a proximal end 560 that comprises an aperture 562 that extends therethrough in a longitudinal direction. The aperture 562 can be formed collectively by cutouts in the first and second portions 530, 532 of the housing 504. As generally shown in FIGS. 25-26B, the engagement portion 522 can be positioned within the housing 504 and a section of the rotational mechanism 502 can extend through the aperture 562 such that the actuator portion 520 can be readily grasped by the operator. FIG. 29 illustrates the positioning of the rotational mechanism 502 and the other components of the present embodiment.

The inserter 500 can also comprise a locking component 528. The locking component 528 can comprise a head portion 527 and an engagement portion 528. The engagement portion 528 can extend through the slot 550 of the housing 504. The engagement portion 528 can be coupled to a portion of the drive component 160 such that the slider component 506 is unable to move distally through the slot and/or the drive component 160 is unable to rotate relative to the housing 504. However, the locking component 526 can be removed from engagement with the drive component 160, thereby permitting rotational movement of the drive component 160 relative to the housing 504. Therefore, longitudinal or rotational actuation of either the slider component 506 and/or the rotational mechanism 502 can be initiated, thereby actuating the functions of the inserter 500.

Referring now to FIGS. 30A-32C, additional features can be incorporated into some embodiments of the inserter. In particular, some embodiments of the inserter can comprise different handle components that facilitate manual actuation of the inserter. However, in some embodiments, a spring or motor driven mechanism can be incorporated into the inserter in order to facilitate actuation of the inserter without requiring longitudinal motion of a slider component.

Initially, referring to FIGS. 30A and 30B, an embodiment of an inserter 600 is shown that comprises a handle component 602 that is coupled to a knob 604 of the slider component 606. Other features and aspects of the inserter 600 can be configured to be identical or similar to the inserter 100. However, the handle component 602 can be configured to encircle, surround, or enclose a proximal end of the inserter 600. Upon actuation of the handle component 602, the handle component 602 can be positioned over increasingly more of the housing 102 of the inserter 600.

Alternative Inserter Handle Designs and Features

FIG. 30A illustrates the handle component and a first position 610, and FIG. 30B illustrates the handle component in a second position 612. Similar to the discussion above with respect to FIGS. 26A and 26B, the movement and function of the inserter 600 can be similar or identical to the movement and function of the inserter 100 when the handle component 602 is moved from the first position 610 to the second position 612.

The configuration of the handle component 602 can tend to enable an operator to more easily grasp and/or actuate the inserter 600 and the slider component 606. Similar to the inserter 500, the inserter 600 can also comprise a locking component 620 that can extend through the slot and engage the drive component of the drive assembly positioned within the housing 102. When the locking component 620 is removed, the handle component 602 can be actuated and moved distally from the first position 610 toward the second position 612.

The function and operation of the locking component 620 can be identical to the function and operation of the locking component 526 and will not be discussed here for brevity.

In some embodiments, the mechanical or electrical actuation of the drive assembly can permit discrete steps or movements of the components that can be performed separately. For example, the step of advancing the plunger driver can be performed and further motion of the drive assembly can cease until and unless the operator initiates a new movement or presses an actuator button to begin a further step. Each step can require additional operator action. However, all steps of the process can also be performed after a single motion or a single actuation of a button.

Additionally, in some embodiments, the inserter can comprise one or more lights (or one or more colored indicators) that can visually indicate a stage of the process or that an inserter component is currently undergoing a movement.

Powered Inserter Drive Assemblies

Figure 31:
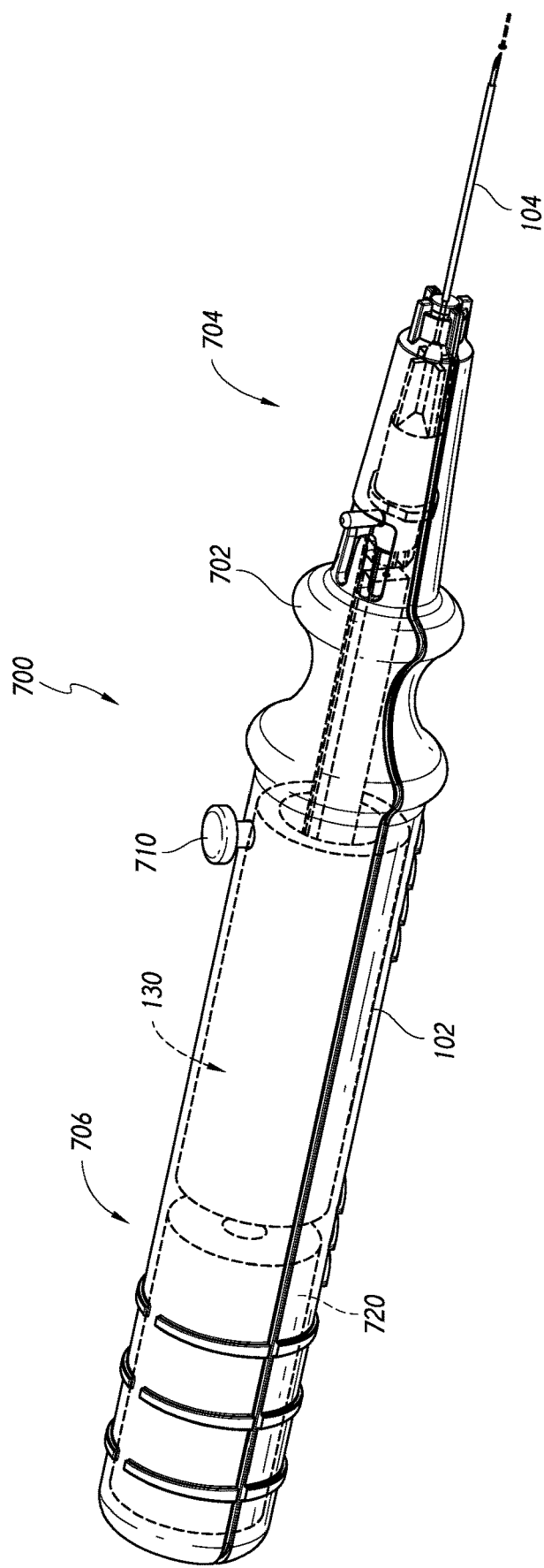
FIG. 31 is a perspective view of yet another inserter, illustrating a drive assembly for the drive assembly, according to some embodiments.
Figure 32A:
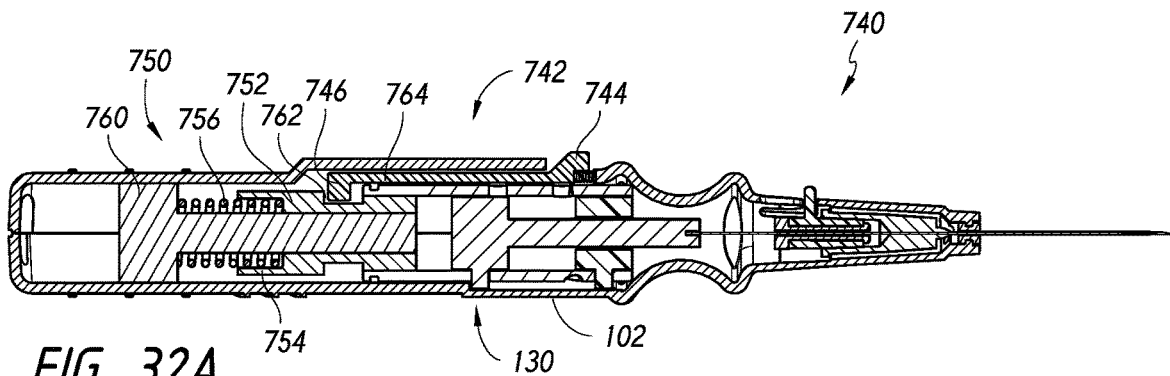
FIGS. 32A-32C are side, cross-sectional views of button-actuated, spring-loaded drive assemblies for an inserter, according to some embodiments.
Figure 32B:
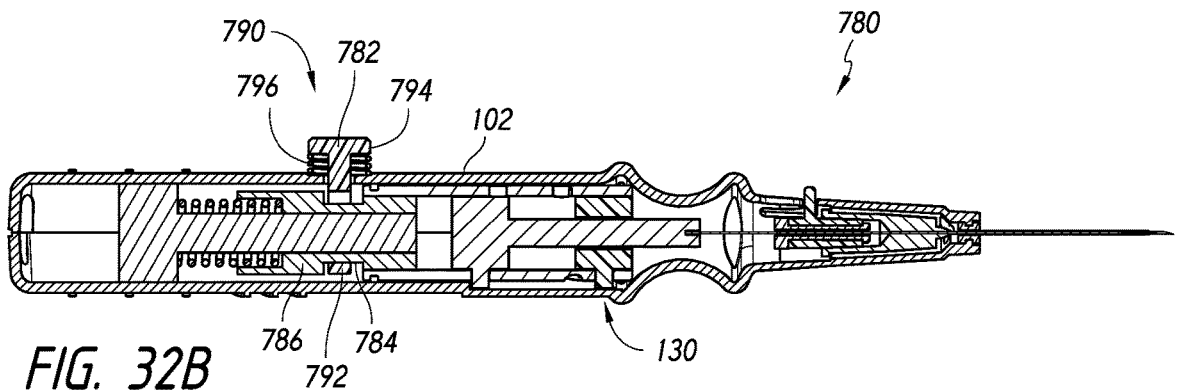
Figure 32C:
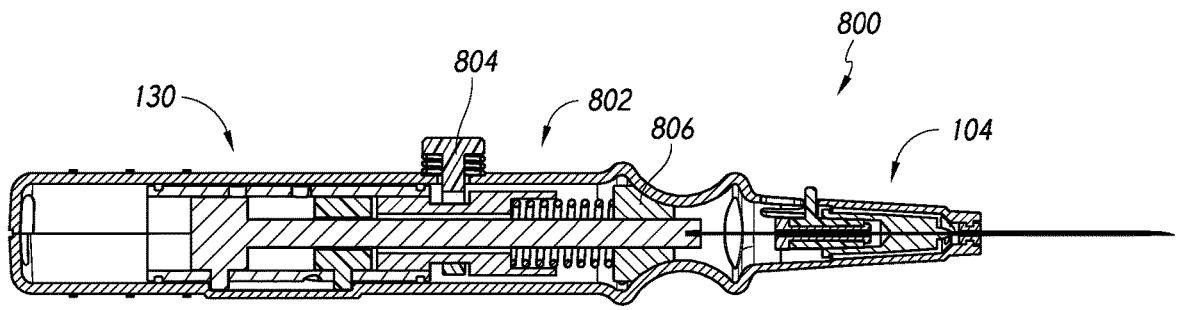

FIGS. 31-32C illustrate additional embodiments of the inserter that are powered, e.g., in which a mechanical force other than or in addition to a force exerted by the operator can be implemented to actuate the drive assembly of the inserter. The rotational force exerted on the drive assembly can be derived from either an electrical motor or one of a variety of mechanical systems that can control rotational movement of the drive assembly of the inserter.

FIG. 31 illustrates an inserter 700 that comprises a housing 702 and a needle assembly 704 that can be actuated using a drive assembly 706 that is disposed within the housing 702. The drive assembly 706 can comprise a button 710 that can actuate rotational movement of the drive component of the drive assembly 130 (which can be the same as the drive assembly illustrated in the inserter 100). The drive assembly 706 can be powered. For example, the drive assembly 706 can comprise an electrical motor that has a drive output that allows a needle assembly 704 attached to the inserter 700 to be actuated in in a manner such as that disclosed above.

The inserter 700 shown in FIG. 31 can be configured to provide a motor-driven drive assembly 706 that allows an operator to actuate motion of the needle assembly 704 using a single button 710. The drive assembly 706 can comprise a drive motor 720. The drive motor 720 can comprise an electrical motor that provides a rotational force to one or more components or provides a longitudinal force to one or more components. For example, the drive motor 720 can provide a longitudinal distal force to the plunger and a proximal retracting force to the needle. The drive motor 720 can actuate one or more, such as to, three, or more components and provide a driving force in either a distal or proximal direction.

In some embodiments, the drive assembly 706 can be removably coupled to a given needle assembly 704 in order to enable the drive assembly 706 to be a reusable component of the inserter 700. For example, the inserter 700 can be separable such that a removable portion of the inserter 700 (such as the drive assembly 130 and/or the needle assembly 704) can be replaced after being used.

Any of the embodiments disclosed herein can be implemented such that the inserter is part of a kit having replaceable drive assemblies and/or the needle assemblies in order to facilitate reuse of a portion of the inserter. In such embodiments, the reusable portion of the inserter could be custom fit (e.g., size, length, cross-section, or ergonomically) to a given operator's hand or based on an operator's preference to ensure maximum comfort and control of the inserter during use. However, any of the embodiments disclosed herein can also be configured as single-use devices.

Referring now to FIGS. 32A-32C, different embodiments of the inserters are illustrated that use a spring-loaded force to drive rotation of the drive component. These embodiments also illustrate inserters that comprise a push-button actuation mechanism. As noted above with respect to FIG. 31, some embodiments of the drive assembly can comprise an electrical motor that provides a driving force to the needle assembly to actuate the inserter. In the embodiments of FIGS. 32A-32C, the drive assembly can be driven using spring force. For example, as shown in FIGS. 32A-32C, the drive assembly can comprise a spring that can be preloaded in order to selectively drive motion of one or more components of the inserter.

FIG. 32A illustrates an inserter 740 that comprises a drive assembly 742. The drive assembly 742 can comprise an actuator button 744 that can be moved in a longitudinal direction along the longitudinal axis in order to disengage a stop member 746 from a rotational drive motor 750. The drive motor 750 can comprise an output component 752 coupled to the drive assembly 130. The output component 752 can be rotatable within a housing 102 of the inserter 740. The output component 752 can comprise a proximal end 754 that is coupled to a drive spring 756. The drive spring 756 can comprise a proximal end that is coupled to a base 760. The drive spring 756 can be preloaded or wound such that the drive spring 756 exerts a rotational or torsional force against the proximal end 754 of the output component 752. However, engagement between the stop member 746 and a brake portion 762 of the output component 752 can restrict or prevent rotational movement of the output component 752. The preloaded drive spring 756 can be permitted to drive motion of the output component 752 (and therefore the drive assembly 130) only when the operator moves the actuation button 744 in a distal direction, which results in the stop member 746 being released from engagement with the brake portion 762.

In some embodiments, the actuation button 744 and the stop member 746 can be formed on opposing ends of an actuation member 764. The actuation member 764 can be longitudinally movable relative to the housing 102. Engagement between the stop member 746 and the brake portion 762 of the output component 752 can be a frictional engagement. In some embodiments, engagement between the stop member 746 and the brake portion 762 of the output component 752 can be a mechanical engagement between complementary structures of the stop member 746 and the brake portion 762. For example, the stop member 746 can comprise one or more protrusions or grooves that can engage with one or more corresponding grooves or protrusions of the brake portion 762. The stop member 746 can comprise a tooth that can engage with one of a plurality of teeth formed in the brake portion 762. Accordingly, when the actuation button 744 is moved in a distal direction, the actuation member 764 can be moved distally, thereby separating the stop member 746 from the brake portion 762 and disengaging the stop member 746 such that the output component 752 is permitted to rotate. Such actuation can permit completion of only a single step of the shunt deployment process (thus requiring multiple pushes of the button 744 to complete the process) or completion of all steps of the process (thus requiring only a single push of the button 744).

Rotation of the output component 752 can drive or result in rotation of the drive assembly 130 of the inserter 740. The drive assembly 130 can be configured to provide the same function and features as the drive assembly of the inserter 100 described above. Accordingly, the details and function of its components are not repeated here for brevity. Therefore, the inserter 740 can have a single button actuation mechanism that is spring-driven and allows incremental actuation and movement of the drive assembly 130 of the inserter 740.

Other embodiments of a spring-driven drive assembly can also be implemented. For example, FIG. 32B illustrates an inserter 780 that comprises an actuation member 782 that can selectively engage a brake portion 784 of an output component 786 of a drive assembly 790 of the inserter 780. Similar to the embodiment discussed above in FIG. 32A, the inserter 780 can use a preloaded spring that drives rotation of the output component 786. The rotation of the output component 786 can be restricted by contact between the actuation member 782 and the brake portion 784. However, in the embodiment shown in FIG. 32B, the actuation member 782 uses radial engagement or engagement by which the brake portion 784 of the drive assembly 790 moves in a radial direction. This radial engagement contrasts with the longitudinal engagement between the actuation member 764 and the brake portion 762 in which the brake portion 762 moves along the longitudinal axis (FIG. 32A). Thus, the inserter 780 can incorporate a radially actuated push button drive assembly that allows an operator to selectively actuate one or more functions or steps of motion of the drive assembly of the inserter 780.

In order to provide radial engagement with the brake portion 784, the actuation member 782 can comprise a stop member 792 that extends from the actuation member 782. In some embodiments, the actuation member 782 can comprise a circular ring or a portion thereof that extends from an actuator button 794. The actuation member 782 can comprise a full or partial ring. The actuation member 782 can circumferentially traverse or extend across the output component 786 such that the stop member 792 is positioned on an opposing position relative to the actuator button 794.

In some embodiments, the output component 786 can comprise a generally circular cross-section at the brake portion 784 thereof that can engage with the stop member 792 of the actuation member 782. As illustrated in FIG. 32B, the stop member 792 can be positioned at a bottom end of the circular cross-section of the output component 786 while the actuator button 794 can be positioned at an opposing, top end of the circular cross-section. The actuation member 782 can be biased towards an engaged position (shown in FIG. 32B) by virtue of a spring 796 that acts against the actuator button 794. The spring 796 can push against the housing 102 and a bottom or driven surface or structure of the actuator button 794. Thus, the spring 796 can provide a radial force that pushes the actuator button 794 in a direction away from the output component 786 such that the stop member 792 is forced into engagement with the brake portion 784, as shown in FIG. 32B.

The engagement between the stop member 792 and the brake portion 784 can be overcome by compressing the actuator button 794 toward the housing 102, thereby overcoming the force of the spring 796. The engagement between the stop member 792 and the brake portion 784 can be overcome by depressing the actuation member 782, which can result in rotation of the output component 786 and consequent motion of the drive assembly 130. Other features and components of the drive assembly 790, including the base and the drive spring, as well as friction or mechanical engagement between the stop member 792 and the brake portion 784, can be implemented as described above with respect to the embodiment of the inserter 740 shown in FIG. 32A. Accordingly, that discussion is not repeated here for brevity.

While the embodiments shown in FIGS. 32A and 32B illustrate alternative engagement modes for a spring-loaded drive assembly and actuation thereof, FIG. 32C illustrates an alternative configuration in which the drive assembly of the inserter is positioned distally relative to the drive assembly, in contrast to the configurations illustrated in FIGS. 32A and 32B.

FIG. 32C illustrates an inserter 800 that can comprise a drive assembly 802 that uses the same radial actuation as in the embodiment illustrated in FIG. 32B. However, in contrast to the embodiment shown in FIG. 32B, the drive assembly 802 can be positioned intermediate the drive assembly 130 and the needle assembly 104. Such an arrangement can provide an inserter configuration using radial engagement to have an actuation button 804 that is positioned closer to the distal end of the inserter 800 when compared to the inserter 780. Thus, various embodiments of the inserter can be implemented to position the actuation button in a variety of locations.

In order to position the drive assembly 802 distally relative to the drive assembly 130, the configuration and longitudinal length of the drive components of the drive assembly 130 can be modified. For example, the plunger driver and the needle driver can be longitudinally longer than the plunger driver and the needle driver of the embodiments shown in FIGS. 32A and 32B. Further, a base 806 of the drive assembly can comprise an aperture or central opening through which the drive components of the drive assembly 130 can pass. Other features and modifications of the inserter 800 can be similar to those described above with respect to the inserters 740 and 780 and will not be repeated here for brevity.

In any of the embodiments illustrated in FIGS. 32A-32C, the drive component of the drive assembly 130 can be modified to comprise a brake portion for engagement with a stop member. Further, the drive component can also be coupled directly to the drive spring. Accordingly, some embodiments can be implemented that do not use an output component. Further, the base, against which an end of the spring is coupled, can be a structure formed on an interior of the housing.

Implant Retention Device

In accordance with some embodiments, an implant retention device can be provided that facilitates retention of a shunt within the needle of the inserter during transport and shipping of the inserter or the needle assembly. Thus, the inserter can be used in combination with a shunt retention device that engages with a needle of the inserter in order to prevent the shunt from exiting the needle accidentally.

Figure 33:
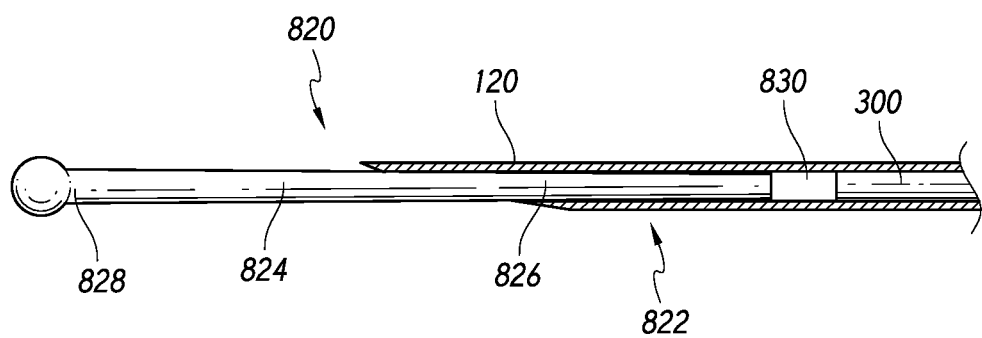
FIG. 33 is a side, cross-sectional view of an implant retention device received within a needle lumen of an inserter, according to some embodiments.

For example, FIG. 33 illustrates a distal end of an inserter in which a needle component 120 carries a shunt 300. The shunt retention device 820 can engage with a distal end 822 of the needle component 120. The retention device 820 can comprise an elongate body 824 that comprises a first portion 826 and a second portion 828. The first portion 826 can taper from a larger diameter cross-section to a smaller diameter cross-section. The smaller diameter cross-section can be less than an inner diameter of the distal end 822 of the needle component 120. Thus, the first portion 826 can be inserted into a lumen 830 of the needle component 120.

The elongate body 824 can be configured such that the tapering of the first portion 826 provides the elongate body 824 with a variable diameter cross-section. The diameter can taper gradually or in steps.

As shown in the embodiment illustrated in FIG. 33, the cross-section adjacent to the second portion or end 828 can be greater than the cross-section near the first portion 826. The cross-sectional diameter of the elongate body 824 can increase from a diameter that is less than an inner diameter of the lumen 830 of the needle component 120 to a diameter that is greater than the inner diameter of the lumen 830. Thus, the elongate body 824 can be inserted into the lumen 830 of the needle component 120 and advanced to a position at which the cross-section of the elongate body is about equal to the inner diameter of the lumen 830, thus restricting further advancement of the retention device 820 into the lumen 830.

In some embodiments, the elongate body 824 can frictionally engage with the distal end 822 of the needle component 120. For example, the retention device 820 can be force fit into the needle component 120 to create a frictional engagement between the outer surface of the elongate body 824 and an inner surface of the lumen 830. This frictional engagement can be overcome by exerting a withdrawal force on the second portion 828 of the retention device 820, thereby pulling the retention device 820 out of the lumen 830.

Although the retention device 820 is illustrated as having a circular or diametrical cross section, other cross sections can also be used, such as triangular, square, rectangular, polygonal, star-shaped, or other similar profiles. Further, the retention device 820 can be made of steel. In accordance with some embodiments, the device 820 may only contact the inside of the needle bevel, and therefore advantageously does not affect the needle sharpness, which is driven by the needle outside edges.

The retention device 820 can therefore ensure that the shunt 300 does not inadvertently fall out of or become exposed from the needle component 120. Such a device 820 can ensure that this shunt 300 is protected and not damaged during shipment or initial handling of the inserter or needle assembly. When the operator is prepared to implant the shunt 300, the retention device 820 can be withdrawn from the needle component 120 and the procedure can be carried out.

Shunt Implantation Procedures

FIGS. 34A-39 illustrate various procedures that can be performed in accordance with some embodiments disclosed herein. Such procedures can enable an operator to position an outlet end of an intraocular shunt within an area or region of lower pressure within the eye while leaving an inlet end of the shunt in fluid communication with the anterior chamber of the eye. In accordance with some embodiments, a procedure for creating a space for initial advancement of a shunt distal end into the eye, by "tenting" a more superficial layer of the eye (e.g., the conjunctiva or other layer, such as the intra-Tenon's adhesion layer) away from a deep layer of the eye (e.g., the sclera or other layer, such as intra-Tenon's adhesion layer) in an outflow area of the eye, can greatly facilitate initial placement and advancement of the shunt. Through such a procedure, the distal end of the shunt can be protected during advancement into the eye and the integrity of the shunt can be preserved. In contrast, prior methods in which a shunt was simply pushed into the eye (e.g., into a subconjunctival, suprachoroidal, or sub-Tenon's space) could often damage the shunt by closing or breaking a distal portion of the shunt or by causing the shunt to become kinked or buckled due to the distal pushing force acting upon the proximal end of the stent while a distal end of the stent is being constrained by the conjunctiva and is unable to move out of the needle.

Figure 34A:
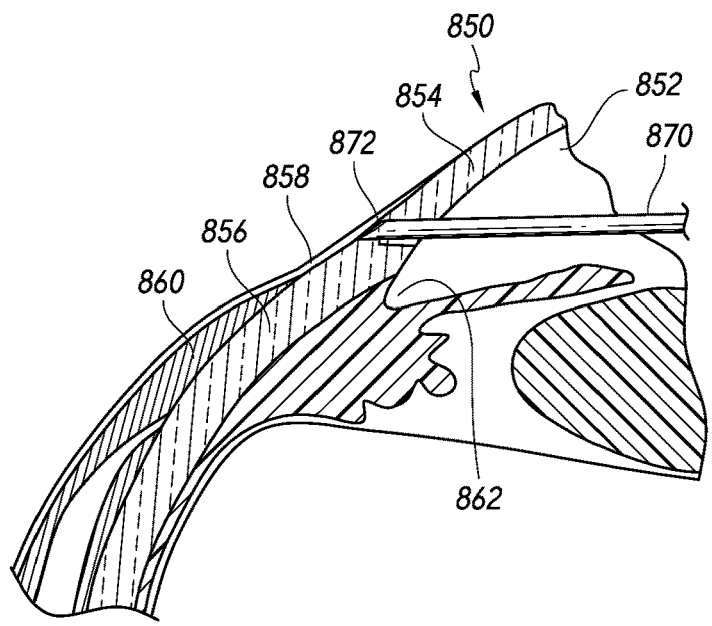
FIGS. 34A-34C are schematic views of a procedure for implanting an intraocular shunt, according to some embodiments.

For example, FIG. 34A illustrates an eye 850 having an anterior chamber 852, a cornea 854, sclera 856, conjunctiva 858, and intra-Tenon's adhesion space or layer 860. In accordance with an embodiment of a procedure for implanting an intraocular shunt, a needle 870 of an inserter can be introduced through the cornea into the anterior chamber 852 and positioned adjacent to the anterior chamber angle 862. The needle 870 can comprise a bevel 872. The bevel 872 can be moved through the anterior chamber 852 until the bevel 872 is positioned adjacent to the anterior chamber angle 862. When in position, the bevel 872 can be rotated or oriented such that the bevel extends generally parallel relative to the conjunctiva 858.

For example, as shown in FIG. 34A, the bevel 872 can be rotationally oriented such that a face of the bevel 872 or a plane through which the bevel face passes is aligned with or extends substantially parallel relative to a plane or surface through which the conjunctiva 858 passes. Before or during advancement of the needle 870 into the sclera 856, the operator can visually verify and adjust a rotational orientation of the bevel 872 until the bevel face is substantially parallel with a plane or surface of the conjunctiva 858. When the bevel 872 reaches the conjunctiva-sclera interface or subconjunctival space (abutting the conjunctive 858), the bevel face can be positioned adjacent to, against, or substantially coincident with a conjunctival plane, as shown in FIG. 34A.

Figure 34B:
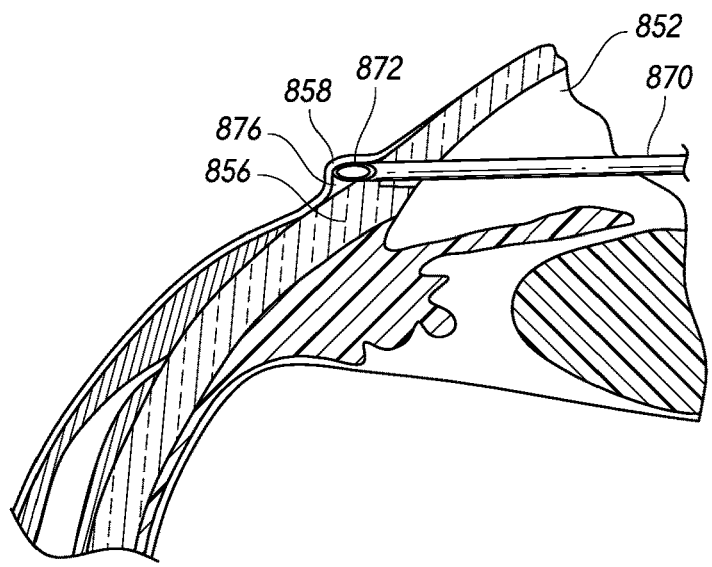

After achieving the position illustrated in FIG. 34A, the operator can rotate the needle 870 until the bevel 872 begins to push the conjunctiva 858 away from the sclera 856, as shown in FIG. 34B. This procedure, which can be referred to as "tenting" the conjunctiva 858, can create a small space or gap between the conjunctiva and the sclera adjacent to the bevel of the needle 870. Once a space 876 has been created by tenting the conjunctive 858, a shunt 300 can be advanced into the space 876 from the needle 870. As a result, the shunt 300 can be substantially easier to push into the space 876 because the conjunctiva 858 has been pushed away and is not immediately obstructing the advancement of the shunt 300 into the subconjunctival space.

Figure 34C:
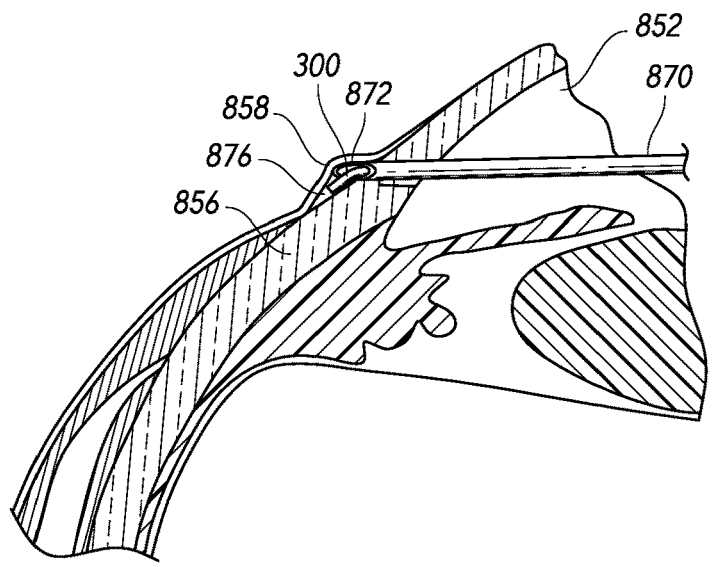
Figure 35A:
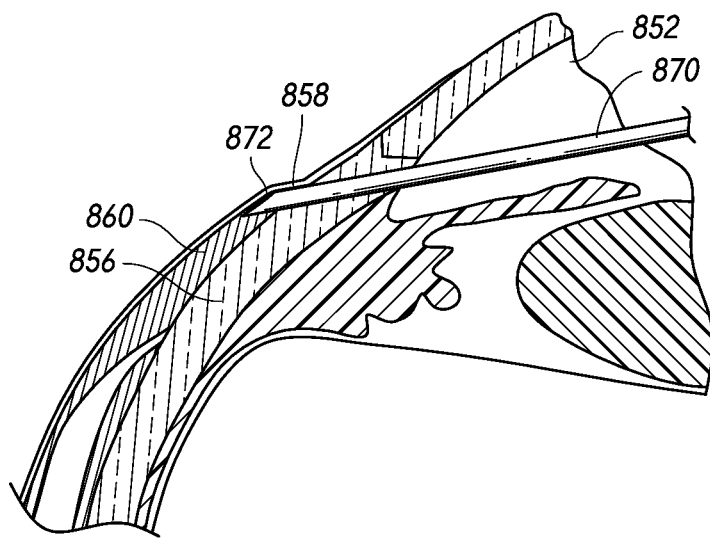
FIGS. 35A-35C are schematic views of another procedure for implanting an intraocular shunt, according to some embodiments.
Figure 35B:
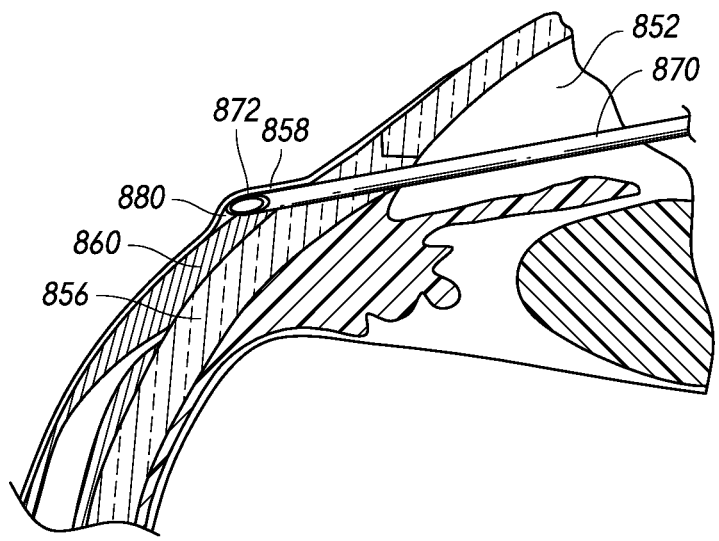
Figure 35C:
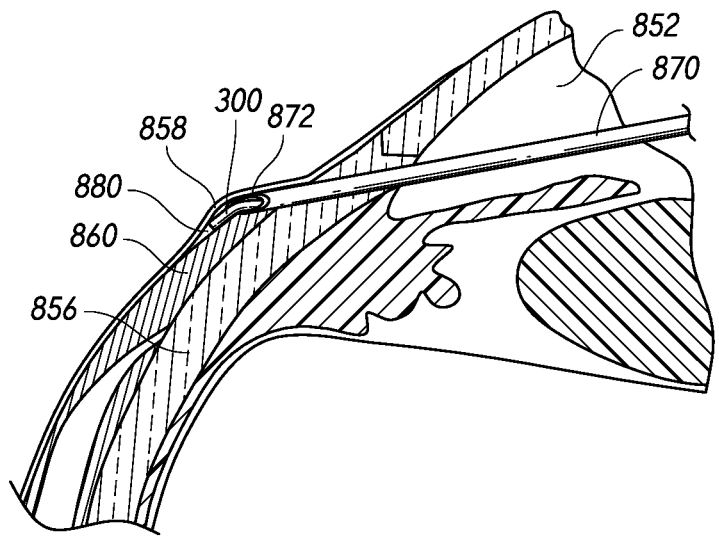

FIGS. 34A-34C illustrate placement of a shunt using the tenting procedure into a subconjunctival space 876 superficial to the sclera 856. FIGS. 35A-35C illustrate another tenting procedure that can be performed using the same steps as the tenting procedure illustrated and described with respect to FIGS. 34A-34C. However, the procedure illustrated in FIGS. 35A-35C is performed by tenting the conjunctiva 858 that lies superficial to the intra-Tenon's adhesion layer 860. As such, the needle 870 can be advanced at a different angle relative to that illustrated in FIGS. 34A-34C such that the bevel 872 of the needle 870 passes through the sclera 856 and exits the sclera 856 until the bevel 872 passes through a portion of the intra-Tenon's adhesion layer 860. Once the needle bevel 872 lies adjacent to the conjunctiva 858 above or superficial to the intra-Tenon's adhesion layer 860, as shown in FIG. 35A, the bevel 872 of the needle 870 can be rotated to create a space 880 between the conjunctiva 858 and the intra-Tenon's adhesion layer 860. The subconjunctival space 880 can then provide a gap or opening that allows a distal end of the shunt 300 to exit the needle 870 without providing substantial resistance to distal advancement of the shunt 300.

Figure 36A:
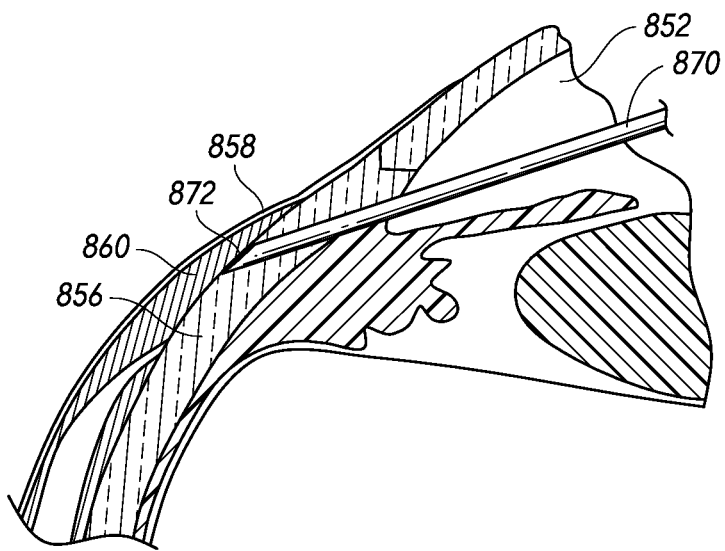
FIGS. 36A-36C are schematic views of yet another procedure for implanting an intraocular shunt, according to some embodiments.
Figure 36B:
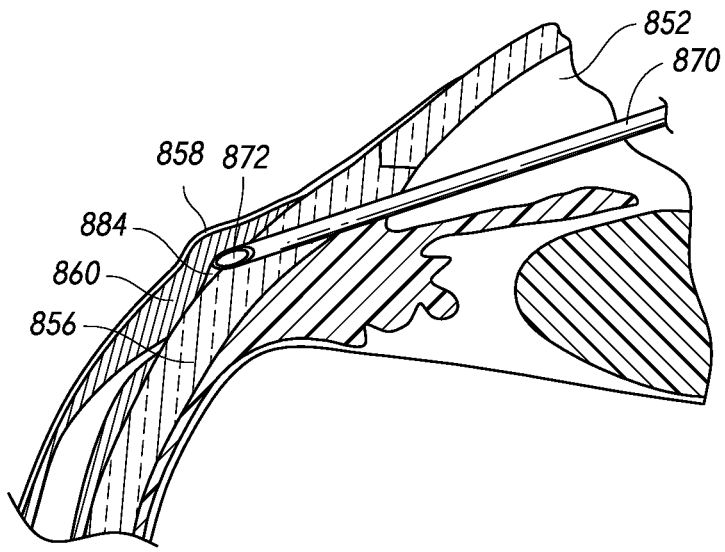
Figure 36C:
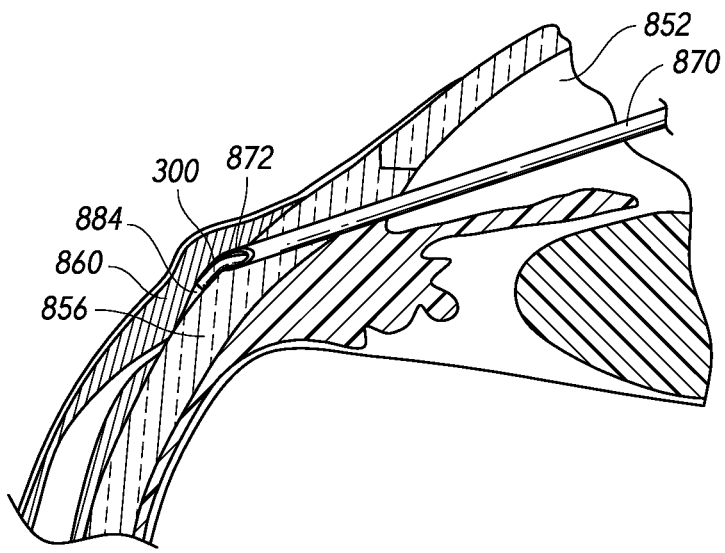

Similar to the embodiments of the tenting procedure shown in FIGS. 34A-35C, 36A-36C illustrates a procedure for tenting adjacent layers of an outflow area of the eye. The procedure can be performed similarly to those described above. However, as shown in FIG. 36A, the needle 870 is advanced until the bevel 872 reaches the interface between the sclera 856 and the intra-Tenon's adhesion layer 860. Thereafter, the bevel 872 can be rotated until the intra-Tenon's adhesion layer 860 is pushed away from the sclera 856 to create a space 884 between the intra-Tenon's adhesion layer 860 and the sclera 856. Thereafter, as shown in FIG. 36C, the shunt 300 can be advanced into the space 884.

In any of the above procedures, the bevel 872 can be rotated between about 10° and about 60° in order to "tent" a superficial layer relative to a deep layer. However, the needle can be rotated between about 25° and about 135°, between about 50° and about 120°, and between about 70° and about 110°, and in some embodiments, about 90°. Thus, various procedures can be performed in which a space is created between a superficial layer, such as the conjunctiva or the intra-Tenon's adhesion layer, and a deep layer, such as the sclera or the intra-Tenon's adhesion layer. The space created between the superficial and deep layers can be at any of a variety of locations relative to the anterior chamber 852. Thus, in performing the procedures, the operator can adjudge the optimal location for the space based on the desired outflow area to be achieved.

Figure 37:
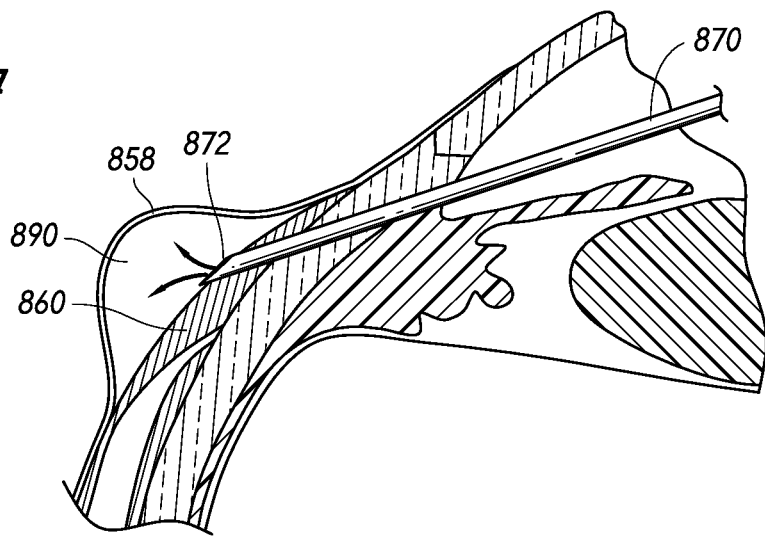
FIGS. 37-39 are schematic views of a preparatory procedure for implanting an intraocular shunt, according to some embodiments.
Figure 38:
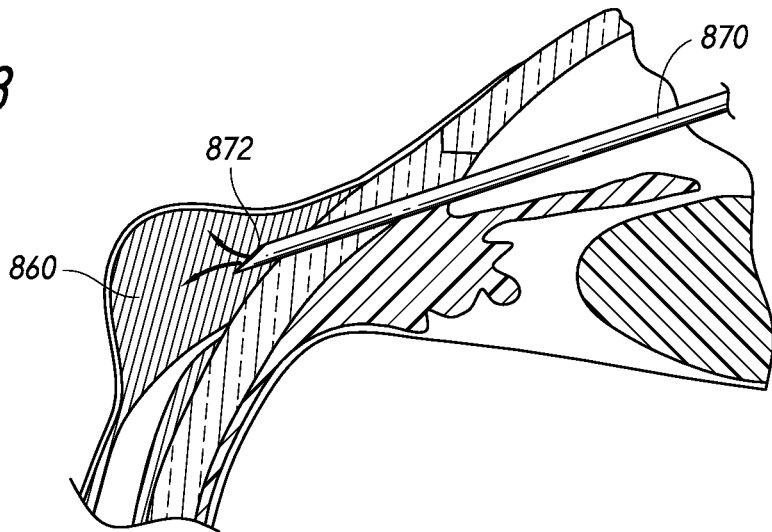
Figure 39:
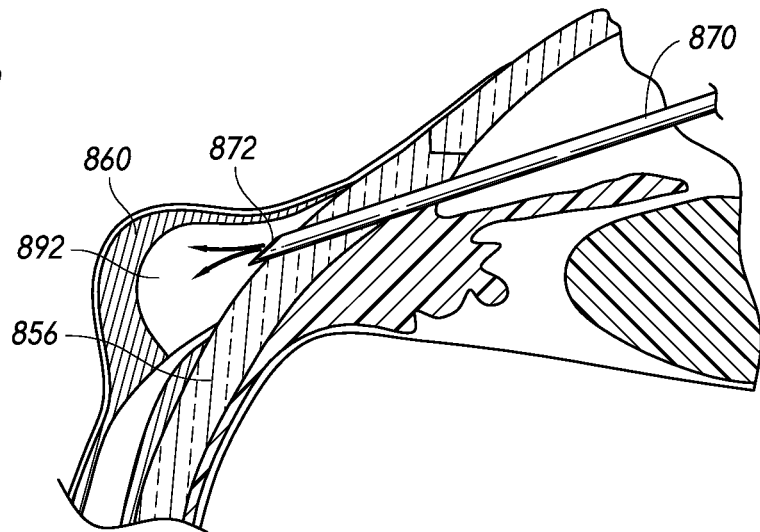

While the procedures and FIGS. 34A-36C illustrate procedures for tenting a superficial layer relative to a deep layer, the procedures illustrated in FIGS. 37-39 illustrate procedures in which a superficial layer can be separated from a deep layer or by which a target outflow area can be increased in size in order to facilitate advancement of the shunt into the target outflow area without damaging the shunt or needing to overcome substantial resistance. These goals and objectives are similar to those achieved using the procedures described above with respect FIGS. 34A-36C.

Referring to FIG. 37, a needle 870 is moved to a position similar to that shown in FIG. 35A, where the bevel 872 is positioned immediately deep to the conjunctiva 858 (shown in FIG. 35A as being superficial to the intra-Tenon's adhesion layer, the bevel 872 can also be positioned superficial to the sclera alone). In the illustrated embodiment, the bevel 872 can be positioned at an intersection, boundary, or interface of the conjunctiva 858 and the intra-Tenon's adhesion layer 860. When the bevel 872 is in position, fluid can be ejected from the needle 870 in order to fill or inflate a space 890 between the conjunctiva and the intra-Tenon's adhesion layer 860. As such, the space 890 can be created and maintained such that a shunt can be advanced into the space 890 to position an outflow end of the shunt within the space 890 without causing damage to the shunt or otherwise obstructing movement of the shunt.

The fluid used to inflate a space, as described in some embodiments, can comprise a balanced salt solution ("BSS"), a visoelastic material, water, or lidocaine, or equivalents thereof. For example, in some embodiments, a space created sub-Tenon's (between intra-Tenon's adhesion layer and the sclera) can be filled with a visoelastic. Further, in some embodiments, a space created in the intra-Tenon's adhesion layer can be filled with water.

Similarly, FIG. 38 illustrates a procedure in which a needle 870 is advanced until a bevel 872 is positioned within the intra-Tenon's adhesion layer 860. When the bevel 872 is positioned within layers of intra-Tenon's adhesion layer 860, such as between superficial and deep layers of the intra-Tenon's adhesion layer 860, fluid can be ejected from the needle 870 to result in expansion or swelling of the intra-Tenon's adhesion layer 860, thereby increasing the spacing within the intra-Tenon's adhesion layer 860. For example, such swelling can decrease the density of the intra-Tenon's adhesion layer 860 by causing adhesions (the structures that interconnect superficial and deep layers of the intra-Tenon's adhesion layer 860) to be further spaced apart from each other by increasing the spacing between adjacent adhesions or by stretching the adhesions to enable a distal end of the shunt to be advanced with reduced resistance than in an untreated area.

Yet another example of a procedure for creating a space between adjacent layers of a target region is shown in FIG. 39. In this figure, a needle 870 has been advanced until the bevel 872 is positioned at an interface or between the intra-Tenon's adhesion layer 860 and the sclera 856. As illustrated, fluid can be ejected from the needle 870 until a space 892 is created by inflating the interface between intra-Tenon's adhesion layer 860 and the sclera 856. Similar to the other procedures described above, the space 892 can be used to provide an initial area through which the distal end of the shunt can be advanced so that the shunt is not damaged and does not experience significant resistance when being advanced into the target outflow area.

These procedures, illustrated in FIGS. 34A-39, demonstrate various techniques by which an outflow space or outflow area can be prepared to receive an outflow end of a shunt so that the shunt is not damaged and/or the shunt experiences less resistance when being advanced into the target outflow area (compared to an untreated area). Other outflow regions, such as the suprachoroidal space, the intrascleral space, and others can be targeted using one or more of the techniques described herein. Further, some of the techniques can be combined (e.g., a superficial layer can be tented mechanically by rotation of the bevel and later inflated using fluid ejected from the needle). Other modifications and implementations of such methods can be performed by one of skill and are within the scope of the present disclosure.

Illustration of Subject Technology as Embodiments

The subject technology is illustrated, for example, according to various aspects described below. Various examples of aspects of the subject technology are described as numbered embodiments (1, 2, 3, etc.) for convenience. These are provided as examples and do not limit the subject technology. It is noted that any of the dependent embodiments may be combined in any combination, and placed into a respective independent embodiment, e.g., Embodiment 1 or Embodiment 5. The other embodiments can be presented in a similar manner.

Embodiment 1. An inserter for treating glaucoma, comprising: a housing having a distal portion, a proximal portion, a longitudinal axis extending between the distal and proximal portions, an interior cavity, and an elongate slot extending along an outer surface of the housing into the cavity; a needle, having a lumen, movably coupled to the distal portion along the axis; a plunger, disposed within the lumen, movable along the axis to result in an axial force on a shunt to urge the shunt distally relative to the needle; and a slider component coupled to the housing and slidable along the elongate slot, the slider component being engaged with the drive component such that distal movement of the slider component along the axis results in both (1) distal movement of the plunger along the axis and (2) after distal movement of the plunger, proximal movement of the needle along the axis.

Embodiment 2. The inserter of embodiment 1, further comprising a drive component disposed within the cavity, the drive component configured to (1) rotate within the cavity upon distal movement of the slider component and (2) result in movement to the needle and the plunger along the axis.

Embodiment 3. The inserter of any of the preceding embodiments, wherein the slot comprises first and second sections, and wherein distal movement of the slider component along the axis in the first section results in distal movement of the plunger along the axis, and wherein distal movement of the slider component in the second section results in proximal movement of the needle along the axis.

Embodiment 4. The inserter of embodiment 3, wherein distal movement of the slider component in the first section results in distal movement of the plunger while the needle remains substantially axially stationary relative to the housing, and wherein distal movement of the slider component in the second section results in proximal movement of the needle while the plunger remains substantially axially stationary relative to the housing.

Embodiment 5. The inserter of any of the preceding embodiments, wherein the slot extends substantially parallel relative to the axis.

Embodiment 6. The inserter of any of the preceding embodiments, wherein the slot has a length of less than 5 inches.

Embodiment 7. The inserter of any of the preceding embodiments, wherein the slot is linear and extends substantially parallel relative to a longitudinal axis of the housing.

Embodiment 8. An inserter for treating glaucoma, comprising: a housing having a longitudinal axis and an elongate slot extending substantially parallel relative to the axis over a length of less than 5 inches; a needle, having a lumen, movably coupled to the housing; a plunger, disposed within the lumen, movably coupled to the housing; and a slider component coupled to the needle and the plunger and slidable along the slot to result in both (1) distal movement of the plunger along the axis relative to the housing and (2) proximal movement of the needle along the axis relative to the housing.

Embodiment 9. The inserter of embodiment 8, wherein the slider component results in proximal movement of the needle relative to the housing after completion of distal movement of the plunger relative to the housing.

Embodiment 10. The inserter of any of embodiments 8 to 9, wherein the length of the slot is less than 4 inches.

Embodiment 11. The inserter of any of embodiments 8 to 10, wherein the length of the slot is less than 3 inches.

Embodiment 12. The inserter of any of embodiments 8 to 11, wherein the length of the slot is less than 2 inches.

Embodiment 13. The inserter of any of embodiments 8 to 12, wherein the length of the slot is less than 1 inch.

Embodiment 14. The inserter of any of embodiments 8 to 13, further comprising a drive component, disposed within an interior cavity of the housing, engaged with the needle and the plunger such that upon rotation of the drive component, the engagement results in a distal force to the plunger and a proximal force to the needle upon movement of the slider component along the axis.

Embodiment 15. The inserter of embodiment 14, wherein a longitudinal length of the drive component is greater than a length of the slot.

Embodiment 16. The inserter of any of embodiments 14 to 15, wherein the drive component comprises a first slot engaged with the needle, a second slot engaged with the plunger, and a third slot engage with the slider component.

Embodiment 17. The inserter of embodiment 16, wherein the first, second, and third slots each comprise a helical portion.

Embodiment 18. The inserter of any of embodiments 8 to 17, further comprising a gripping portion protruding from an outer surface of the housing configured to support an axial force directed in opposition to a direction of travel of the slider component.

Embodiment 19. An inserter for treating glaucoma, comprising: a needle having a lumen; a plunger, movable within the lumen; a drive component coupled to the needle and the plunger to result in movement to the needle and the plunger along a longitudinal axis of the inserter upon rotation of the drive component; and a slider component coupled to the housing and slidable along an elongate groove such that movement of the slider component along the axis rotates the drive component within the housing and results in movement of the needle and the plunger along the axis.

Embodiment 20. The inserter of embodiment 19, wherein the drive component comprises a cylindrical member.

Embodiment 21. The inserter of any of embodiments 19 to 20, wherein the drive component comprises a hollow cylindrical member.

Embodiment 22. The inserter of any of embodiments 19 to 21, wherein the drive component comprises a plurality of grooves.

Embodiment 23. The inserter of any of embodiments 19 to 22, wherein the drive component comprises a cylindrical member having a slider groove configured to engage with the slider component such that upon movement of the slider component, the engagement results in a rotational movement on the drive component.

Embodiment 24. The inserter of any of embodiments 19 to 23, wherein the drive component comprises a cylindrical member having a plunger groove configured to engage with the plunger such that upon rotation of the drive component, the engagement results in movement to the plunger along the axis in response to a rotational movement of the drive component.

Embodiment 25. The inserter of any of embodiments 19 to 24, wherein the drive component comprises a cylindrical member having a needle groove configured to engage with the needle such that upon rotation of the drive component, the engagement results in movement to the needle along the axis in response to a rotational movement of the drive component.

Embodiment 26. The inserter of any of embodiments 19 to 25, further comprising a housing having an interior cavity, wherein the drive component is supported within the cavity.

Embodiment 27. The inserter of embodiment 26, wherein the housing comprises an elongate slot extending from an outer surface of the housing into the cavity, the slider component being slidable along the slot.

Embodiment 28. The inserter of any of embodiments 26 to 27, wherein the housing has a distal portion and a sleeve extending from the distal portion, the sleeve comprising a lumen in which the needle extends.

Embodiment 29. The inserter of any of embodiments 26 to 28, wherein the housing further comprises a sleeve coupled to the distal portion, the sleeve having an abutting portion for abutting eye tissue to resist or prevent further movement of the device upon contact with the eye tissue.

Embodiment 30. The inserter of any of embodiments 26 to 29, further comprising a lock component configured to engage an outer structure of the housing to restrict movement of the slider component within the housing slot.

Embodiment 31. The inserter of any of embodiments 26 to 30, further comprising a lock component extending at least partially through the housing slot and configured to engage an outer structure of the drive component to restrict rotational movement of the drive component within the housing.

Embodiment 32. The inserter of any of embodiments 26 to 31, further comprising a knob component coupled to a proximal end of the housing, the knob component being rotatably coupled to the drive component such that rotation of the knob component results in a rotational movement to the drive component.

Embodiment 33. The inserter of any of embodiments 19 to 32, further comprising a needle assembly, the needle assembly comprising a needle driver that is slidably engaged with a needle groove of the drive component such that rotation of the drive component results in movement to the needle driver along the axis, wherein the needle is coupled to the needle driver such that movement of the needle driver along the axis results in movement of the needle along the axis.

Embodiment 34. The inserter of any of embodiments 19 to 33, wherein the needle is coupled to a rotational adjustment component, the adjustment component being rotatable to fix the rotational alignment of the needle relative to the housing.

Embodiment 35. The inserter of any of embodiments 19 to 34, wherein the needle is coupled to a rotational adjustment component, the adjustment component being coupled to a needle driver of a needle assembly, the adjustment component being rotatable relative to the needle driver such that rotation of the adjustment component rotation of the adjustment component changes a rotational alignment of the needle relative to the housing, wherein the adjustment component is rotatable to fix the rotational alignment of the needle relative to the housing.

Embodiment 36. The inserter of any of embodiments 19 to 35, further comprising a plunger assembly, the plunger assembly comprising a plunger driver that is slidably engaged with a plunger groove of the drive component such that rotation of the drive component results in movement to the plunger driver along the axis, wherein the plunger is coupled to the plunger driver such that movement of the plunger driver along the axis results in movement of the plunger along the axis.

Embodiment 37. An inserter for treating glaucoma, comprising: a housing having a distal portion and a longitudinal axis; a needle assembly, coupled to the housing distal portion, comprising a rotational adjustment component and a needle coupled to the adjustment component, wherein the adjustment component is rotatable to adjust a rotational alignment of the needle relative to the housing; and a plunger, movable within the lumen to result in an axial force on a shunt disposed within the lumen, to urge the shunt distally relative to the needle.

Embodiment 38. The inserter of embodiment 37, wherein the adjustment component is coupled to a needle driver of a needle assembly, the adjustment component being rotatable relative to the needle driver such that rotation of the adjustment component changes a rotational alignment of the needle relative to the housing, the needle driver configured to result in an axial force on the adjustment component that is transferred to the needle.

Embodiment 39. The inserter of any of embodiments 37 to 38, wherein the adjustment component comprises a pin extending radially from the needle assembly, the pin being actuatable to adjust the rotational alignment of the needle relative to the housing.

Embodiment 40. The inserter of any of embodiments 37 to 39, wherein the housing comprises an alignment slot and the adjustment component comprises a pin extending radially from the needle assembly through the alignment slot.

Embodiment 41. The inserter of any of embodiments 37 to 40, wherein the housing comprises an alignment slot having a circumferential portion, the adjustment component comprising a pin extending radially from the needle assembly through the alignment slot, the pin being movable within the circumferential portion to adjust the rotational alignment of the needle.

Embodiment 42. The inserter of any of embodiments 37 to 41, wherein the housing comprises an alignment slot having a circumferential portion and at least one longitudinal portion, the adjustment component comprising a pin extending radially from the needle assembly through the alignment slot, the pin being movable within the circumferential portion to adjust the rotational alignment of the needle, the pin further being movable within the at least one longitudinal portion upon movement of the needle along the axis.

Embodiment 43. The inserter of any of embodiments 37 to 42, wherein the housing comprises an alignment slot having a circumferential portion and at least three longitudinal portions, the adjustment component comprising a pin extending radially from the needle assembly through the alignment slot, the pin being movable within the circumferential portion to adjust the rotational alignment of the needle, the pin further being movable within one of the at least three longitudinal portions upon movement of the needle along the axis.

Embodiment 44. An inserter of any of embodiments 37 to 43, further comprising any of the features recited in embodiments 1 to 35.

Embodiment 45. A drive component for actuating an inserter for treating glaucoma, the drive component comprising a cylindrical body having first, second, and third elongate tracks extending along the body, wherein the first elongate track extends helically from a proximal portion toward a distal portion of the body, the second elongate track having (1) a first portion, extending helically about the body, and (2) a second portion, extending circumferentially about the body, the third elongate track having (i) a first portion, extending circumferentially about the body, and (ii) a second portion, extending helically about the body.

Embodiment 46. The component of embodiment 45, wherein the first, second, and third tracks each comprise a groove.

Embodiment 47. The component of any of embodiments 45 to 46, wherein the second portion of the second elongate track extends within a plane oriented substantially perpendicular relative to a longitudinal axis of the body.

Embodiment 48. The component of any of embodiments 45 to 47, wherein the first portion of the first elongate track extends within a plane oriented substantially perpendicular relative to a longitudinal axis of the body.

Embodiment 49. The component of any of embodiments 45 to 48, wherein the first portion of the second elongate track extends helically from the second portion of the second elongate track in a direction toward the proximal portion of the body.

Embodiment 50. The component of any of embodiments 45 to 49, wherein the second portion of the third elongate track extends helically from the first portion of the third elongate track in a direction toward the proximal portion of the body.

Embodiment 51. The component of any of embodiments 45 to 50, wherein the body comprises an inner lumen and the second and third tracks extend along an inner surface of the inner lumen.

Embodiment 52. The component of any of embodiments 45 to 51, wherein the body comprises an inner lumen and the second and third tracks comprise slots extending from an inner surface of the inner lumen to an outer surface of the body.

Embodiment 53. The component of any of embodiments 45 to 52, wherein the body comprises two pieces, the pieces being coupled together.

Embodiment 54. The component of any of embodiments 45 to 53, wherein the body comprises two pieces, couplable together, wherein at least one of the first, second, or third tracks extends along both of the pieces.

Embodiment 55. The component of any of embodiments 45 to 54, wherein the body comprises two pieces, couplable together, wherein the first track extends helically along both of the pieces.

Embodiment 56. The component of any of embodiments 45 to 55, wherein the body comprises two pieces, couplable together, wherein the second track extends helically along both of the pieces.

Embodiment 57. The component of any of embodiments 45 to 56, wherein the body comprises two pieces, couplable together, wherein the third track extends helically along both of the pieces.

Embodiment 58. The component of any of embodiments 45 to 57, wherein the first track extends helically along a substantially half rotation of the body.

Embodiment 59. The component of any of embodiments 45 to 58, wherein the second track extends helically along a substantially half rotation of the body.

Embodiment 60. The component of any of embodiments 45 to 59, wherein the third track extends helically along a substantially half rotation of the body.

Embodiment 61. The component of any of embodiments 45 to 60, wherein the body is hollow.

Embodiment 62. The drive component of embodiments 45 to 61, used in an inserter device having a housing, a needle, a plunger, and a slider component coupled to the housing and slidable therealong, the slider component being engaged with the drive component such that movement of the slider component along a longitudinal axis of the inserter rotates the drive component within the housing to move at least one of the needle or the plunger along the axis.

Embodiment 63. A method of manufacturing the component of embodiment 45, the body comprising first, second, and third tracks, wherein the body comprises two pieces being couplable together and the first track extends helically along both pieces, the method comprising forming a first of the two pieces with a first portion of the first track and forming a second of the two pieces with a second portion of the first track, the first and second portions of the first track being alignable to assemble the first track when the first and second pieces are coupled together.

Embodiment 64. The method of embodiment 63, further comprising forming any of the features recited in any of embodiments 45 to 60 onto the body.

Embodiment 65. A shunt retention device, comprising: an elongate, tubular body having first and second portions, the first portion having a taper such that the first portion can be inserted into a lumen of a needle to provide a precision press fit into the needle lumen, the second portion being graspable by an operator to facilitate insertion or withdrawal of the first portion relative to the needle lumen.

Embodiment 66. The device of embodiment 65, wherein the second portion comprises a bulbous end.

Embodiment 67. The device of any of embodiments 65 to 66, wherein the body comprises a steel material.

Embodiment 68. An inserter for treating glaucoma, comprising: a housing having a distal portion, an outer surface, and an elongate slot extending along the outer surface; a needle, having a lumen, coupled to the housing distal portion; a plunger, disposed within the lumen, movable to result in an axial force on a shunt to urge the shunt distally relative to the needle; a slider component coupled to the housing and slidable along the elongate slot, the slider component being configured to result in an axial force on at least one of the plunger or the needle; and a grip section disposed proximally relative to the slider component, the grip section having first and second portions, wherein the first portion extends radially outward for providing resistance against distal movement of an operator's hand relative to the housing, and the second portion extends radially outward for providing resistance against proximal movement of an operator's hand relative to the housing.

Embodiment 69. The inserter of embodiment 68, wherein the grip section comprises a saddle shape, wherein the first and second portions extend on opposing sides of the saddle.

Embodiment 70. The inserter of any of embodiments 68 to 69, wherein the grip section extends circumferentially around the housing.

Embodiment 71. The inserter of any of embodiments 68 to 70, wherein the grip section comprises a valley portion disposed between the first and second portions, the valley portion comprising an inner diameter, the first and second portions comprising a maximum outer diameter, the maximum outer diameter being between about 1.5 and about 5 times as large as the inner diameter.

Embodiment 72. The inserter of any of embodiments 68 to 71, wherein the grip section comprises a valley portion disposed between the first and second portions, the valley portion comprising an inner diameter, the first and second portions comprising a maximum outer diameter, the maximum outer diameter being between about 2 and about 4 times as large as the inner diameter.

Embodiment 73. The inserter of any of embodiments 68 to 72, wherein the grip section comprises a valley portion disposed between the first and second portions, the valley portion comprising an inner diameter, the first and second portions comprising a maximum outer diameter, the maximum outer diameter being between about 2.5 and about 3 times as large as the inner diameter.

Embodiment 74. The inserter of any of embodiments 68 to 73, wherein the grip section comprises a valley portion disposed between the first and second portions, the valley portion comprising an inner diameter, the first portion comprising a first outer diameter and the second portion comprising a second outer diameter, the first and second outer diameters being between larger than the inner diameter, the first outer diameter being less than the second outer diameter.

Embodiment 75. The inserter of any of embodiments 1 to 44, further comprising a grip section disposed proximally relative to the slider component, the grip section having first and second portions, wherein the first portion extends radially outward for providing resistance against distal movement of an operator's hand relative to the housing, when operating the inserter, and the second portion extends radially outward for providing resistance against proximal movement of an operator's hand relative to the housing, when operating the inserter.

Embodiment 76. The inserter of embodiment 1 to 44 or 75, wherein the grip section comprises a saddle shape.

Embodiment 77. The inserter of any of embodiments 1 to 43 or 73 to 75, wherein the grip section extends circumferentially around the housing.

Embodiment 78. The inserter of any of embodiments 1 to 43 or 73 to 75, wherein the grip section comprises a valley portion disposed between the first and second portions, the valley portion comprising an inner diameter, the first and second portions comprising a maximum outer diameter, the maximum outer diameter being between about 1.5 and about 5 times as large as the inner diameter.

Embodiment 79. The inserter of any of embodiments 1 to 43 or 73 to 75, wherein the grip section comprises a valley portion disposed between the first and second portions, the valley portion comprising an inner diameter, the first and second portions comprising a maximum outer diameter, the maximum outer diameter being between about 2 and about 4 times as large as the inner diameter.

Embodiment 80. The inserter of any of embodiments 1 to 43 or 73 to 75, wherein the grip section comprises a valley portion disposed between the first and second portions, the valley portion comprising an inner diameter, the first and second portions comprising a maximum outer diameter, the maximum outer diameter being between about 2.5 and about 3 times as large as the inner diameter.

Embodiment 81. The inserter of any of embodiments 1 to 43 or 73 to 80, wherein the grip section comprises a valley portion disposed between the first and second portions, the valley portion comprising an inner diameter, the first portion comprising a first outer diameter and the second portion comprising a second outer diameter, the first and second outer diameters being between larger than the inner diameter, the first outer diameter being less than the second outer diameter.

Embodiment 82. An inserter comprising any of the features recited in any of embodiments 1 to 43.

Embodiment 83. A method of treating an eye, comprising: introducing a needle into the eye through a cornea of the eye; advancing a bevel of the needle to a location intermediate a superficial layer and a deep layer; and rotating the bevel to create a space between the superficial layer and the deep layer.

Embodiment 84. The method of embodiment 83, wherein the advancing comprises advancing the bevel such that a plane of the bevel is substantially parallel relative to a surface of the superficial layer.

Embodiment 85. The method of any of embodiments 83 to 84, wherein the rotating comprises rotating the bevel from a first configuration in which the bevel lies substantially coplanar with an interface of the superficial layer and the deep layer to a second configuration in which the bevel extends transversely relative to the interface.

Embodiment 86. The method of embodiment 85, wherein in the second configuration, the bevel extends substantially perpendicular relative to the interface.

Embodiment 87. The method of any of embodiments 83 to 86, wherein the advancing comprises passing the bevel through sclera until exiting the sclera.

Embodiment 88. The method of any of embodiments 83 to 87, wherein the superficial layer comprises conjunctiva.

Embodiment 89. The method of any of embodiments 83 to 88, wherein the superficial layer comprises intra-Tenon's adhesion layer.

Embodiment 90. The method of any of embodiments 83 to 89, wherein the deep layer comprises sclera.

Embodiment 91. The method of any of embodiments 83 to 90, wherein the deep layer comprises intra-Tenon's adhesion layer.

Embodiment 92. The method of any of embodiments 83 to 91, wherein the superficial and deep layers comprise sclera.

Embodiment 93. A method of treating an eye, comprising: introducing a needle into the eye through a cornea of the eye; advancing a bevel of the needle to a location intermediate a superficial layer and a deep layer; and injecting a fluid from bevel to create a space between the superficial layer and the deep layer.

Embodiment 94. The method of embodiment 93, wherein the advancing comprises advancing the bevel such that a plane of the bevel is substantially parallel relative to a surface of the superficial layer.

Embodiment 95. The method of any of embodiments 93 to 94, wherein the fluid comprises a balanced salt solution.

Embodiment 96. The method of any of embodiments 93 to 95, wherein the superficial layer comprises conjunctiva.

Embodiment 97. The method of any of embodiments 93 to 95, wherein the superficial layer comprises intra-Tenon's adhesion layer.

Embodiment 98. The method of any of embodiments 93 to 97, wherein the deep layer comprises sclera.

Embodiment 99. The method of any of embodiments 93 to 95 or 97, wherein the deep layer comprises intra-Tenon's adhesion layer.

Embodiment 100. The method of any of embodiments 93 to 95, wherein the superficial and deep layers comprise superficial and deep layers of intra-Tenon's adhesion layer.

The foregoing description is provided to enable a person skilled in the art to practice the various configurations described herein. While the subject technology has been particularly described with reference to the various Figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. An inserter for treating glaucoma, comprising:
a housing having a distal portion and a longitudinal axis;
a needle assembly, coupled to the distal portion of the housing, comprising a rotational adjustment component and a needle coupled to the rotational adjustment component, wherein the rotational adjustment component is rotatable to rotate the needle relative to the housing; and
a plunger, movable within a lumen of the needle to result in an axial force on a shunt disposed within the lumen, to urge the shunt distally relative to the needle.

2. The inserter of claim 1, wherein the rotational adjustment component is coupled to a needle driver of the needle assembly, the rotational adjustment component being rotatable relative to the needle driver such that rotation of the rotational adjustment component changes a rotational alignment of the needle relative to the housing, the needle driver configured to result in an axial force on the rotational adjustment component that is transferred to the needle.

3. The inserter of claim 1, wherein the rotational adjustment component comprises a pin extending radially from the needle assembly, the pin being actuatable to adjust a rotational alignment of the needle relative to the housing.

4. The inserter of claim 1, wherein the housing comprises an alignment slot and the rotational adjustment component comprises a pin extending radially from the needle assembly through the alignment slot.

5. The inserter of claim 1, wherein the housing comprises an alignment slot having a circumferential portion, the rotational adjustment component comprising a pin extending radially from the needle assembly through the alignment slot, the pin being movable within the circumferential portion to adjust a rotational alignment of the needle.

6. The inserter of claim 1, wherein the housing comprises an alignment slot having a circumferential portion and at least one longitudinal portion, the rotational adjustment component comprising a pin extending radially from the needle assembly through the alignment slot, the pin being movable within the circumferential portion to adjust a rotational alignment of the needle, the pin further being movable within the at least one longitudinal portion upon movement of the needle along the longitudinal axis.

7. The inserter of claim 1, wherein the housing comprises an alignment slot having a circumferential portion and at least three longitudinal portions, the rotational adjustment component comprising a pin extending radially from the needle assembly through the alignment slot, the pin being movable within the circumferential portion to adjust a rotational alignment of the needle, the pin further being movable within one of the at least three longitudinal portions upon movement of the needle along the longitudinal axis.

8. The inserter of claim 1, further comprising a drive component coupled to at least one of the needle or the plunger to result in movement to at least one of the needle or the plunger along the longitudinal axis of the inserter upon rotation of the drive component; and a slider component coupled to the housing and slidable along an elongate groove such that movement of the slider component along the longitudinal axis rotates the drive component within the housing and results in movement of at least one of the needle or the plunger along the longitudinal axis.

9. The inserter of claim 8, wherein the drive component comprises a cylindrical member having a slider groove configured to engage with the slider component such that movement of the slider component, results in a rotational movement on the drive component.

10. The inserter of claim 1, further comprising a needle mount coupled to the needle, and the rotational adjustment component is positioned between the needle mount and the plunger.

11. The inserter of claim 1, wherein the rotational adjustment component comprises an aperture extending therethrough, and a needle driver of the needle assembly extends through the aperture.

12. The inserter of claim 11, wherein further comprising a needle mount coupled to the needle, and the plunger extends through the needle driver, the rotational adjustment component, and the needle mount.

13. The inserter of claim 11, wherein the needle driver comprises a locking ridge engaged against the rotational adjustment component to resist longitudinal movement of the needle driver relative to the rotational adjustment component.

14. The inserter of claim 1, wherein further comprising a needle mount coupled to the needle, and the rotational adjustment component engages against the needle mount to resist longitudinal and rotational movement of the needle relative to the rotational adjustment component.

15. The inserter of claim 1, wherein the adjustment component is moveable, relative to the housing, in a rotational direction around the longitudinal axis of the housing.

16. An inserter for treating glaucoma, comprising:
a housing having a distal portion and a longitudinal axis;
a needle assembly, coupled to the distal portion of the housing, comprising an adjustment component and a needle coupled to the adjustment component, wherein the adjustment component is movable to rotate the needle relative to the longitudinal axis of the housing; and
a plunger within a lumen of the needle, wherein the plunger is moveable, relative to the needle, to result in an axial force on a shunt disposed within the lumen.

17. The inserter of claim 16, wherein the plunger is moveable along the longitudinal axis of the housing.

18. The inserter of claim 16, wherein a distal end of the needle comprises a bevel, and the longitudinal axis of the housing extends through a plane of the bevel.

19. The inserter of claim 16, wherein the housing comprises an alignment slot and the adjustment component comprises a pin extending radially from the needle assembly through the alignment slot.

20. The inserter of claim 16, wherein the adjustment component is moveable, relative to the housing, in a longitudinal direction along the longitudinal axis of the housing.

* * * * *